United States Patent
Ando et al.

(10) Patent No.: US 6,214,208 B1
(45) Date of Patent: Apr. 10, 2001

(54) METHOD AND APPARATUS FOR MEASURING NOX GAS CONCENTRATION

(75) Inventors: Masashi Ando, Aichi; Noboru Ishida, Kakamigahara; Satoshi Sugaya, Inuyama; Takafumi Oshima, Nagoya; Norihiko Nadanami, Kasugai; Takaki Ootuka, Komaki; Yoshikuni Sato, Nagoya; Tatsuo Okumura, Gifu, all of (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 08/982,869

(22) Filed: Dec. 2, 1997

(30) Foreign Application Priority Data

Dec. 2, 1996 (JP) .................................................. 8-337519

(51) Int. Cl.$^7$ .......................... G01N 27/407; G01N 31/10
(52) U.S. Cl. .......................... 205/781; 436/118; 436/151; 436/152; 73/23.31; 73/31.05
(58) Field of Search ...................... 422/83, 98; 73/23.31, 73/31.05; 436/116, 117, 118, 151, 152; 205/781; 204/424–427

(56) References Cited

U.S. PATENT DOCUMENTS

| | | | |
|---|---|---|---|
| 4,645,572 | 2/1987 | Nishizawa et al. | 204/1 T |
| 4,722,779 | 2/1988 | Yamada et al. | |
| 4,770,760 | 9/1988 | Noda et al. | 204/425 |

(List continued on next page.)

FOREIGN PATENT DOCUMENTS

| | | |
|---|---|---|
| 3924644 A1 | 1/1991 | (DE) . |
| 0 517 366 | 12/1992 | (DE) . |
| 4311851 A1 | 10/1994 | (DE) . |

(List continued on next page.)

OTHER PUBLICATIONS

*Solid Electrolytes for Gas Sensing at High Temperatures, Multi Electrode Setup to Analyze Gas Mixtures*, G. Reinhardt, S.I. Somov, U. Schonauer, U. Guth and W. Gopen, 1995.6.

Society of Automotive Engineers, Inc., *Thick Film ZrO2 $NO_x$ Sensor*, No. 960334, pp. 137–142, by Nobuhide Kato, Kunihiko Nakagaki and Noriyuki Ina, NGK Insulators, Ltd.

Society of Automotive Engineers, Inc., *Performance of Thick Film $NO_x$ Sensor on Diesel and Gasoline Engines*, Feb. 24–27, 1997, by Nobuhide Kato, Yasuhiko Hamada and Hiroshi Kurachi, pp. 199–206.

*Primary Examiner*—Jill Warden
(74) *Attorney, Agent, or Firm*—Morrison & Foerster, LLP

(57) ABSTRACT

This is a method and apparatus for accurately determining a NOx concentration of a measurement gas that contains $H_2O$ and/or $CO_2$, without being affected by a dissociation of $H_2O$ and/or $CO_2$.

In this method and apparatus, (1) the NOx-measurement gas containing $H_2O$ and/or $CO_2$ is introduced to travel through a heated flow channel formed by an oxygen ion conductive solid ceramic electrolyte body that electrically control amount of $O_2$ from the flow channel, (2) while said measurement gas travels, a residual gas including NO and $H_2O$ and/or $CO_2$ is formed from the measurement gas, (3) said residual gas is flowed to contact a catalytic electrode to which a negative polarity of a low voltage that does not dissociate $H_2O$ and/or $CO_2$ but dissociates NO is applied, so that said electrode dissociates a NO gas of the residual gas into N ions and O ions and flows an electric current through the electrolyte body in proportion to an amount of the O ions dissociated from said residual gas at the electrode, and (4) the NOx concentration in the measurement gas is determined based on the current.

The low voltage preferably applied in the above (3) is about 350–450 mV.

25 Claims, 47 Drawing Sheets

U.S. PATENT DOCUMENTS

| | | | |
|---|---|---|---|
| 4,902,400 | 2/1990 | Usami et al. | 204/426 |
| 4,909,072 | 3/1990 | Logothetis et al. | 73/116 |
| 4,927,517 | 5/1990 | Mizutani et al. . | |
| 5,028,309 | 7/1991 | Nishizawa et al. | 204/425 |
| 5,034,112 | 7/1991 | Murase et al. | 204/406 |
| 5,049,254 | 9/1991 | Logothetis et al. | 204/425 |
| 5,080,765 | 1/1992 | Wang et al. | 204/153.1 |
| 5,089,113 | 2/1992 | Logothetis et al. | 204/425 |
| 5,145,566 | 9/1992 | Logothetis et al. | 204/153.18 |
| 5,217,588 | 6/1993 | Wang et al. | 204/153.1 |
| 5,250,169 | 10/1993 | Logothetis et al. | 204/424 |
| 5,288,375 | 2/1994 | Logothetis et al. | 204/153.18 |
| 5,304,294 | 4/1994 | Wang et al. | 204/426 |
| 5,397,442 * | 3/1995 | Wachsman | 204/153.16 |
| 5,476,001 * | 12/1995 | Hoetzel et al. | 73/23.31 |
| 5,643,429 * | 7/1997 | Wachsman | 205/781 |
| 5,672,811 | 9/1997 | Kato et al. | 73/204 |

FOREIGN PATENT DOCUMENTS

| | | |
|---|---|---|
| 0 060 944 | 9/1982 | (EP) . |
| 0 257 842 | 3/1988 | (EP) . |
| 0 678 740 | 10/1995 | (EP) . |
| 0 678 740 A1 | 10/1995 | (EP) . |
| 63-38154 | 2/1988 | (JP) . |
| 64-27751 | 1/1989 | (JP) . |
| 64-39545 | 2/1989 | (JP) . |
| 2-1543 | 1/1990 | (JP) . |
| 2-122255 | 5/1990 | (JP) . |
| 5-18059 | 10/1993 | (JP) . |
| 8-14570 | 2/1996 | (JP) . |
| 8-247995 | 9/1996 | (JP) . |
| 8-271476 | 10/1996 | (JP) . |
| 9-288084 | 11/1997 | (JP) . |
| 9-288085 | 11/1997 | (JP) . |
| 9-288086 | 11/1997 | (JP) . |
| 9-288087 | 11/1997 | (JP) . |
| 95/30146 | 9/1995 | (WO) . |

* cited by examiner

GRADIENT OF OXYGEN CONCENTRATION

Vs = 350mV

Influence to NO measurement of $H_2O=10\%$, $CO_2=10\%$

GRADIENT OF OXYGEN CONCENTRATION

RELATION OF O2% v. PUMP

RELATION OF TEMPERATURE v. OFFSET

FIG. 46
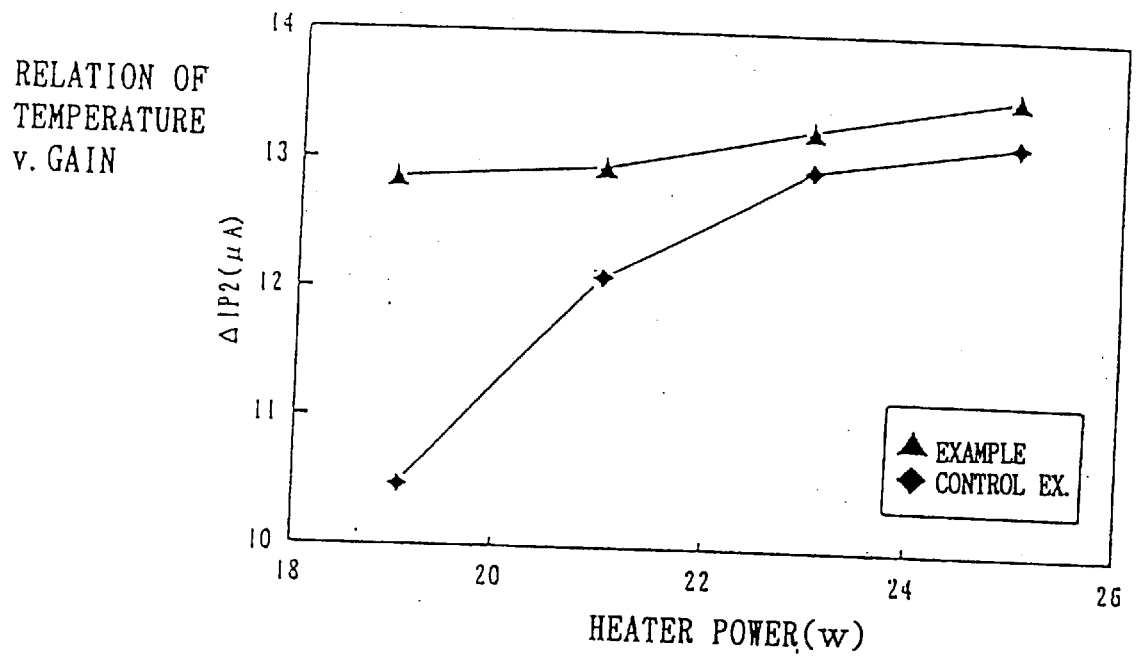
RELATION OF TEMPERATURE v. GAIN
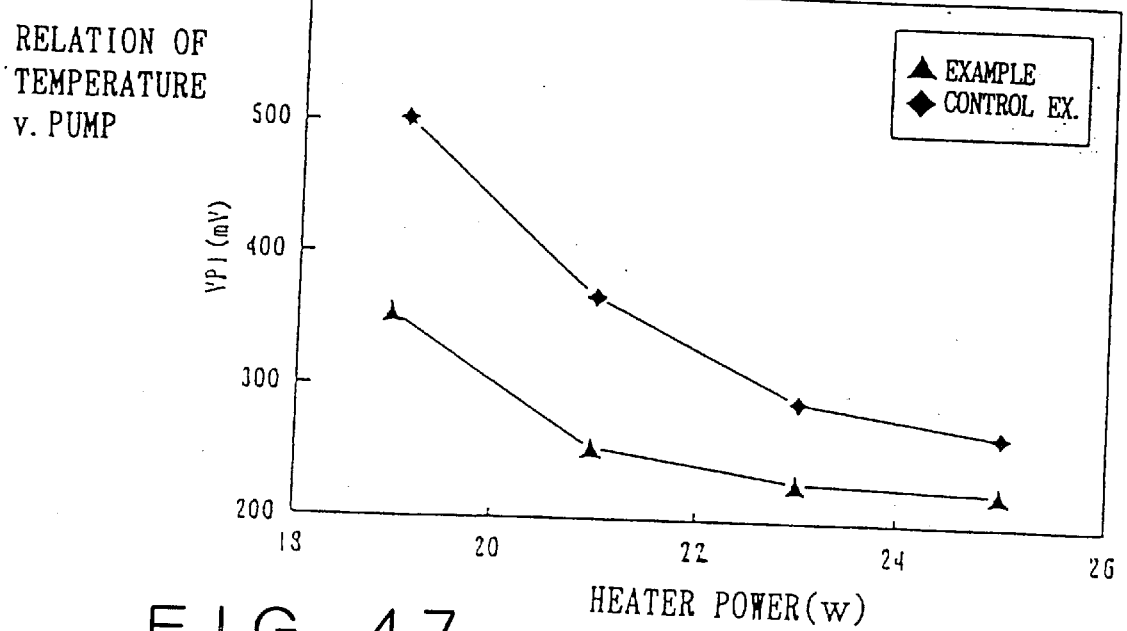
RELATION OF TEMPERATURE v. PUMP
FIG. 47

81 : THRU HOLE OR POROUS
O2 IS RETURNED VIA
78d, 81 & 76c TO 1ST
MEASURING SPACE

O2
NO→1/2N2+1/2O2

O2 IS PUMPED OUT
VIA LEAD 78d.

O2
NO→1/2N2+1/2O2    81 ; POROUS
O2 IS RETURNED TO
2ND MEASURING SPACE

FIG. 61A
Vp2effec.=Vp2−EMF
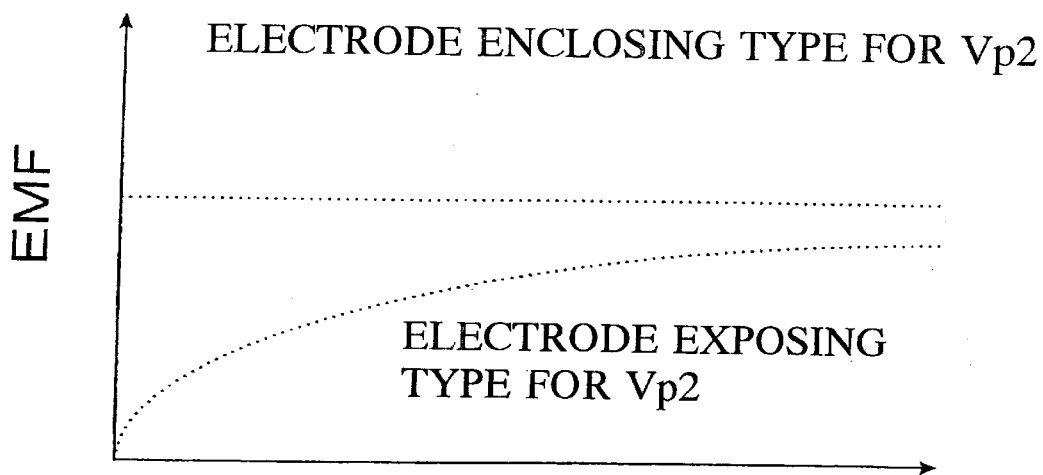
O2 CONCENTRATION IN MEASUREMENT GAS (%)
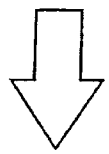
FIG. 61B
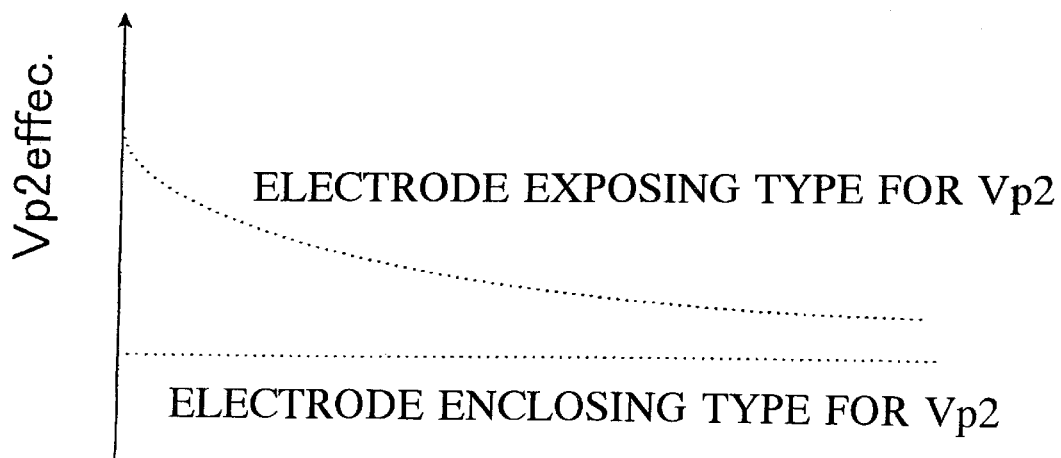
O2 CONCENTRATION IN MEASUREMENT GAS (%)

EXPOSED TYPE

- first flow channel
- first diffusion hole
- oxygen concentration sensor cell
- second diffusion hole
- second flow channel

ENCLOSED TYPE

- first flow channel
- oxygen concentration sensor cell
- first diffusion hole
- second diffusion hole
- second flow channel
- second concentration sensor cell

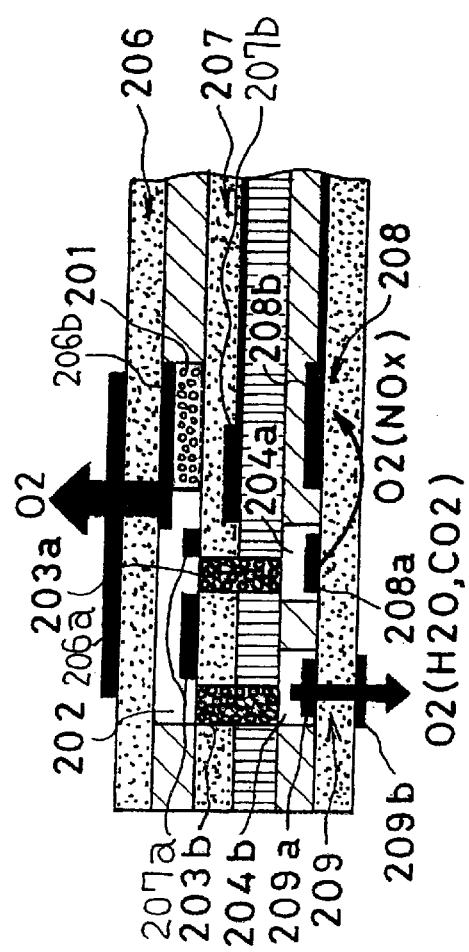

FIG. 67

201; first diffusion hole
202; first flow channel
203a; second diffusion hole
203b; third diffusion hole
204a; second flow channel
204b; third flow channel
206; oxygen drawing cell
(first oxygen ion pump cell)
206a, 206b; electrode
207; oxygen concentration sensor cell
207a, 207b; electrode
208; NOx gas sensor cell
(second oxygen ion pump cell)
208a, 208b; electrode
209; $H_2O$, $CO_2$ gas sensor cell
(third oxygen ion pump cell)
209a, 209b; electrode

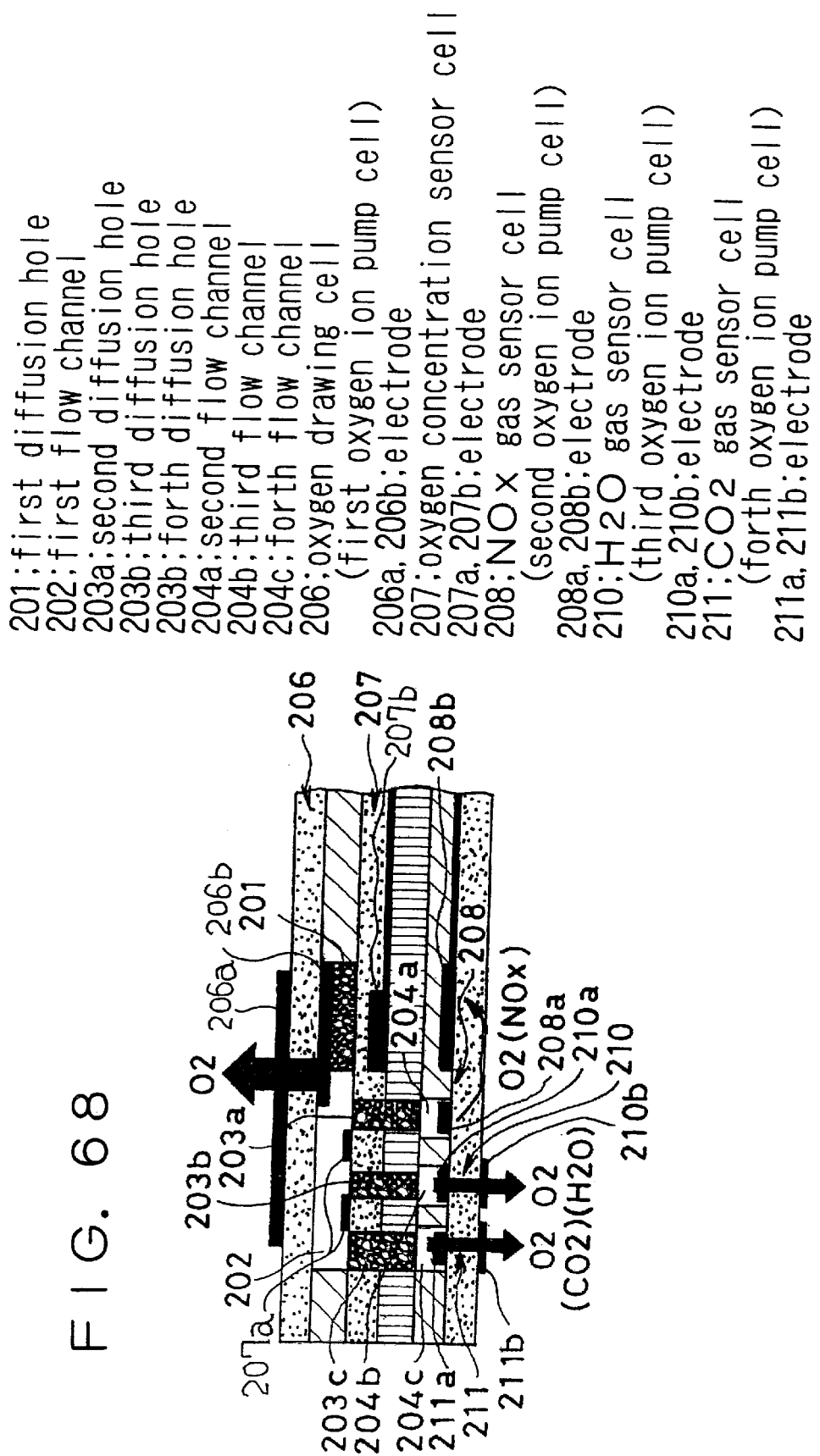

FIG. 68

201: first diffusion hole
202: first flow channel
203a: second diffusion hole
203b: third diffusion hole
203b: forth diffusion hole
204a: second flow channel
204b: third flow channel
204c: forth flow channel
206: oxygen drawing cell
(first oxygen ion pump cell)
206a, 206b: electrode
207: oxygen concentration sensor cell
207a, 207b: electrode
208: NOx gas sensor cell
(second oxygen ion pump cell)
208a, 208b: electrode
210: H2O gas sensor cell
(third oxygen ion pump cell)
210a, 210b: electrode
211: CO2 gas sensor cell
(forth oxygen ion pump cell)
211a, 211b: electrode 201; first diffusion hole
202; first flow channel
203a; second diffusion hole
203b; third diffusion hole
204a; second flow channel
204b; third flow channel
206; oxygen drawing cell
(first oxygen ion pump cell)
206a, 206b; electrode
207; oxygen concentration sensor cell
207a, 207b; electrode
208; NOx gas sensor cell
(second oxygen ion pump cell)
208a, 208b; electrode
209; H2O, CO2 gas sensor cell
(third oxygen ion pump cell)
209a, 209b; electrode

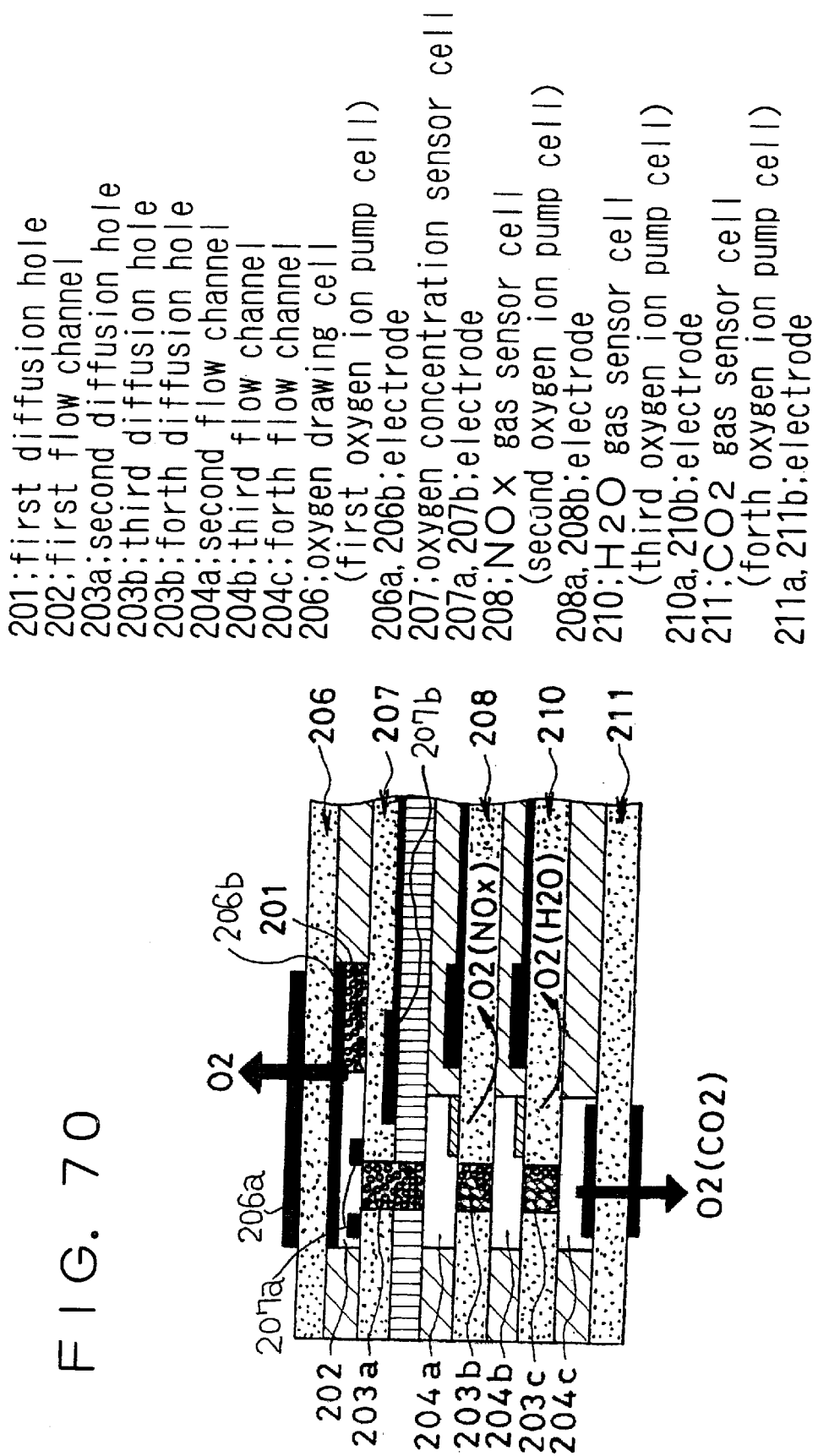

FIG. 70

201; first diffusion hole
202; first flow channel
203a; second diffusion hole
203b; third diffusion hole
203b; forth diffusion hole
204a; second flow channel
204b; third flow channel
204c; forth flow channel
206; oxygen drawing cell
  (first oxygen ion pump cell)
206a, 206b; electrode
207; oxygen concentration sensor cell
207a, 207b; electrode
208; NOx gas sensor cell
  (second oxygen ion pump cell)
208a, 208b; electrode
210; H2O gas sensor cell
  (third oxygen ion pump cell)
210a, 210b; electrode
211; CO2 gas sensor cell
  (forth oxygen ion pump cell)
211a, 211b; electrode

*H. Osanai et al., Fujikura Technical Review 17 (1988), 34-42

METHOD AND APPARATUS FOR MEASURING NOX GAS CONCENTRATION

TECHNICAL FIELD OF THE INVENTION

This invention relates to a method for measuring the concentrations of the NOx gas and an apparatus or sensor for carrying out the measurement method. More particularly, it relates to a method for measuring the NOx gas concentration used in exhaust gases containing a large quantity of $H_2O$, and a NOx gas concentration sensor.

BACKGROUND OF THE INVENTION

Recently, researches into directly measuring the concentration of the NOx gas for controlling the infernal combustion engine or catalysts are proceeding in meeting with intensification of regulations on vehicle exhaust gases.

In particular, researches are going on extensively for a NOx gas concentration sensor of the type in which the oxygen is pumped out by a first oxygen ion pump cell using a solid electrolyte (oxygen conductor) such as zirconia, so as not to cause decomposition of the NOx gas ($2NO \rightarrow N_2+O_2$) by the first oxygen ion pump cell and in which oxygen is further pumped out from the NOx-gas-containing residual gas by the second oxygen ion pump cell for decomposing NOx and measuring the current generated by dissociated oxygen ions for detecting the NOx gas concentration because measurement of the NOx gas concentration is thought to be easily made without being affected by interfering gases contained in the exhaust gases, such as HC or CO.

SUMMARY OF THE DISCLOSURE

In the course of investigation toward the present invention following problem has been encountered.

According to the finding reached by the present inventors, the above method has a drawback that, if $H_2O$ is mixed into the NOx gas concentration sensor, the NOx concentration cannot be measured accurately.

It is therefore an object of the present invention to provide a method for measuring the NOx gas concentration for enabling accurate measurement of the NOx gas concentration in a $H_2O$ containing atmosphere and a NOx gas concentration sensor for carrying out the method.

Other problems and objects of the present invention will become apparent in the entire disclosure.

Among various aspects of the present invention there are the following elements. The elements included in aspect (1—1) are as follows: there is a first step of introducing the gas under measurement containing NOx into the flow channel. The oxygen gas is drawn or evacuated to outside of the flow channel via a ceramic body having an electrically controllable conducting rate of oxygen. A NOx concentrated residual gas is formed in the flow channel. A voltage is applied to the ceramic body to an extent that does not substantially dissociate $H_2O$ in the residual gas. Particularly, a voltage lower than the dissociation voltage between hydrogen and oxygen of at least $H_2O$ (H—O dissociation voltage) in the residual gas is impressed across the electrodes formed on the outside body. NOx in the NOx concentrated residual gas is dissociated into nitrogen and oxygen. The current caused by NOx dissociation flowing in the ceramic body is measured across the electrodes. The current is generated by the electro-chemical action of oxygen dissociated from the NOx gas during the dissociation step. The NOx concentration is determined based on this current.

According to further aspect based on aspect (3-1), the flow of the gas into the flow channel is restricted (aspect 1-2). The flow of the residual gas to the electrode for the NOx dissociation is restricted (aspect 1-3).

The flow chart comprises a first flow channel and a second flow channel communicating with the first flow channel, the formation of the residual gas for concentrating NOx without dissociating $H_2O$ is performed in the first flow channel, and NOx is dissociated in the second flow channel (aspect 1-4).

According to aspect (2-1), there is provided a NOx gas concentration sensor for measuring the NOx concentration on a gas under measurement. The sensor comprises a ceramic body having an electrically controllable conducting rate of oxygen ion; a flow channel provided facing said ceramic body so that that NOx containing gas under measurement will flow therein, with the NOx gas in the gas under measurement being varied in the concentration during the process of movement of the gas under measurement therethrough; and means (generally pumping cell) for extracting the oxygen gas from the gas under measurement via said ceramic body to outside of the flow channel for forming a residual gas, in said flow channel, having a NOx concentration different from before entering the flow channel; and a plurality of electrodes formed on said ceramic body so that NOx in the residual gas is dissociated into nitrogen and oxygen by applying a voltage to an extent that $H_2O$ in the residual gas is substantially not dissociated. The sensor further comprises generally circuit means, i.e., means for measuring a current flowing in said ceramic body across said electrodes, said current being generated by the electro-chemical operation of oxygen dissociated from the NOx gas; and means for determining the NOx concentration in the gas under measurement based on said measured current.

According to aspect (2—2), in the flow channel there is disposed an electrode for extracting oxygen gas out of the flow channel along the flowing direction of the measurement gas, and wherein the electrode has a length relative to the entire length of the flow channel being:

electrode/entire length=¼ to ¾.

According to aspect (2-3), the flow channel comprises a first flow channel in which residual gas is formed, and a second flow channel in which NOx is dissociated, the second flow channel having an inlet communicating to the first flow channel, and the electrode disposed in the flow channel for extracting the oxygen gas out of the flow channel extends from the vicinity of a gas flow restrictor disposed in the first flow channel until at longest a position closer to said gas flow restrictor than the inlet of the second flow channel.

In the NOx gas concentration sensor, the sensor output (IP2) usually has temperature dependency and oxygen concentration dependency, thus obstructing accurate measurement of the NOx gas concentration. The NOx gas concentration sensor according to the aspects 2—2 or 2-3 exhibits low oxygen concentration dependency to enable accurate measurement of the NOx gas concentration. If the sensor according to the aspects 2—2 or 2-3 is mounted on the exhaust system of an internal combustion engine driven in the vicinity of a lean range or a theoretical value point (stoichiometrical point), the NOx gas concentration detection output is stabilized in case of lean-rich switching, that is in case of acute change in the oxygen concentration in the exhaust gases.

According to further aspect (2-4), the NOx gas concentration sensor is formulated as follow: The ceramic body is formed of plural ceramic layers laminated together; the flow channel includes a first flow channel for forming residual gas and a second flow channel for dissociating NOx, the first and second flow channels extending along the surface of said laminated ceramic layers; and the first and second flow channels communicate with each other by a flow channel extending in the laminating direction of the ceramic layers.

According to aspect (2-5), in the NOx gas concentration sensor1, an oxygen concentration detecting electrode for detecting the oxygen concentration in the flow channel is formed on the ceramic body facing the flow channel, wherein an oxygen concentration for generating a reference potential versus the oxygen concentration detecting electrode is formed on the ceramic body outside of the flow channel; the oxygen concentration reference electrode is an auto-generating reference electrode across which a voltage is impressed for transporting oxygen towards the reference electrode for providing a constant oxygen concentration around this reference electrode.

According to aspect (2-6), the electrode provided outside the channel for drawing the oxygen gas to outside of the flow channel is sealed or covered. This electrode communicates with atmosphere via a lead and is provided with a gas diffusion resistance.

According to aspect (2-7) the electrode provided in the flow channel for drawing the oxygen gas to outside of said channel, a solid electrolyte component having oxygen ion conductivity carries a component inhibiting the NOx dissociation.

Further aspects relating to the structure of the sensor will be later discussed in more detail with reference to the embodiments of the present invention.

Further aspects relating to the method for measuring the NOx gas concentration generally relate to aspects (3-1) to (3-4), which correspond to claims 12 to 15, respectively.

According to aspect (4-1), there is provided a NOx gas concentration sensor comprising a first measurement chamber into which a measurement gas is introduced via a first diffusion resistance; an oxygen partial pressure detection electrode for measuring the oxygen partial pressure in the measurement gas in the first measurement chamber; a first oxygen ion pump cell for pumping out the oxygen in the measurement gas in the first measurement chamber therefrom, based on a potential of the oxygen partial pressure detection electrode, to a sufficient extent such as not to decompose NOx in the measurement gas; a second measurement chamber into which a gas in introduced from the first measurement chamber via a second diffusion resistance; and a second oxygen ion pump cell having paired electrodes on inner and outer sides of the second measurement chamber, the second oxygen ion pump cell being flown through by a current caused by oxygen dissociated on decomposition of NOx in the second measurement chamber on impression of a voltage across the paired electrodes. In this sensor, the voltage impressed across the paired electrodes of the second oxygen ion pump cell is set such as substantially not to dissociate $H_2O$ present in the second measurement chamber.

According to aspect 3-1, the voltage impressed across the paired electrodes disposed on inside and outside of the measuring chamber forming a second oxygen ion pump cell is set such as substantially not to dissociate $H_2O$ present in the measurement chamber. This measurement method is applied to NOx gas concentration detector having a first measurement chamber into which a measurement gas is introduced via a first diffusion resistance, an oxygen partial pressure detection electrode for measuring the oxygen partial pressure in the measurement gas in first measurement chamber, a first oxygen ion pump cell for pumping out the oxygen in the measurement gas in the first measurement chamber to outside of the chamber, based on a potential of the oxygen partial pressure detection electrode, to a sufficient extent of not decomposing the NOx in the measurement gas, a second measurement chamber into which a gas is introduced from the first measurement chamber via a second diffusion resistance and a second oxygen ion pump cell having paired electrodes on an inner and outer sides of the second measurement chamber, the second oxygen ion pump cell being flown through by the current generated by oxygen dissociated on decomposition of NOx in the second measurement chamber on impression of a voltage across the paired electrodes, in which the current flowing through the second oxygen ion pump cell is measured for finding the NOx gas concentration from the current. By setting the voltage impressed across paired electrodes provided on the inner and outer sides of the second oxygen ion pump cell to a pre-set value, it becomes possible to prevent dissociation of $H_2O$ in the second measurement chamber.

With the aspect 3-1, since dissociation and decomposition of $H_2O$ is substantially prevented from occurring in the second measurement chamber, the pump current in the second oxygen ion pump cell is not increased due to oxygen generated by dissociation of $H_2O$ thus maintaining NOx gas concentration calculation (convention) accuracy (effect (1)). In particular, by controlling the oxygen concentration in the second measurement chamber to a condition precluding $H_2O$ dissociation, it becomes possible to improve the $H_2O$ concentration dependency of the offset value of the second oxygen ion pump cell current $Ip2$.

In aspect 3-2 to 3—3 of the present invention, based on the above-mentioned aspect 3-1, since the voltage applied across the second oxygen ion pump cell can be set to 300 to 400 mV or to 400 to 500 mV if the electrode provided on the outer side of the second oxygen ion pump cell is or is not exposed to the atmosphere under measurement, respectively, not only can the effect (1) displayed, but also there occurs (2): decomposition of NOx gas (primarily NO) sufficiently to increase the pump current of the second oxygen ion pump cell produced on NOx gas decomposition, that is to increase the gain, such as to maintain NOx gas concentration measurement (convention of calculation) accuracy.

Preferably, the voltage is set to the former or the latter if the electrodes are provided on both sides of the solid electrolyte layer and the electrode on the outer side of the flow channel is substantially exposed, or if both electrodes are provided on one side of the solid electrolyte layer (one of the electrodes being preferably isolated from the atmosphere in the flow channel), respectively.

In aspect 3-4, which is desirable in connection with the above-mentioned aspect 3-1, oxygen in the gas under measurement is pumped out by the first ion pump cell so that the voltage of the oxygen partial pressure sensor electrode will be equal to 150 to 450 mV. This enables the oxygen concentration in the gas diffused into the second measurement chamber to be lowered sufficiently such as not to substantially decompose NOx thus allowing for correct measurement of the NOx gas concentration in an atmosphere which is only slightly affected by the residual oxygen.

The present inventors have completed the present invention based on the following formulation. First, the NOx gas concentration sensor by the NOx gas concentration sensor which preferably carries out the measurement method of the present invention, according to the JP Patent application 8-160812, filed by the present applicant (Assignee), is explained. There is proposed, in this earlier application, a sensor having two sets of solid-electrolyte oxygen ion pump cells, two sets of measurement chambers communicating with each other via a diffusion port extending along the stacked direction of the cells and an oxygen partial pressure sensor electrode for measuring the oxygen partial pressure in the first measurement chamber into which is introduced the gas under measurement via a diffusion port. With the sensor, oxygen is pumped out from the first measurement chamber by the first oxygen ion pump cell so that NOx is not decomposed in the first measurement chamber and so that the residual oxygen concentration will be lowered, whereas NOx is decomposed by the second oxygen ion pump cell and the current flowing in the second oxygen ion pump cell is measured for detecting the NOx gas concentration. With this sensor, if the electrode provided on the outer side of the second oxygen ion pump cell is exposed to the atmosphere under measurement, the first oxygen ion pump cell is controlled so that the potential of the oxygen partial pressure sensor electrode is 150 to 350 mV, while the voltage impressed across the second oxygen ion pump cell is set to 450 mV. It has turned out that, if the voltage impressed across the second oxygen ion pump cell is set in this manner, the NOx gas concentration cannot be measured accurately in case $H_2O$ is mixed into the NOx gas concentration sensor.

The present inventors have conducted further investigations and have found the followings: (1) If $H_2O$ comes into the NOx gas concentration sensor, the pump current flowing in the second oxygen ion pump cell is increased to render it impossible to make accurate measurement of the NOx concentration; (2) the amount of oxygen flowing the second oxygen ion pump cell is changed with the oxygen concentration in the second measurement chamber thus causing fluctuations in the offset; and (3) NOx decomposition characteristics are changed depending on the oxygen concentration in the atmosphere thus causing fluctuations in the gain. The offset is the value of Ip2 in case NO is not injected into the gas under measurement. It is desirable for the offset to be smaller in value. Moreover, it is desirable for the offset to be less sensitive to fluctuations in the extraneous influencing factors, such as the oxygen concentration or temperature, such that it can hardly be changed due to these fluctuations. In the present invention, the 'gain' means the difference in the second oxygen ion pump cell current Ip2 at a NO gas concentration of 0 ppm and that at a pre-set concentration (1000 ppm).

The present inventors also have made the following findings: (4) If the limiting current characteristics of the second oxygen ion pump cell are measured, the second ion pump cell voltage specifying the limit current area is significantly changed due to the presence of $H_2O$; (5) in this limit current area, there is a second ion pump cell voltage area in which the atmosphere oxygen concentration dependency is hardly observed; (6) although the $H_2O$ dissociation voltage is thought to be of the order of a few voltage, there is probability that the $H_2O$ dissociation voltage is lowered under a low oxygen concentration. That is, the dissociation voltage of NOx is approximately equal to that of $H_2O$ as an obstructive gas, so that there is a probability that the moisture plays a significant role in measurement of the NOx gas concentration.

In one aspect for the formation of the residual gas either in the flow channel or in the first flow channel, the voltage is applied preferably to an extent that does not substantially dissociate $H_2O$ and/or $CO_2$.

In a still further aspect, the residual gas is formed under the condition that allows and compensates for substantial decomposition of NO in the first flow channel or generally an upstream region in the flow channel. This condition is established such that the in-flowing NOx from the ambient gas compensates the decomposed amount of NO to bring an equilibrium state in the residual gas.

The NOx is understood to be substantially the sum of NO and an amount of $NO_2$ in an equilibrium determined generally by the temperature in which the rate of $NO_2$ decreases as the temperature rises. For example, at room temperature it is almost $NO_2$, at 300–400° C. 50/50 and at 700° C. or above $NO_2$ is 5% or less.

The sensor is preferably operated at about 700° C. or above and up to about 900° C. more preferably at 750–850° C.

Thus the role of $NO_2$ in $NO_x$ is relatively small or negligible under the carefully operated conditions, or $NO_2$ may be regarded as NO under certain conditions which will be explained later.

BRIEF DESCRIPTION OF THE DRAWINGS

FIGS. 36A to 36D illustrate a NOx gas concentration sensor according to the embodiment of the second and fourth aspect of the present invention, wherein FIG. 36A is a cross-sectional view for illustrating a NOx gas concentration sensor according to the embodiment of the second and fourth aspect of the present invention; FIG. 36B is a longitudinal cross-sectional view thereof; FIG. 36C is a schematic enlarged cross-sectional view of the first measurement chamber; and FIG. 36D is a plan view of the second measurement chamber.

FIGS. 42–48 show the test results of the embodiment of FIG. 41 as compared to a reference (control) example.

FIGS. 54A and 54B are plan views looking along the directions of arrows A and B in FIG. 1, wherein FIG. 54A illustrates a sensor of FIG. 53 and FIG. 54B illustrate modifications of the sensor shown in FIG. 53.

FIG. 61 shows the difference in the relationship between the effective Vp2 versus oxygen concentration in the measurement gas between the enclosed type and the exposed type of the measuring electrode.

FIGS. 62–69 show various embodiments of the sensor, both for enclosed type and exposed type of the measuring electrode.

FIGS. 67–70 are various variants of the embodiments of the present invention for selective measuring NOx concentration freed from interference by other gas components.

PREFERRED EMBODIMENTS

Figure 1:
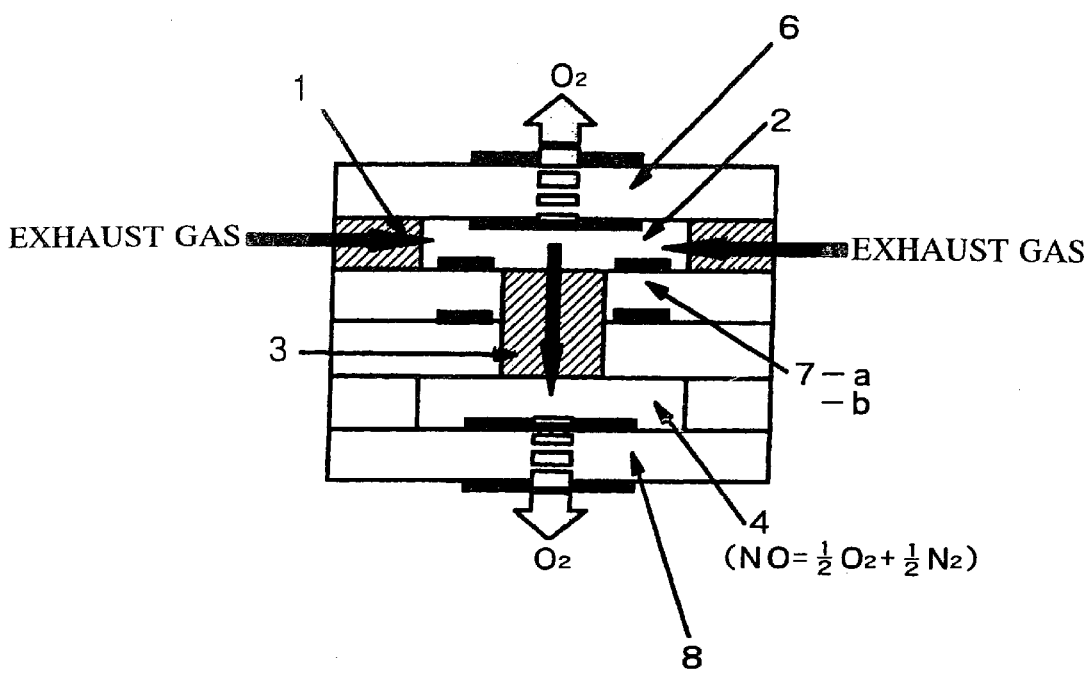
FIG. 1 schematically shows a NOx gas concentration sensor for illustrating the principle of the method for measuring the NOx gas concentration according to an embodiment of the third and fourth aspects of the present invention.

As an embodiment in the aspect (1-1), the flow channel is preferably provided in a ceramic body. However, a flow channel may also be annexed to the ceramic body. For example, a flow channel may be provided between the ceramic body and an insulating body so that the ceramic body will face the flow channel.

In the aspect 1-1, a diffusion resistance may be provided at or in an entrance to the flow channel for restricting the flow of the measurement gas. If the flow channel is divided into two chambers, a diffusion resistance may be provided in each flow channel entrance.

In the above aspect 2-1, an ammeter may be connected across the electrodes as measurement means for measuring the current flowing in the electrochemical body (the above-mentioned ceramic body). Alternatively, means for measuring an output, such as voltage converted from the current, corresponding to the intensity of the current. As means for determining the NOx concentration in the measurement gas based on the current (or an output corresponding to the current), a micro-computer may be used, which has a memory for storing the pre-set relation between the NOx concentration and the current which is pre-determined using a model gas having a known NOx gas concentration. The reference potential of the oxygen concentration reference electrode may be substantially enclosed in the ceramic body (preferably the electrode is designed as an oxygen-auto-generating electrode) and may be connected to atmosphere with a pre-set diffusion resistance via a porous electrically conductive lead for stabilizing the reference potential of the concentration reference electrode. The same holds for the electrode arranged outside of the flow channel for drawing out oxygen.

In particular, in the above aspects 2-2 or 2-3, the oxygen concentration gradient of the flowing direction of the measurement gas generated at the distal end of the electrode is lowered by shortening the electrode provided in the flow channel for drawing out oxygen, thus reducing the difference in the oxygen concentration along the direction that the electrode extends. Also, the electromotive force produced across the distal end of this electrode and the distal end of the counterpart electrode formed outside of the flow channel can be suppressed, as shown in the drawing. By suppressing the electromotive force in this manner, the voltage Vp1 impressed across these electrodes can be reduced thus reducing the temperature dependency and the oxygen concentration dependency proper to the measurement of the NOx gas concentration. In addition, with the above aspect 2-2 or 2-3, if the sensor is mounted in an exhaust system of an internal combustion engine driven in the vicinity of the lean area or the stoichiometric point, the NOx gas concentration detection output is stabilized even in case of the lean-rich switching, that is in case of acute change in the oxygen concentration in the exhaust gas.

Referring to the drawings, an embodiment of the present invention is explained in detail. First, the principle of the method for measuring the NOx gas concentration according to an embodiment of the third and fourth aspects of the present invention is explained. A sensor of FIG. 1, showing a schematic structure of a NOx gas concentration sensor for illustrating the above principle, includes a layer of a first oxygen ion pump cell 6, made up of a solid electrolyte layer and a pair of electrodes provided on both sides of the solid electrolyte layer, a layer of oxygen concentration measurement cell having a solid electrolyte layer and oxygen partial pressure sensor electrodes 7-a, 7-b provided on both sides of the solid electrolyte layer, and a second oxygen ion pump cell 8 having a solid electrolyte layer and oxygen ion pump electrodes provided on both sides of the solid electrolyte layer, laminated in this order. Between the first oxygen ion pump cell 6 and the layer of the oxygen concentration measurement cell is defined a first measurement chamber 2 by left and right side insulating layers and upper and lower solid electrolyte layers in the figure, whereas a second measurement chamber 4 is defined on top of the second oxygen ion pump cell 8. In the first measurement chamber 2 are formed a first diffusion hole 1 and a second diffusion hole 3, in separation from each other, for introducing the measurement gas via a diffusion resistance. The second diffusion hole 3 is passed through the layer of the oxygen concentration measurement cell 7 and the solid electrolyte layer for establishing communication between the first and second measurement chambers 2 and 4 for forwarding a gas containing at least NOx and $O_2$ from the first measurement chamber 2 via the diffusion resistance to the second measurement chamber 4.

The operation of the NOx gas sensor shown in FIG. 1 is explained in connection with an instance of measuring the NOx concentration in the exhaust gases. (a) First, the exhaust gas flows via first diffusion hole 1 into the first measurement chamber 2. (b) The oxygen in the exhaust gas flowing into the first measurement chamber 2 is pumped out such as substantially not to decompose NOx ($2NO \rightarrow N_2 + O_2$). At this time, the first oxygen ion pump cell 6 is driven on the basis of an output signal of the oxygen partial pressure sensor electrodes 7-a, 7-b for controlling the oxygen partial pressure in the first measurement chamber 2 to a constant value. (c) The $O_2$ gas controlled in the concentration and the NOx gas (concentrated gas) flow form the first measurement chamber 2 via second diffusion hole 3 into the second measurement chamber 4. (d) Since the oxygen contained in the second measurement chamber 4 is pumped out by the second oxygen ion pump cell 8 to lower the oxygen concentration in the second measurement chamber 4 to decompose the NOx gas in the second measurement chamber 4 into $N_2$ and $O_2$ by the catalytic action proper to the electrode. Since there is a linear correlation between the value of the ion current Ip2 flowing in the second oxygen ion pump cell 8 and the NOx gas concentration, the NOx gas concentration can ultimately be measured by measuring the value of the current Ip2 thus enabling measurement of the NOx gas concentration in the exhaust gas. In this NOx gas concentration sensor, there is no leak current flowing between the electrodes by providing the oxygen partial pressure detecting electrode and the oxygen ion pump electrode in the different solid electrolyte layers. Thus, the residual oxygen concentration in the first measurement chamber 2 can be measured more accurately enabling correct detection of the NOx gas concentration on the basis of the oxygen derived from NOx decomposition.

If, in the sensor in which the electrode of the second oxygen ion pump cell 8 provided outside the second measurement chamber 4 is exposed to the atmosphere under measurement, the voltage applied across the second oxygen ion pump cell 8 is less than 300 mV, the amount of decomposed NO gas is decreased to lower the pump current Ip2 generated on decomposition, thus the NO gas measurement tending to be lowered in accuracy. If Vp2 exceeds 400 mV, $H_2O$ dissociation and decomposition start on the electrode of the second oxygen ion pump cell 8. Thus the pump current Ip2 tends to be increased due to $O_2$ generated on dissociation to lower the NO gas measurement accuracy. Therefore, the voltage applied across the second oxygen ion pump cell 8 is preferably 300 to 400 mV, more preferably 320 to 380 mV and most preferably 330 to 370 mV or 350 mV or thereabouts. In the present invention, the numerical limitation encompasses not only upper and lower limit values but also any intermediate values.

In a sensor in which the second oxygen ion pump cell 8 provided outside the second measurement chamber 4 is not exposed to the atmosphere being measured, the voltage impressed across the second oxygen ion pump cell 8 is preferably 400 to 500 mV, more preferably 420 to 480 mV and most preferably 430 to 470 mV or 450 mV or thereabouts for the same reason.

Preferably, the measurement method of the present invention is used in a sensor in which the first oxygen ion pump cell, the oxygen concentration measurement cell and the second oxygen ion pump cell are provided in respective different electrode layers. More preferably, an insulating layer formed of, for example, alumina etc., is layered between these cells for preventing leak current from flowing in the electrodes provided in these cells. Also preferably, a heating layer is provided for maintaining a constant temperature of the oxygen concentration measurement cell for raising the temperature in the second measurement chamber.

As the solid electrolyte, a zirconia-yttria solid solution or a zirconia-calcia solid solution may be used. The porous electrodes formed by screen printing or firing on both sides of the thin-plate-shaped solid electrolyte are preferably formed of platinum or rhodium or alloys thereof, such as platinum or rhodium alloys having a catalyst action. The first and second diffusion holes (gas diffusion means or gas diffusion channels) are preferably formed using porous ceramics exemplified by porous alumina ceramics. The heating part of the heater is preferably formed by a compound material of ceramics and platinum or platinum alloys, with lead portions being preferably of platinum or platinum alloys.

The measurement method of the present invention can be applied to CO gas sensor or $CO_2$ gas sensors, in which case the effects of $H_2O$ can be lowered such that the concentration of the gas being measured can be measured accurately. Other desirable features are as described in the JP Patent Application No. 8-160812 filed in the name of the present applicant (or Assignee). As the occasion may demand this application is incorporated into the present specification by reference thereto.

DETAILED DESCRIPTION OF THE PREFERRED EMBODIMENTS

Referring to the drawings, preferred embodiments of the present invention will be explained in detail.

Figure 2:
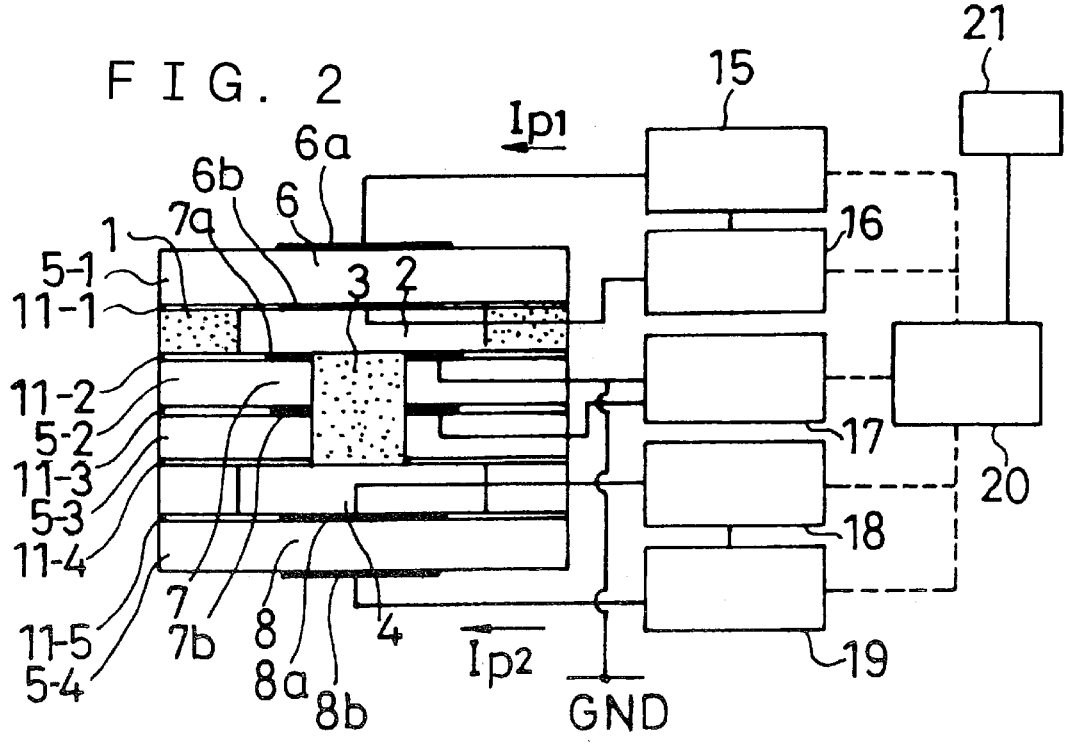
FIG. 2 illustrates a NOx gas concentration sensor according to the embodiment of the third and fourth aspects of the present invention.

FIG. 2 shows a cross-sectional view for illustrating a schematic structure of a NOx gas concentration sensor used for measuring the NOx gas concentration according to the present invention. The sensor of FIG. 2 includes a solid electrolyte layer 5-1, a layer of the first oxygen ion pump cell 6 having an electrode 6a (positive electrode) and an electrode (negative electrode) 6b provided on both sides of the layer 5-1, a solid electrolytic layer 5-2, a layer of the oxygen concentration measurement cell 7 having oxygen partial pressure sensor electrodes 7a, 7b provided on both sides of the layer 5-2, a solid electrolyte layer 5-3, and a layer of the second oxygen ion pump cell 8 having a solid electrolyte layer 5-4 oxygen ion pump electrodes 8a, 8b provided on both sides of the solid electrolyte layer 5-4, layered (laminated) in this order. Between the first oxygen ion pump cell 6 and the layer of the oxygen concentration measurement cell 7 is defined a first measurement chamber 2 by left and right side insulating layers and upper and lower solid electrolyte layers in the figure, whereas a second measurement chamber 4 is defined above and facing the second oxygen ion pump cell 8. In the first measurement chamber 2 are formed a first diffusion hole 1 and a second diffusion hole 3, in separation from each other, for introducing the measurement gas via a diffusion resistance. The second diffusion hole 3 is passed through the layer of the oxygen concentration measurement cell 7 and the solid electrolyte layer 5-3 for establishing communication between the first and second measurement chambers 2 and 4 for forwarding a gas containing at least NOx and $O_2$ from the first measurement chamber 2 via diffusion resistance to the second measurement chamber 4. Thus a flow channel is established.

Between the respective layers are formed dense insulating layers 11-1, ..., 11-5 of alumina. The heating layer adapted for heating the sensor is bonded to the cells, via cement layers, on the outer layers of the first and second oxygen ion pump cells 6, 8 for sandwiching the entire sensor in the layering (stacking) direction. The electrodes 6a, 6b, 7a, 7b, 8a and 8b are connected via leads to power source means (voltage impressing means), voltage measurement means and to the current measurement means, which will be explained subsequently.

In the present sensor, the first measurement chamber 2 and the second measurement chamber 4 are vertically superposed together. The first diffusion hole 1 is disposed on both sides of the sensor, while there is no porous material charged in the second diffusion hole. An insulating layer is arranged between all solid electrolyte layers, with the electrodes of the cells being insulated from one another. A porous material can be charged into the second measurement chamber 4.

To this sensor is annexed a micro-computer 20 having a power source unit 15 and an ammeter 16 of a first oxygen ion pump cell 6, a potentiometer 17 of the oxygen concentration measurement cell 7, a power source unit 19, an ammeter 18 and a recorder 21 of the second oxygen ion pump cell 8. The reference oxygen concentration, measured by the oxygen concentration measurement cell 7, is set by the fact that the electrode 7b and its lead line are porous so that there is established communication with outside air via a pre-set diffusion resistance. If a pre-set minor current is allowed to flow in the oxygen concentration measurement cell 7, the electrode 7b may be used as a auto-generating reference pole. The merit of this auto-generating reference pole is that the reference oxygen concentration is less susceptible to changes in oxygen concentration in air.

Figure 3:
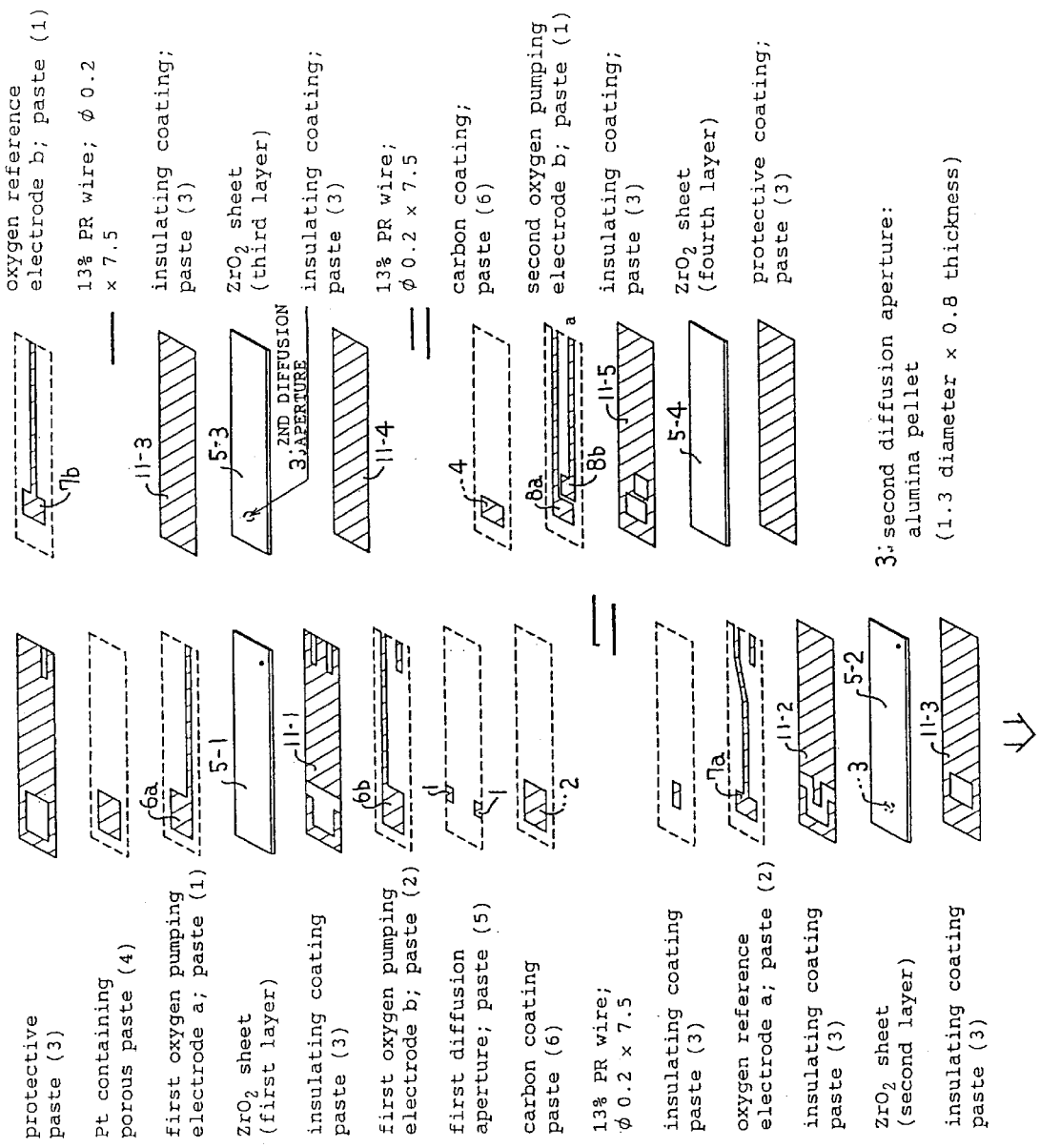
FIG. 3 shows a layout a manufacturing example and the structure of a NOx gas concentration sensor according to third and fourth aspects of the embodiment of the present invention.

An example of fabrication of the $ZrO_2$ sheeting and the layout of the NOx concentration sensor used in the measurement tests, as later explained, is hereinafter explained. In the measurement tests, as later explained in connection with Tables 1 to 5 (test examples 1 to 25) and the results of measurement 1 to 14, a type 1 sensor, in which an outer electrode of the second oxygen ion pump cell is not coated, is used. The results of measurement, obtained using a coated type 2 sensor, are shown last. FIG. 3 shows the layout of the type 2 sensor. The layout of the type 1 sensor is similar to the type 2 except the structure of the vicinity of the second oxygen ion pump cell and the layout shown in FIG. 3 and is prepared similarly to that of the type 1 sensor.

Referring to FIG. 3, a $ZrO_2$ sheet and a paste for an electrode are layered from upper left to lower left and from upper right to lower right to form a unitary sensor. The paste materials, such as an insulating coating or an electrode, are layered by screen printing on a pre-set $ZrO_2$ sheet. Manufacturing examples of component parts, such as $ZrO_2$ sheets, shown in FIG. 3, are hereinafter explained.

Molding $ZrO_2$ Sheets $ZrO_2$ powders were calcined in an atmospheric furnace at 600° C. for 2 hours. 30 kgs of calcined $ZrO_2$ powders were weighed and mixed together in a trammel together with 150 g of dispersants, 10 kgs of an organic solvent, and 60 kgs of balls. The resulting mass was mixed together and dispersed for approximately 50 hours and added to with 4 kgs of a binder dissolved in 10 kgs of the organic solvent. The resulting mixture was mixed together for 20 hours to give a slurry having a viscosity of approximately 10 Pa·s. From this slurry, a $ZrO_2$ green sheet was prepared by a doctor blade method and dried at 100° C. for one hour.

Paste for Printing (1) For a first oxygen ion pump a, an oxygen partial pressure detecting electrode (oxygen reference electrode) a and for second oxygen ion pump sensors a and b: 20 gs of platinum powders, 2.8 gs of $ZrO_2$ and a moderate amount of an organic solvent were concocted together in a crusher or a pot mill and mixed for four hours for dispersion. The resulting mass was added to with 2 gs of a binder dissolved in 20 gs of the organic solvent. The resulting mass was further added to with 5 gs of a viscosity controller and mixed for four hours to a paste having the viscosity on the order of 150 Pa·s.

(2) For a first oxygen ion pump b and an oxygen partial pressure detecting electrode (oxygen reference electrode) b: 19.8 gs of platinum powders, 2.8 gs of $ZrO_2$, 0.2 gs of gold powders and a moderate amount of an organic solvent were concocted together in a crusher or a pot mill and mixed for four hours for dispersion. The resulting mass was added to with 2 gs of a binder dissolved in 20 gs of an organic solvent. The resulting mass was further added to with 5 gs of a viscosity controller and mixed for four hours to a paste having the viscosity on the order of 150 Pa·s.

(3) For insulating coating and protective coating: 50 gs of alumina powders and a moderate amount of an organic solvent were concocted together in a crusher or a pot mill and mixed together for 12 hours for dissolution. The resulting solution was added to with 20 gs of the viscosity controller and mixed for three hours to give a paste with a viscosity on the order of 100 Pa·s.

(4) For Pl-containing porous components (lead lines): 10 gs of alumina powders, 1.5 gs of platinum powders, 2.5 gs of a binder and a moderate amount of an organic solvent were concocted together in a crusher or a pot mill and mixed together for 4 hours for dissolution. The resulting solution was added to with 10 gs of the viscosity controller and mixed for four hours to give a paste with a viscosity on the order of 100 Pa·s.

(5) For first diffusion hole: 10 gs of alumina powders with a mean particle size of 2 μm, 2 gs of a binder and 20 gs of an organic solvent were concocted together in a crusher (pot mill) and mixed together for dispersion. The resulting mass was added to with 10 gs of a viscosity controller and mixed for 4 hours to give a paste with a viscosity of 400 Pa·s.

(6) For carbon coating: 4 gs of carbon powders, 2 gs of a binder and 40 gs of an organic solvent were concocted together by a crusher or a pot mill and mixed together for dispersion. The resulting mass was added to with 5 gs of a viscosity controller and mixed together for 4 hours to give a paste. By printing a carbon coating, it becomes possible to prevent the first oxygen pump electrode b from being contacted with the oxygen reference electrode. The carbon coating is used for forming the first measurement chamber and the second measurement chamber. The carbon coating is also used for forming the first and second measurement chambers. Since carbon is burned off during firing, there is no carbon coating layer in the sintered mass.

Pellets

For second diffusion hole 20 gs of alumina powders, with a particle size of approximately 2 μm, were concocted with 8 gs of a binder and 20 gs of an organic solvent in a crusher (or a pot-mill). The resulting mass was mixed for one hour, granulated and pressed with a metal mold press at a pressure of approximately 2 t/cm² to form a press-molded product ϕ1.3×0.8t mm of a columnar shape (green state). The pres-molded article in the green state was inserted in a pre-set position in second and third layers of the zirconia green sheets and pressed together to a unitary product which was then fired to form a second diffusion hole in a sensor.

Method for Laminating $ZrO_2$

After pressure bonding of the second and third layers, the molded product was punched at a portion in which the second diffusion hole (ϕ1.3 mm) is to be formed. After punching, a columnar-shaped green molded product which should prove to be the second diffusion hole is buried in the punched portion and the first to fourth layers of the $ZrO_2$ sheet is pressure-bonded under a pressure of 5 kg/cm² and for pressing time of one minute.

Removing Organic Ingredient and Firing

The press-bonded molded product was subjected to removal of organic ingredients at 400° C. for two hours and fired at 1500° C. for one hour.

The size of the sensor used in a measurement tet as later explained is now explained. The outer shape of the sensor is such that its longitudinal length is 50 mm, its width (short side length) is 4 mm and its thickness length in the layering direction) is 1.3 mm. The thickness of the first oxygen ion pump cell is 0.35 mm, with the resistance being 40 to 60 ohms for the temperature of the pump cell of approximately 800° C. The thickness of the second oxygen ion pump cell is 0.35 mm, with a resistance being 40 to 60 ohms for a temperature of the pump cell of approximately 800° C. The longudinal length of the electrode of the first oxygen ion pump cell 6 along the length of the electrode is 7 mm, with its short side length being 2 mm. The longitudinal length of the electrode of the second oxygen ion pump cell 8 along the length of the electrode is 7 mm, with its short side length being 2 mm. The longitudinal length of the electrode of the oxygen partial pressure detection electrodes 7a, 7b along the length of the electrodes is 2 mm, with the short side length thereof being 2 mm. The electrodes are all 10 to 20 μm, with the height of the first and second measurement chambers being about several tens of micrometers (of the order of 50 μm).

Tables 1 to 5 show the measured results employing a NOx gas concentration sensor in which an external electrode of the second oxygen ion pump cell is exposed to a measurement atmosphere. FIGS. 4 to 17 show the results of measurement put into order. The common measurement conditions for test examples are the exhaust gas (measurement gas) temperature of 300° C. and the heater power of 20 W. The heater of 20 W corresponded to the sensor temperature of 800° C.

Refer to TABLE 1.
Refer to TABLE 2.
Refer to TABLE 3.
Refer to TABLE 4.
Refer to TABLE 5.

Results of Measurement 1

Figure 4:
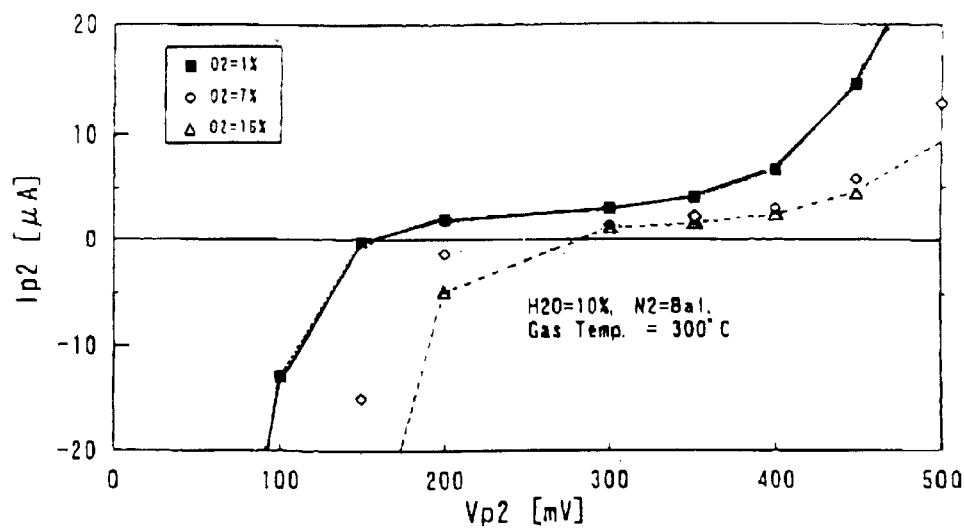
FIG. 4 is a graph showing the relation between the current Ip2 flowing in and the voltage Vp2 applied to the second oxygen ion pump cell, which holds when the oxygen concentration is changed, according to the third and fourth aspects of the embodiment of the present invention.

The voltage of the oxygen partial pressure detection electrode was set to 350 mV. FIG. 4 showing the test examples 4 to 6 in a graph shows the relation between the second ion pump cell current Ip2 and the voltage Vp2 impressed across the second ion pump cell when the oxygen concentration is varied. It is seen that, with the second oxygen ion pump cell voltage Vp2 of not higher than 400 mV, the value of Ip2, that is the Ip2 offset, is small, the variation of Ip2 for the variation of the oxygen concentration is smaller and the oxygen concentration dependency of Ip2 is lowered.

Result of Measurement 2

Figure 5:
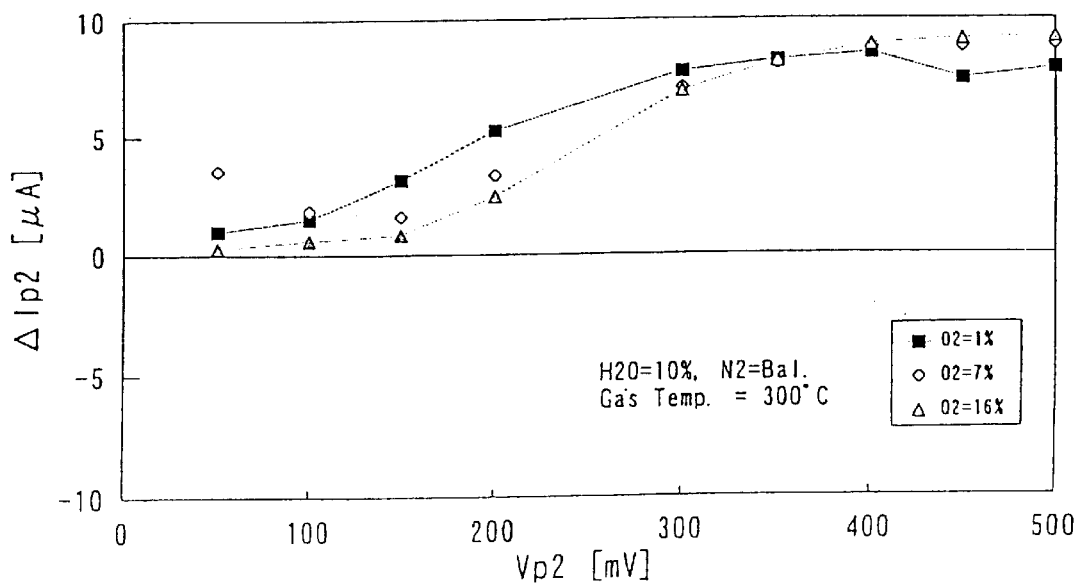
FIG. 5 is a graph showing the relation between the gain of the current Ip2 flowing in and the voltage Vp2 applied to the second oxygen ion pump cell, which holds when the oxygen concentration is changed, according to third and fourth aspects of the embodiment of the present invention.

The voltage of the oxygen partial pressure sensing electrode was set at 350 mV. FIG. 5, showing the relation with Vp2 of the difference between a test example 7 and test example 4, that between a test example 8 and test example 5, and that difference between a test example 9 and test example 6, shows the relation between the gain of the second oxygen ion pump cell current Ip2 and the voltage Vp2 impressed across the cell in case the oxygen concentration is changed. It is seen that, with the voltage Vp2 applied across the second oxygen ion pump cell being 300 to 400 mV, the gain variation of the current Ip2 relative to the variation of the oxygen concentration is small thus lowering the oxygen concentration dependency of the Ip2 gain.

Results of Measurement 3

Figure 6:
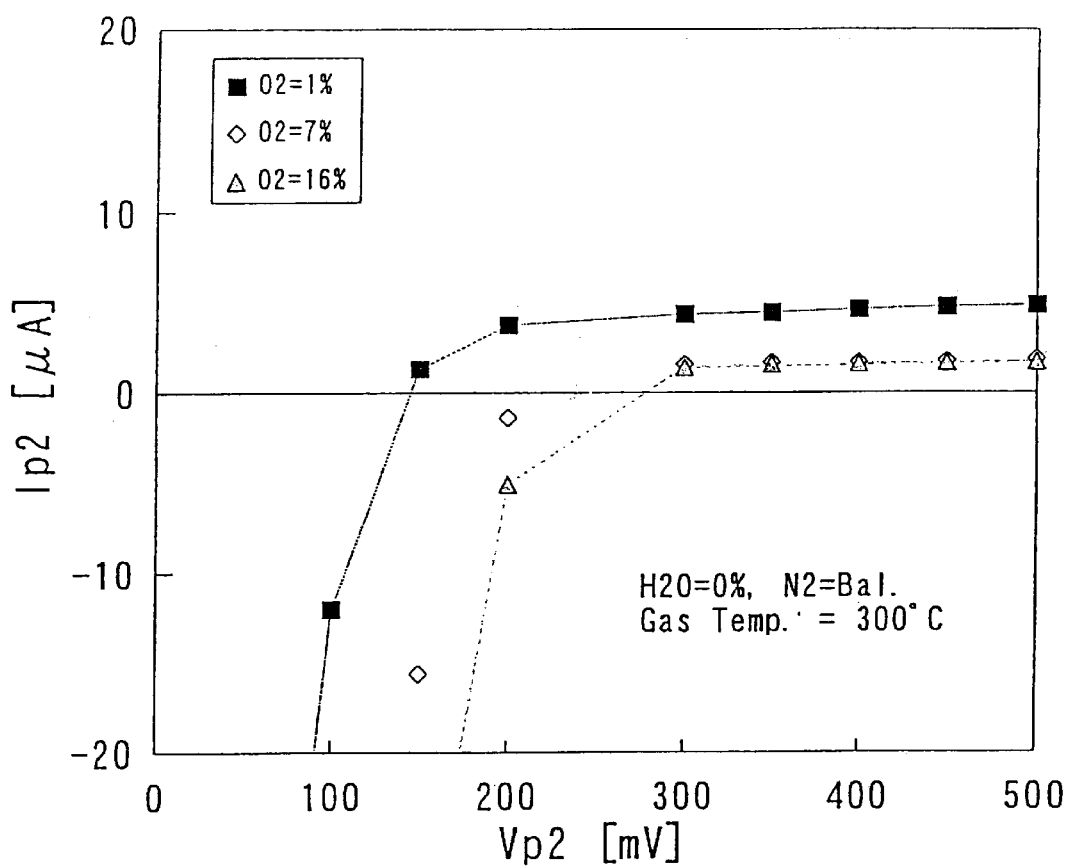
FIG. 6 shows a graph showing, similarly to FIG. 4, the relation between the current Ip2 flowing in and the voltage Vp2 applied to the second oxygen ion pump cell, which holds when the oxygen concentration is changed, according to the third and fourth aspects of the embodiment of the embodiment of the present invention.

The voltage of the oxygen partial pressure sensor electrode was set at 350 mV. FIG. 6, showing the test examples 1 to 3 as a graph, shows the relation between the second oxygen ion pump cell current Ip2 and the voltage Vp2 applied across the cell. It is seen that, with the voltage Vp2 applied across the second oxygen ion pump cell, the variation of Ip2 with respect to variation in the oxygen concentration and Vp2 is small.

Results of Measurement 4

Figure 7:
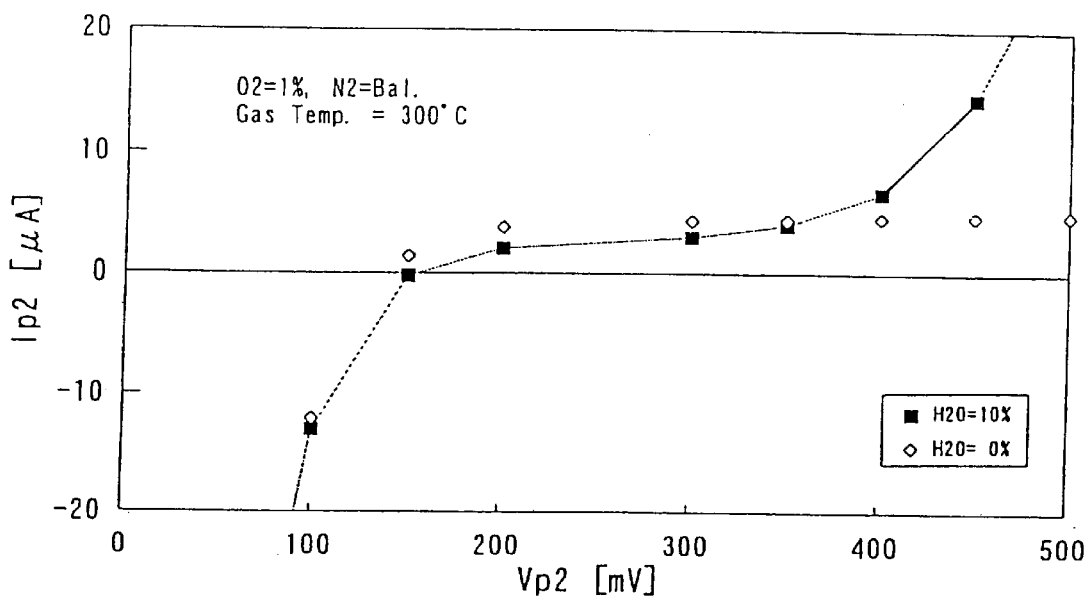
FIG. 7 is a graph showing the relation between the second oxygen ion pump cell current Ip2 and the voltage applied across the same cell, when the moisture amount is changed, according to the embodiment of the third and fourth aspects of the present invention.

The voltage of the oxygen partial pressure detection electrode was set to 350 mV. FIG. 7 showing the test examples 1 to 4 in a graph shows the relation between the second ion pump cell current Ip2 and the voltage Vp2 impressed across the second ion pump cell was 300 to 400 mV when the oxygen concentration is varied. It is seen that, with the second oxygen ion pump cell voltage Vp2 of 300 to 400 mV, the variation of Ip2, that is the Ip2 offset, is small, whilst the Ip2 variation relative to the variation in the moisture is small. Thus indicating that the moisture dependency of Ip2 is lowered to lower the Vp2 dependency of Ip2, too.

Result of Measurement 5

Figure 8:
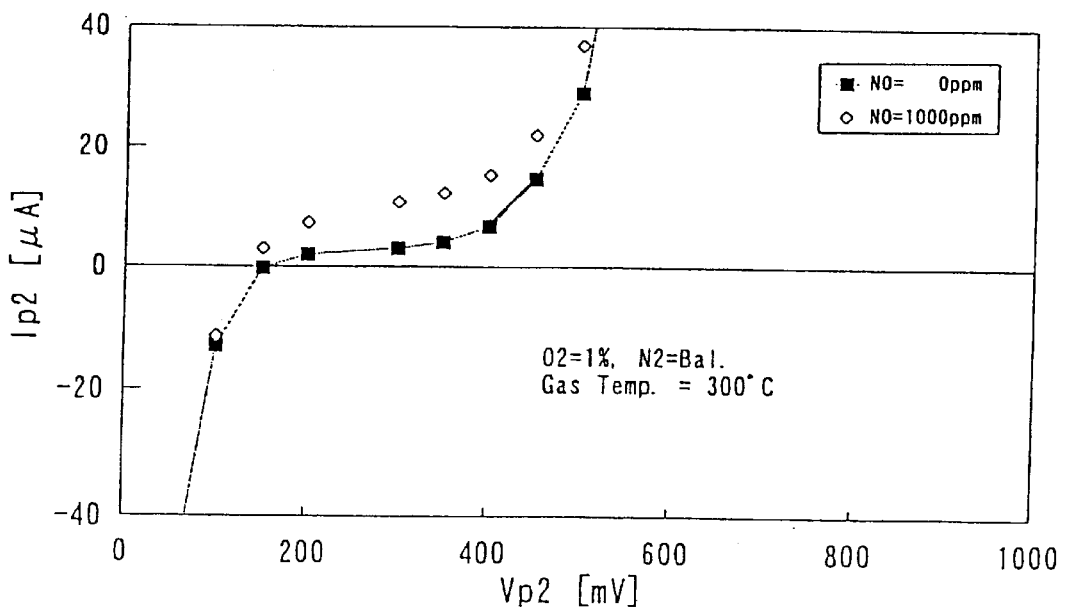
FIG. 8 is a graph showing the relation between the second oxygen ion pump cell current Ip2 and the voltage Vp2 applied across the same cell, when the NOx concentration is changed, according to the embodiment of the third and fourth aspects of the present invention.

The voltage of the oxygen partial pressure sensor electrode was set to 350 mV. FIG. 8, showing testing example 4 and 7 in a graph, shows the relation between the second oxygen ion pump cell current Ip2 and the voltage Vp2 applied across the cell when the NO gas concentration is changed. It is seen that, with the second oxygen ion pump cell voltage Vp2 of 300 to 400 mV, the variation of Ip2 relative to the variation of the NO gas concentration is large thus enabling correct measurement of the NOx gas concentration.

Summary of Results of Measurement 6 and 7; O2=1% and Vs=350 mV

Figure 9:
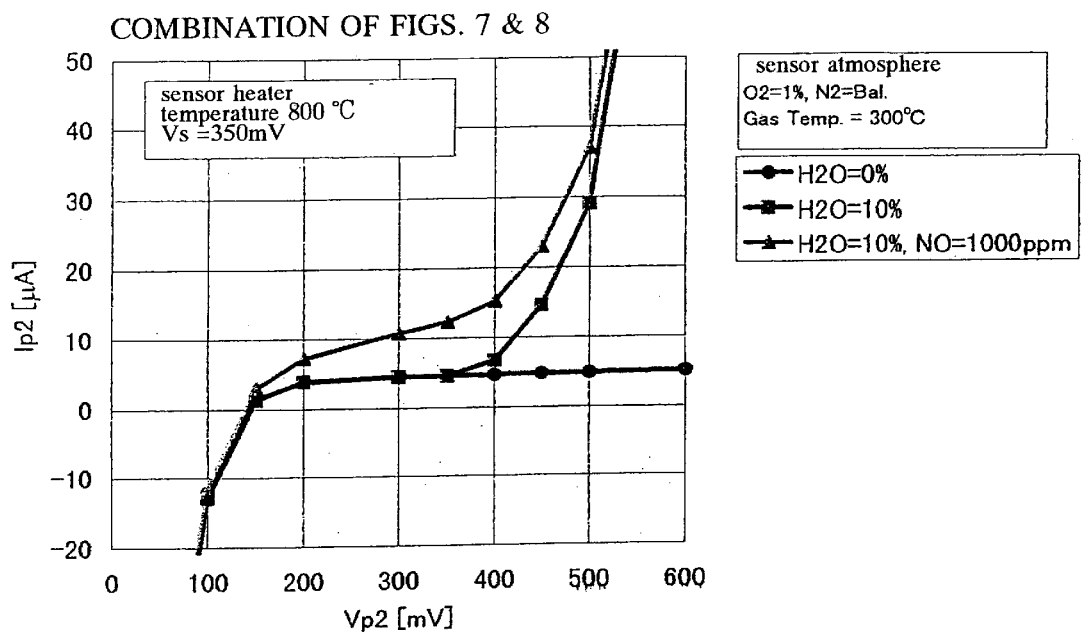
FIG. 9 is a combined graph showing the results of FIGS. 7 and 8.

FIG. 9 collectively shows the results shown in FIGS. 7 and 8. Although data plotted in FIG. 9 have been obtained under the same measurement conditions as those for data shown in FIGS. 7 and 8, there is a slight difference between the two data values due to measurement errors. It is seen from FIG. 9 that, if VP2 is set to not higher than 400 mV (pre-set voltage), the $H_2O$ concentration dependency of the difference between IP2 for $H_2O$ of 0% and that for $H_2O$ of 10%, that is a detector output, is relatively small. It is also seen from FIG. 9 that, if VP2 is set to not larger than 400 mV (pre-set voltage), the difference in IP2 for NO of 0 ppm and that for NO of 1000 ppm, with the $H_2O$ concentration being 10% becomes larger.

Results of Measurement 6

Figure 10:
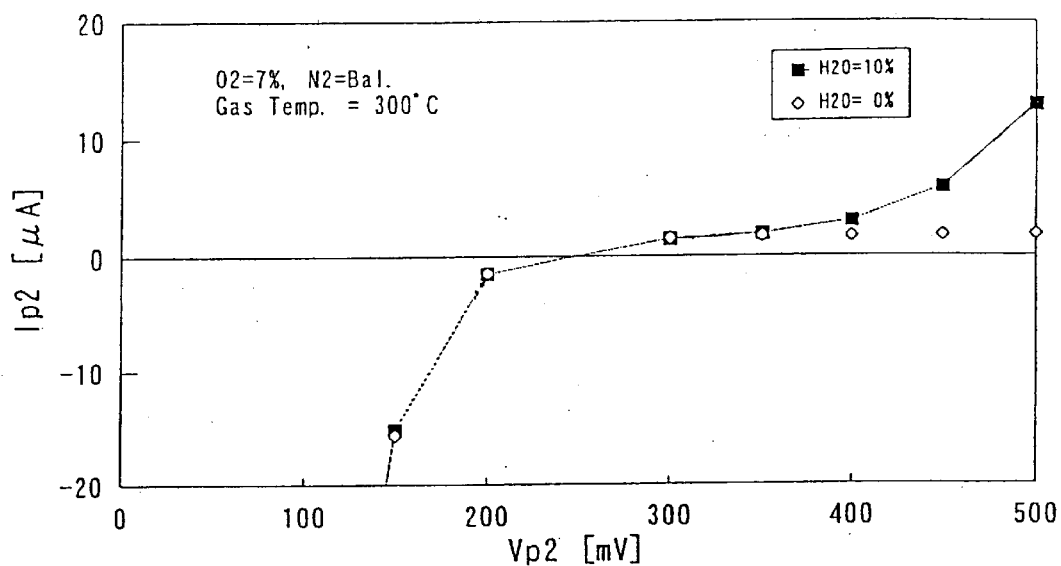
FIG. 10 is a graph showing, similarly to FIG. 7, the relation between the second oxygen ion pump cell current Ip2 and the voltage Vp2 applied across the same cell, when the moisture amount is changed, according to the embodiment of the third and fourth aspects of the present invention.

The voltage of the oxygen partial pressure detection electrode was set to 350 mV. FIG. 10 showing the test examples 2 and 5 shows the relation between the second oxygen ion pump cell current Ip2 and the voltage Vp2 applied across the cell when the amount of the moisture is changed. It is seen that, with the voltage Vp2 applied across the second oxygen ion pump cell not higher than 400 mV, the value of Ip2, that is Ip2 offset, is lowered, and that the variation of Ip2 relative to the variation of the amount of the moisture is only small, with the moisture amount dependency of Ip2 being low.

Result of Measurement 7

Figure 11:
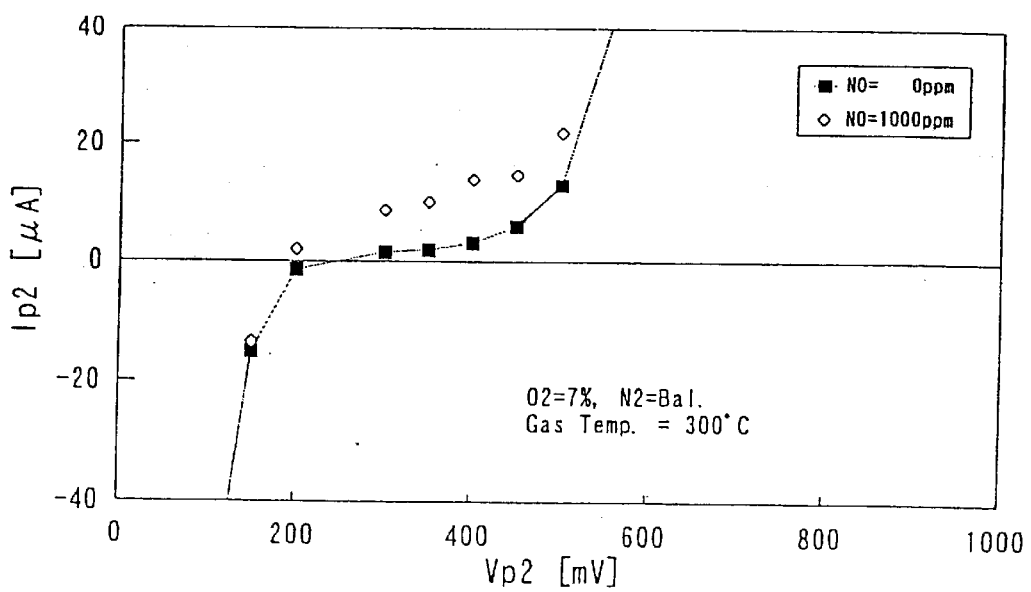
FIG. 11 is a graph showing, similarly to FIG. 8, the relation between the second oxygen ion pump cell current Ip2 and the voltage Vp2 applied across the same cell, when the NOx concentration is changed, according to the embodiment of the third and fourth aspects of the present invention.

The voltage of the oxygen partial pressure sensor electrode was set to 350 mV. FIG. 11, showing test examples 5 and 8 in a graph, shows the relation between the second oxygen ion pump cell current Ip2 and the voltage Vp2 applied across the cell when the NO gas concentration is changed. It is seen that, with the second oxygen ion pump cell voltage Vp2 not higher than 400 mV, the variation of Ip2 relative to the variation of the NO gas concentration is large thus enabling correct measurement of the NOx gas concentration.

Summary of Results of Measurement 8 and 9; O2=7% and Vs=350 mV

Figure 12:
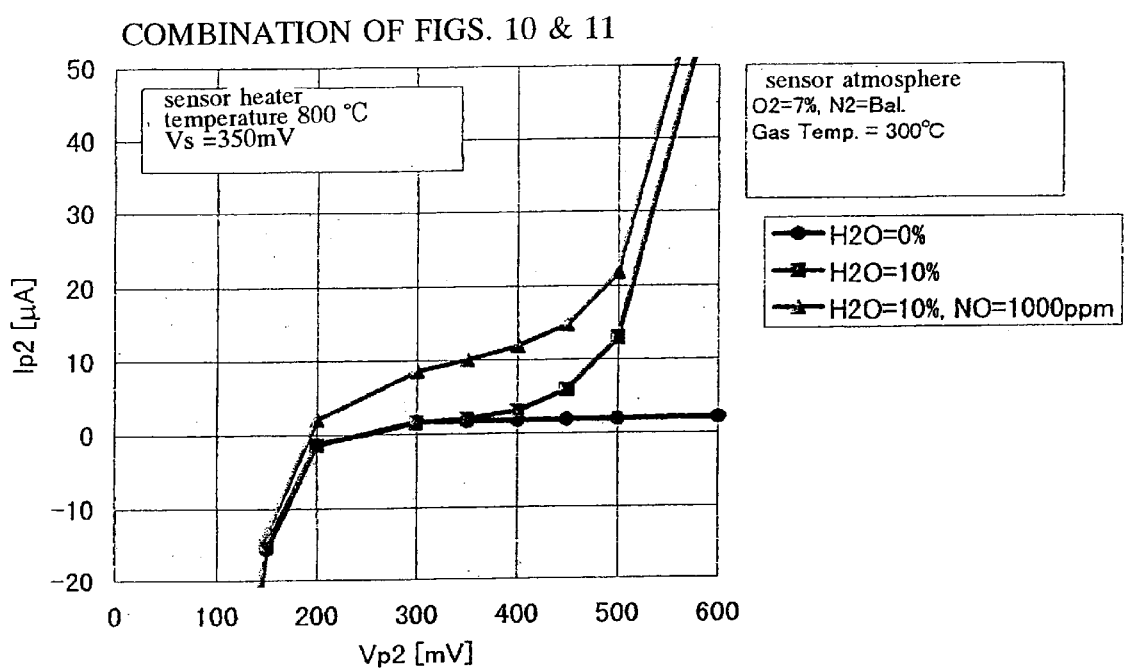
FIG. 12 is a combined graph showing the results of FIGS. 10 and 11.

FIG. 12 collectively shows the results shown in FIGS. 10 and 11. It is seen from FIG. 12 that, if VP2 is set to not higher than 400 mV (pre-set voltage), the $H_2O$ concentration dependency of the difference between IP2 for $H_2O$ of 0% and that for $H_2O$ of 10%, that is a detector output, is relatively small. It is also seen from FIG. 9 that, if VP2 is set to not larger than 400 mV (pre-set voltage), the difference in IP2 for NO of 0 ppm and that for NO of 1000 ppm, with the $H_2O$ concentration being 10%, becomes larger.

Results of Measurement 8

Figure 13:
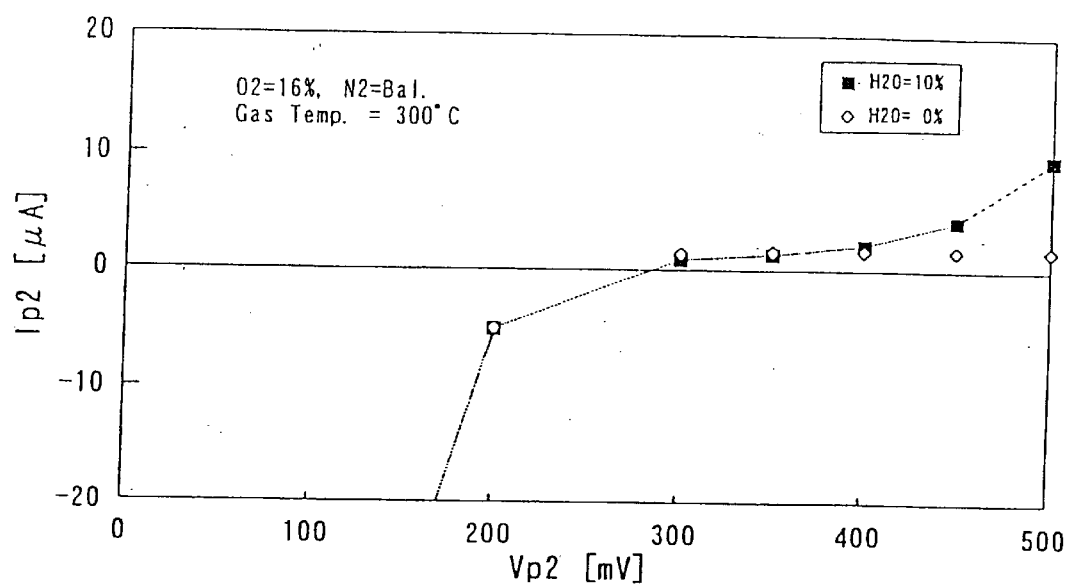
FIG. 13 is a graph showing, similarly to FIGS. 7 and 10, the relation between the second oxygen ion pump cell current Ip2 and the voltage applied across the same cell, when the moisture amount is changed, according to the embodiment of the third and fourth aspects of the present invention.

The voltage of the oxygen partial pressure detection electrode was set to 350 mV. FIG. 13 showing the test examples 3 and 6 shows the relation between the second oxygen ion pump cell current Ip2 and the voltage Vp2 applied across the cell when the oxygen concentration is changed. It is seen that, with the voltage Vp2 applied across the second oxygen ion pump cell of 300 to 400 mV, the value of Ip2, that is Ip2 offset, is lowered, and that the variation of Ip2 to the variation of the amount of the moisture is only small such that the moisture amount dependency of Ip2 is low.

Result of Measurement 9

Figure 14:
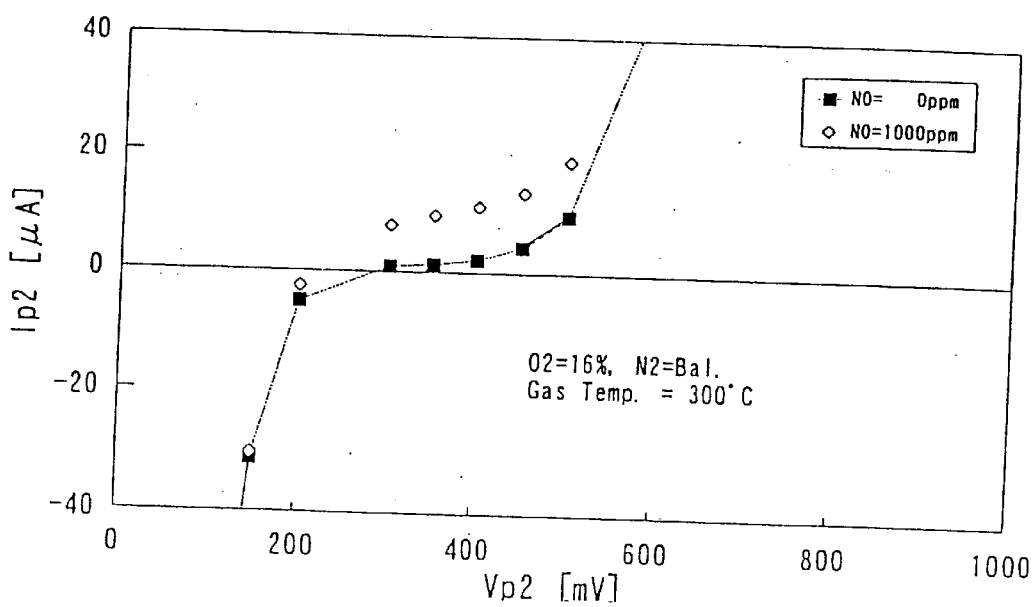
FIG. 14 is a graph showing, similarly to FIGS. 8 and 11, the relation between the second oxygen ion pump cell current Ip2 and the voltage applied across the same cell, when the NOx concentration is changed, according to the embodiment of the third and fourth aspects of the present invention.

The voltage of the oxygen partial pressure sensor electrode was set to 350 mV. FIG. 14, showing test examples 6 and 9 in a graph, shows the relation between the second oxygen ion pump cell current Ip2 and the voltage Vp2 applied across the cell when the NO concentration is changed. It is seen that, with the second oxygen ion pump cell voltage Vp2 not higher than 450 mV, the variation of Ip2 relative to the variation of the NO gas concentration is large thus enabling correct measurement of the NOx gas concentration.

Summary of Results of Measurement 10 and 11; O2=16% and Vs=350 mV

Figure 15:
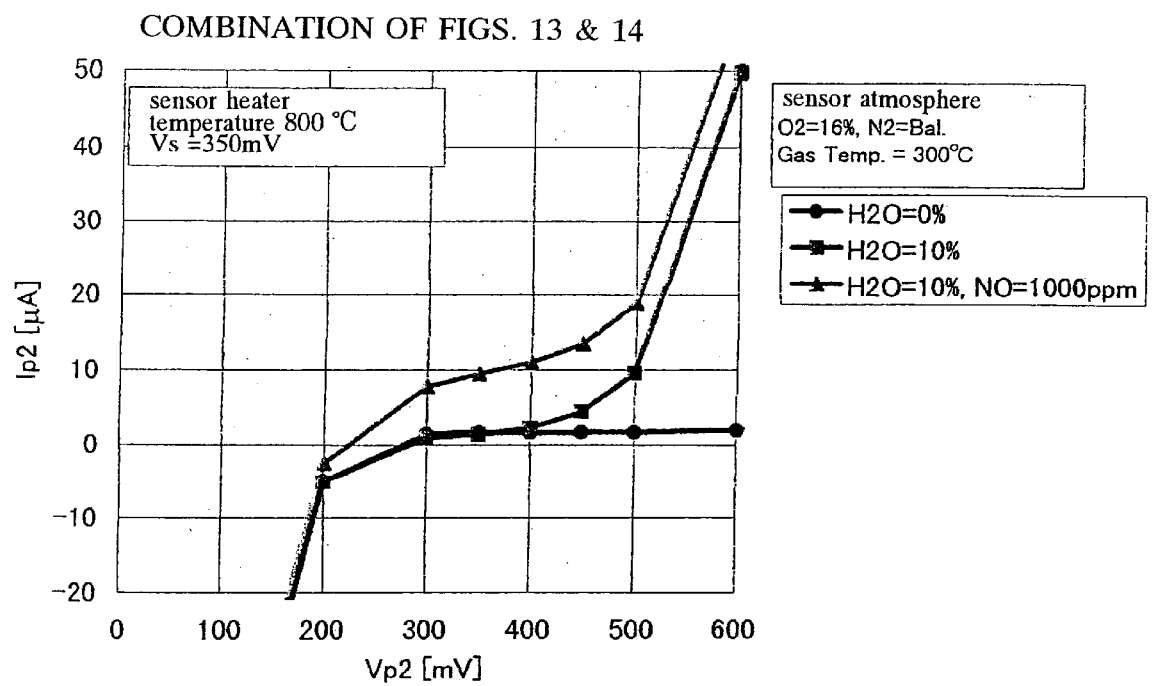
FIG. 15 is a combined graph showing the results of FIGS. 13 and 14.

FIG. 15 collectively shows the results shown in FIGS. 13 and 14. It is seen from FIG. 15 that, if VP2 is set to not higher than 400 mV (pre-set voltage), the $H_2O$ concentration dependency of the difference between IP2 for $H_2O$ of 0% and that for $H_2O$ of 10%, that is a detector output, is relatively small. It is also seen from FIG. 9 that, if VP2 is set to not larger than 400 mV (pre-set voltage), the difference in IP2 for NO of 0 ppm and that for NO of 1000 ppm, with the $H_2O$ concentration being 10%, becomes larger. It is also seen from FIGS. 9, 12 and 15 that, if the oxygen concentration of 0, 7 and 16% is changed, curves obtained on plotting respective data are similar to one another thus indicating that a detector output exhibits only little oxygen dependency.

Results of Measurement 10

Figure 16:
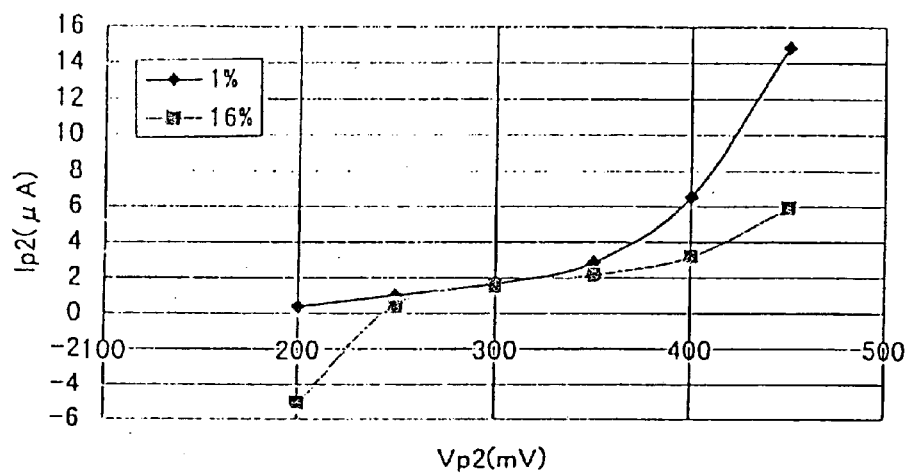
FIG. 16 is a graph showing the relation between the second oxygen ion pump cell current Ip2 and the voltage applied across the same cell, when the $O_2$ concentration is changed, according to the embodiment of the third and fourth aspects of the present invention.

The voltage of the oxygen partial pressure detection electrode was set to 450 mV. FIG. 16 showing the test examples 10 and 11 shows the relation between the second oxygen ion pump cell current Ip2 and the voltage Vp2 applied across the cell when the $O_2$ concentration is changed. It is seen that, with the voltage Vp2 applied across the second oxygen ion pump cell of 250 to 400 mV, the value of Ip2, that is Ip2 offset, is lowered, and that the variation of Ip2 to the variation of the amount of the oxygen concentration is only small such that the oxygen concentration dependency of Ip2 is low.

Results of Measurement 11

Figure 17:
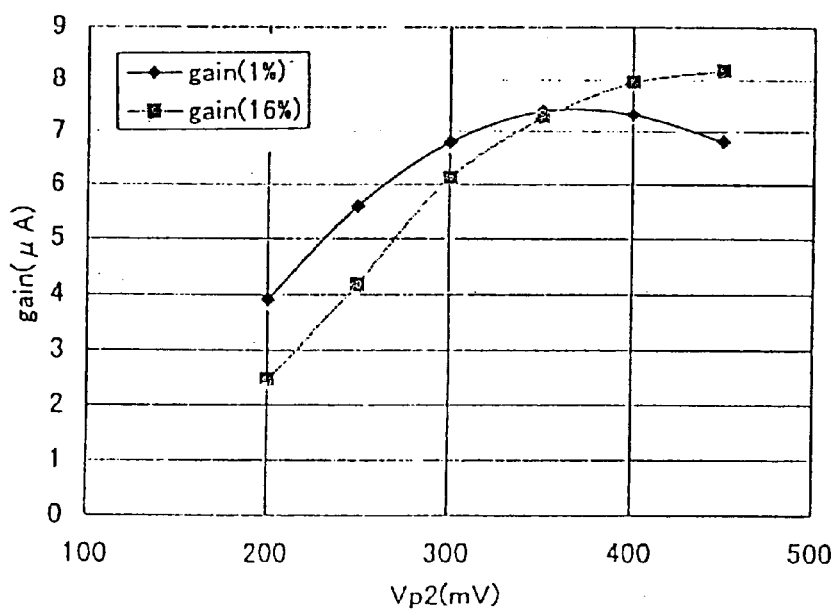
FIG. 17 is a graph showing the relation between the second oxygen ion pump cell current Ip2 and the voltage Vp2 applied across the same cell, when the $O_2$ concentration is changed, according to the embodiment of the third and fourth aspects of the present invention.

The voltage of the oxygen partial pressure detection electrode was set to 450 mV. FIG. 17 showing the relation of Vp2 to the difference between test examples 12 and 10 and the difference between test examples 13 and 11 shows the relation between the gain of the second oxygen ion pump cell current Ip2 and the voltage Vp2 applied across the cell in case the $O_2$ concentration is changed. It is seen that, for the voltage Vp2 applied across the second oxygen ion pump cell of 250 to 400 mV, the variation of the gain of Ip2 relative to the variation in the oxygen concentration is small, such that the oxygen concentration dependency of the Ip2 gain is small.

Results of Measurement 12

Figure 18:
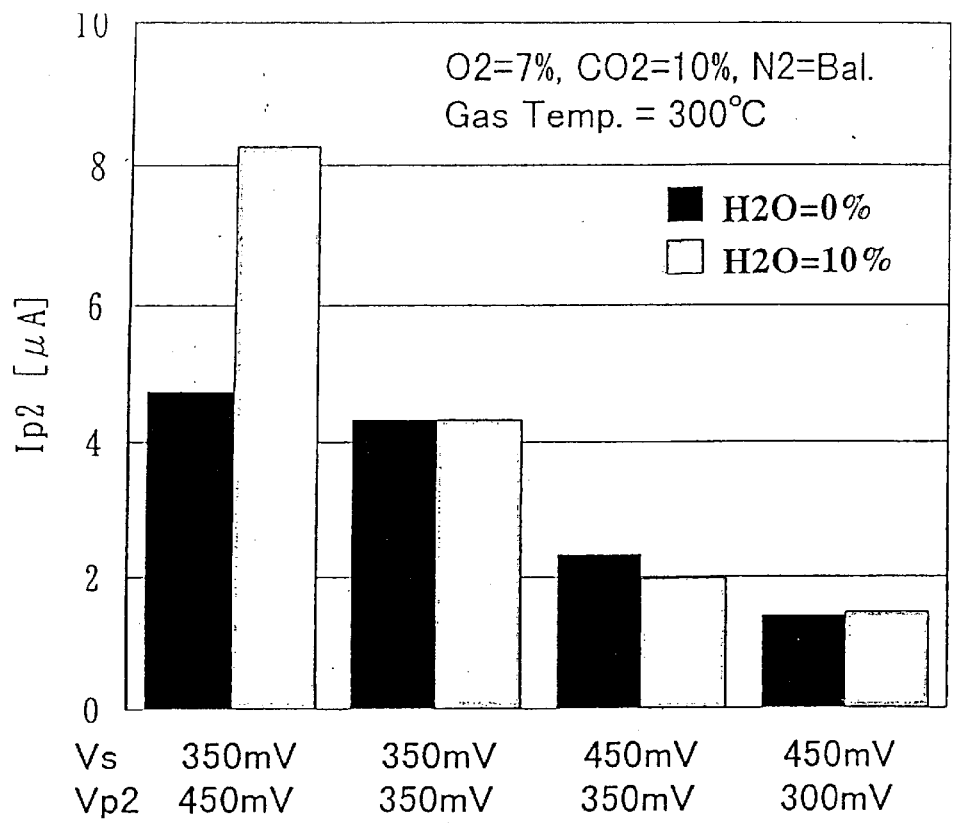
FIG. 18 is a graph showing the dependency of the second oxygen ion pump cell current Ip2 on the potential Vs of the oxygen partial pressure detecting electrode and the second oxygen ion pump cell current Ip2 and the dependency on $H_2O$, according to the embodiment of the third and fourth aspects of the present invention.

FIG. 18, showing test examples 14 to 17 in a graph, shows the dependency of the second ion pump cell current Ip2 on the combination of the potential Vs of the oxygen partial pressure sensor electrode and the voltage Vp2 applied across the second oxygen ion pump cell and the dependency on $H_2O$. In the graphs, left-side bars and right-side bars represent Ip2 for $H_2O$:0% and Ip2 for $H_2O$:10%, respectively. The measurement conditions are as shown in the graph. It is seen from this graph that, for Vs:350 mV and for Vp2:350 mV, there is no difference in Ip2 between the case of $H_2O$:0% and the case of $H_2O$:10%. Therefore, this condition is optimum in decreasing the $H_2O$ dependency of Ip2. It is also seen from this graph that, for Vp2:300 to 350 mV, the $H_2O$ dependency of Ip2 is small, this dependency being similarly small for Vp2 of 300 to 400 mV.

Results of Measurement 13

Figure 19:
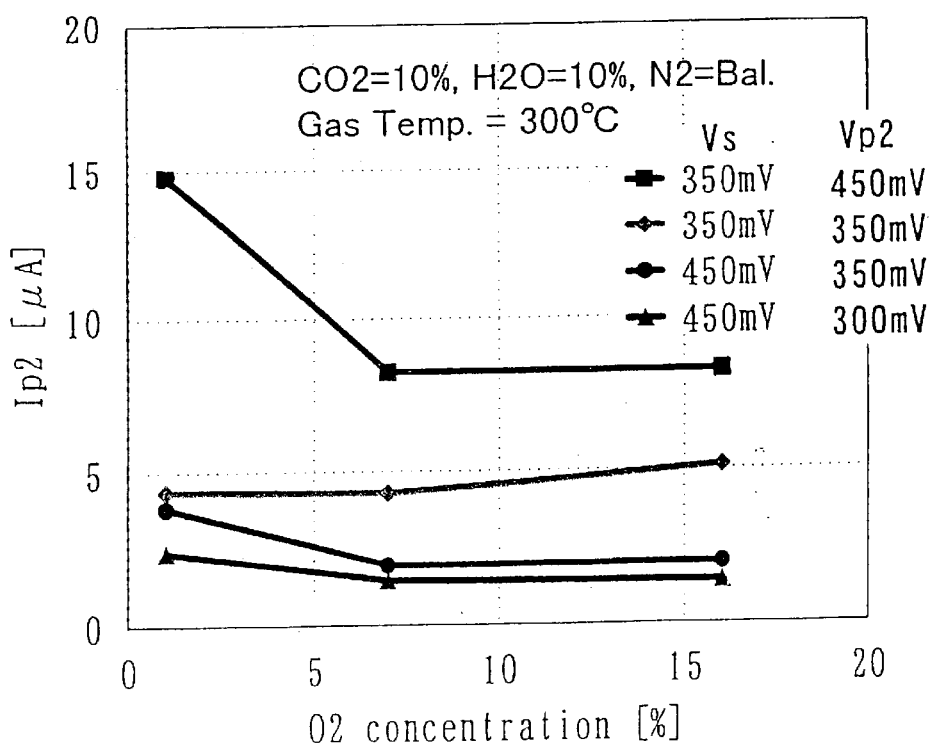
FIG. 19 is a graph showing the dependency of the second oxygen ion pump cell current Ip2 on the potential Vs of the oxygen partial pressure detecting electrode and the second oxygen ion pump cell current Ip2 and the dependency of the second oxygen ion pump cell current Ip2 on the $O_2$ concentration according to the embodiment of the third and fourth aspects of the present invention.

FIG. 19, showing the test examples 18 to 21, shows the $O_2$ concentration dependency of the second oxygen ion pump cell current Ip2. The measurement conditions are as shown in the graph. It is seen from this graph that, for Vp2:300 to 350 mV, the value of Ip2, that is the offset, is small, with the extent of the variation of Ip2 with respect to changes in the $O_2$ concentration being small. The same presumably holds for Vp2:300 to 400 mV. Also, the value of Ip2, that is the offset, is smaller for Vs:450 mV than for Vs:350 mV.

Results of Measurement 14

Figure 20:
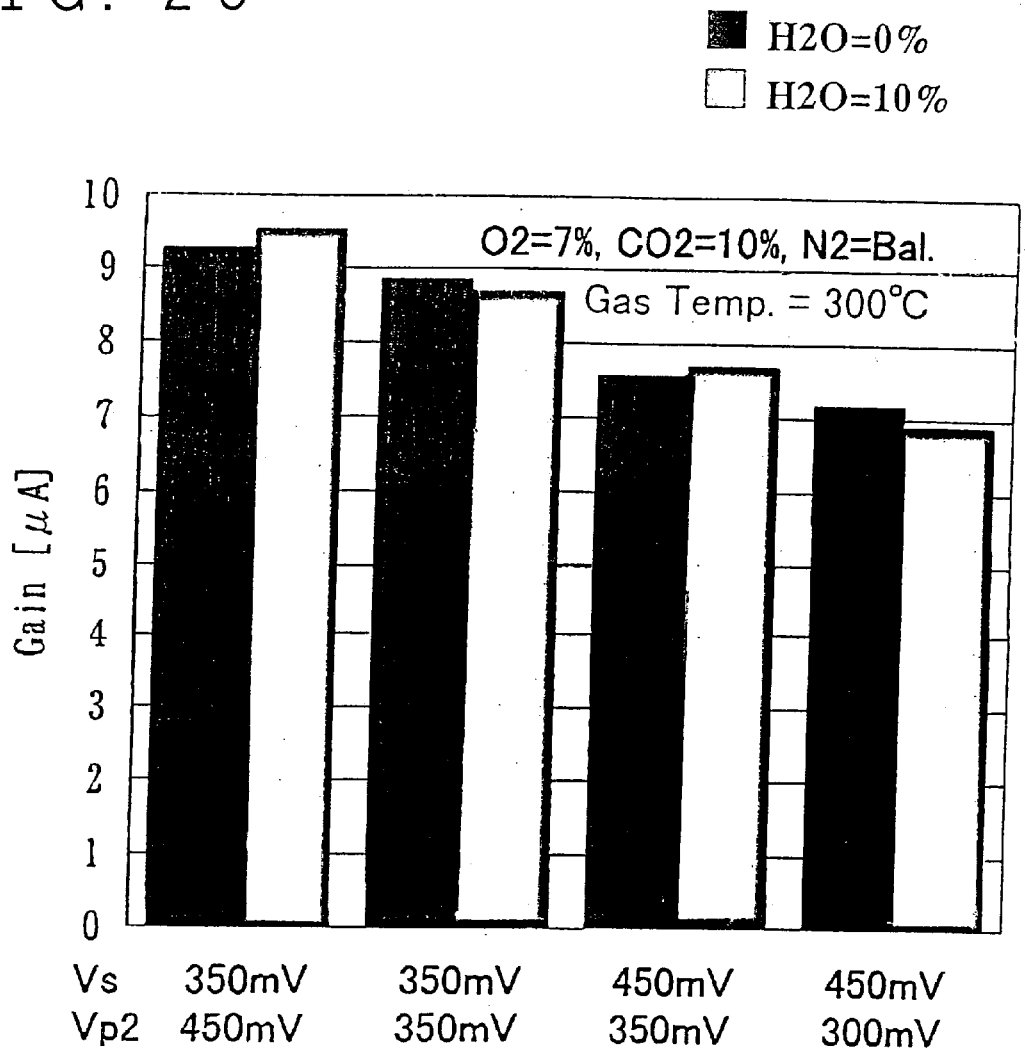
FIG. 20 is a graph showing the dependency of the gain of the second oxygen ion pump cell current Ip2 on the potential Vs of an oxygen partial pressure sensor electrode Vs and the voltage Vp2 applied the second oxygen ion pump cell on $H_2O$, and the dependency thereof on $H_2O$, according to the embodiment of the third and fourth aspects of the present invention.
Figure 21A:
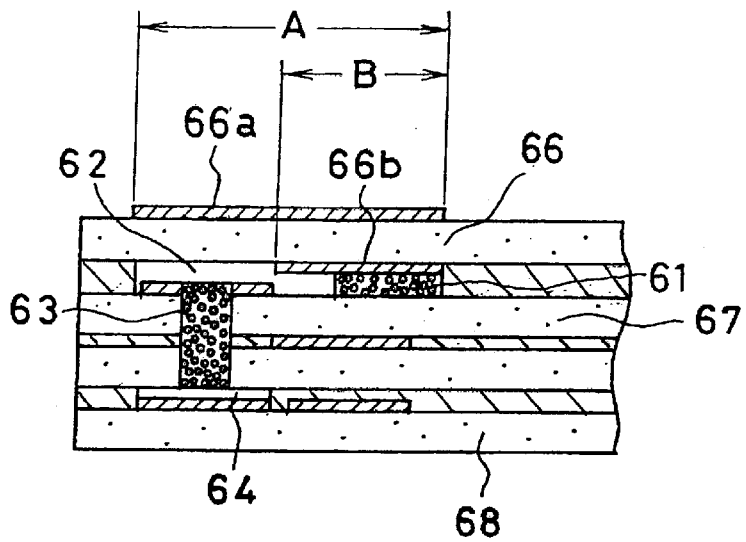
FIG. 21 shows an embodiment having a short length B on an inner electrode in a first oxygen pump cell.
Figure 21B:
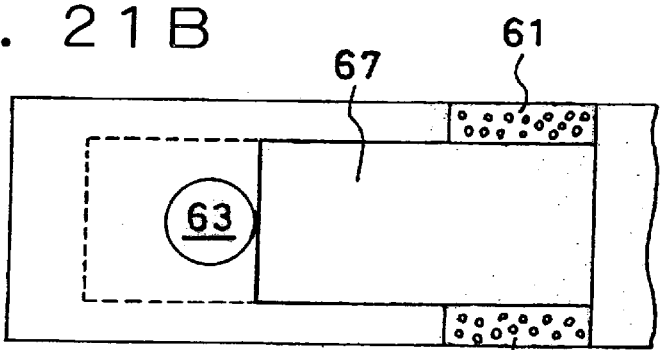
Figure 21C:
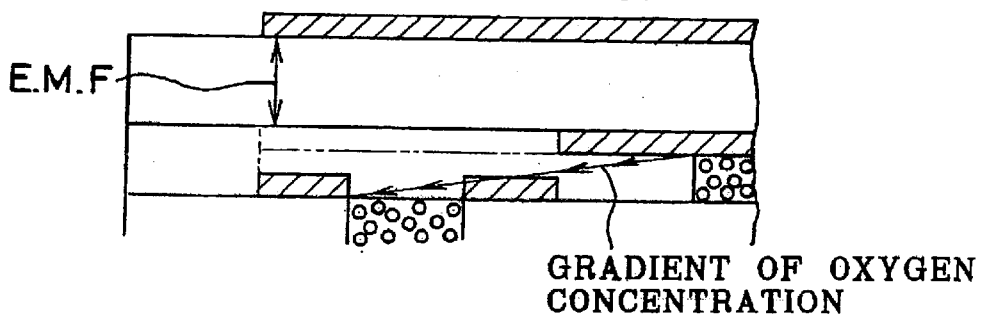
Figure 21D:
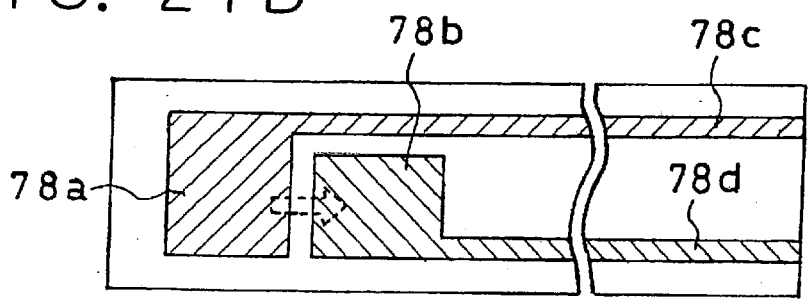

FIG. 20, showing test examples 22 to 25 in a graph, shows the dependency of the gain of the second ion pump cell current Ip2 on the combination of the potential Vs of the oxygen partial pressure sensor electrode and the voltage Vp2 applied across the second oxygen ion pump cell and on $H_2O$.

In the graphs, left-side bars and right-side bars represent Ip2 for $H_2O$:0% and for Ip2 $H_2O$:10%, respectively. The measurement conditions are as shown in the graph. It is seen from this graph that, for Vs: 350 to 450 mV and for Vp2:300 to 450 mV, the change of Ip2 gain relative to the $H_2O$ concentration s small.

Type 2 Sensor: It has been shown that, if a sensor shown in FIG. 3, in which an outer electrode of the second oxygen ion pump cell (electrode positioned outside the second measurement chamber) is coated with an insulated coat paste (3), a fourth layer of the $ZrO_2$ sheet and a protective coat paste, and hence is not exposed to the atmosphere under measurement (outside air), an optimum impressed voltage Vp2 across the second oxygen ion pump cell is higher than if the type 1 sensor is used. With the type 2 sensor, an optimum Vp2 value was 400 to 500 mV. This is possibly ascribable to the atmosphere in the vicinity of the outer side electrode of the second oxygen ion pump cell, that is to the oxygen concentration on the inner and outer sides of the second measurement chamber.

Type 2 (Enclosed Type)

FIG. 21 (A)–(D) illustrates the structure of the type 2 NOx gas concentration sensor fabricated as shown in FIG. 3. (The structure will be later indicated with reference to FIG. 36.) In this sensor, the length of an electrode 66b on the flow passage side provided on the first oxygen ion pump cell 66 is set so as to be shorter than that of the electrode outside the flow passage. The effect of reducing the electrode length in this manner will be explained subsequently by referring to FIG. 36. Using this type 2 (enclosed type) sensor, tests were conducted under the following conditions or the conditions shown in the drawing, as in the case of the type 1 (exposed type) sensor.

Measurement Result 15, Type 2, $O_2$=7%, Vs=350 mV

Figure 22:
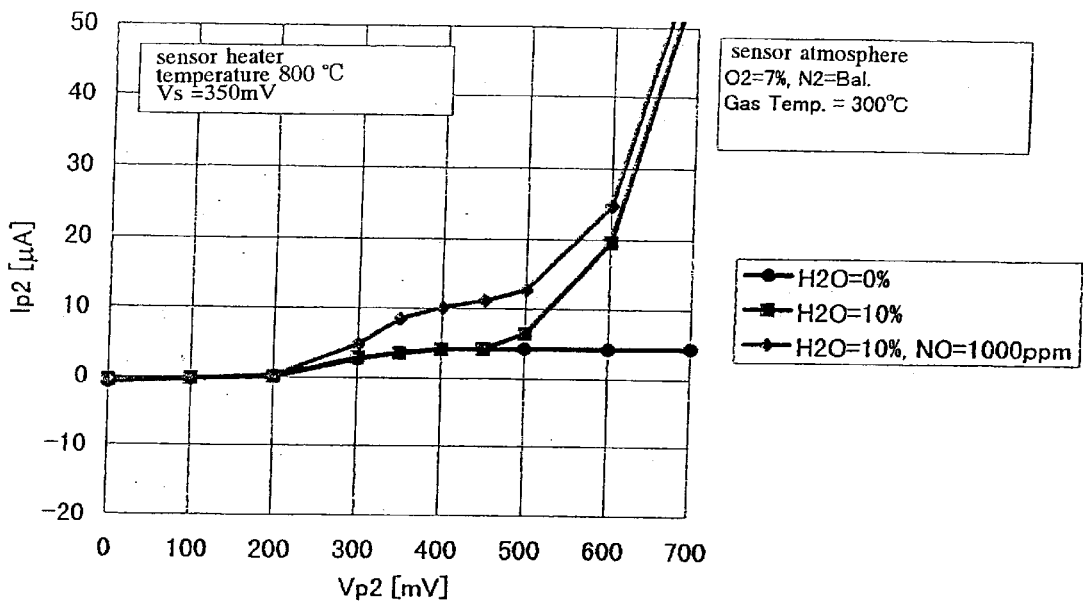
FIGS. 22–24 show test results of an embodiment having an enclosed type outer electrode of a measuring cell, demonstrating the influence of $H_2O$.

FIG. 22 illustrates the results of measurement conducted similarly to the test examples 6 and 7 (FIG. 12) using the type 2 sensor. It is seen from FIG. 22 that, if VP2 is set to not higher than 500 mV (pre-set voltage), preferably to not higher than 450 mV (pre-set voltage), the $H_2O$ concentration dependency of the difference between IP2 for $H_2O$ of 0% and that for $H_2O$ of 10%, that is a sensor output, is relatively small. It is also seen from FIG. 22 that, if VP2 is set to not higher than 500 mV (pre-set voltage), preferably to not higher than 450 mV (pre-set voltage), the difference in IP2 (gain) for NO of 0 ppm and that for NO of 1000 ppm, with the $H_2O$ concentration being 10%, becomes larger.

Results of Measurement 16, Type 2, $CO_2$ Dependency

Using the type 2 NOx gas concentration sensor, as in the test example of the results of measurement 15, the $CO_2$ gas concentration dependency of the sensor output was checked. It is seen from FIG. 23 that, if VP2 is set to not higher than 500 mV (pres-et voltage), the $CO_2$ gas concentration dependency of the difference between IP2 for $CO_2$ of 0% and that for $CO_2$ of 10%, that is a sensor output, is relatively small. It is also seen from FIG. 23 that, if VP2 is set to not higher than 500 mV (pre-set) voltage), preferably to not higher than 450 mV (pre-set voltage), the difference in IP2 (gain) for NO of 0 ppm and that for NO of 1000 ppm, with a $CO_2$ concentrate being 10%, becomes larger.

Results of Measurement 17, Type 2, Vs=350 mV

Figure 23:
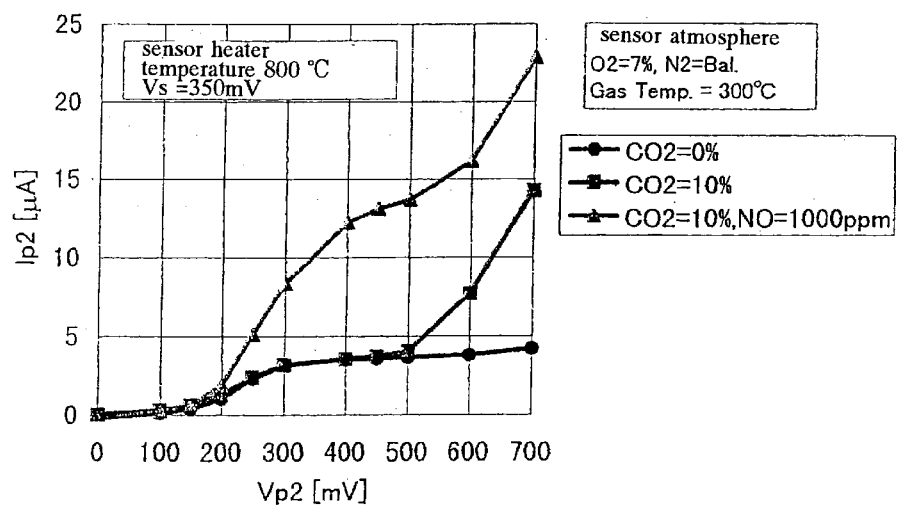
Figure 24:
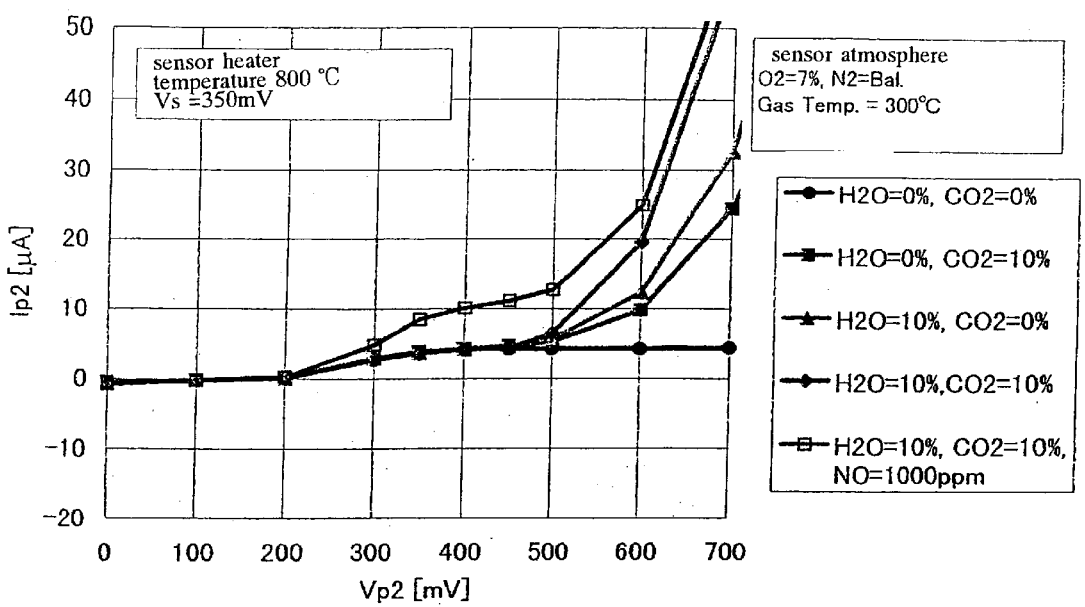

FIG. 24, showing the $H_2O$+$CO_2$ dependency of the type 2 NOx gas concentration sensor, is equivalent to the results of measurement 15 of FIG. 22 and the results of measurement 16 of FIG. 23 put together. It is seen from FIG. 24 that the $H_2O$+$CO_2$ dependency of the sensor output IP2 becomes smaller by setting VP2 to 300 mV to 500 mV, preferably to not higher than 450 mV.

Results of Measurement 18, Type 1, Vs=450 mV

Figure 25:
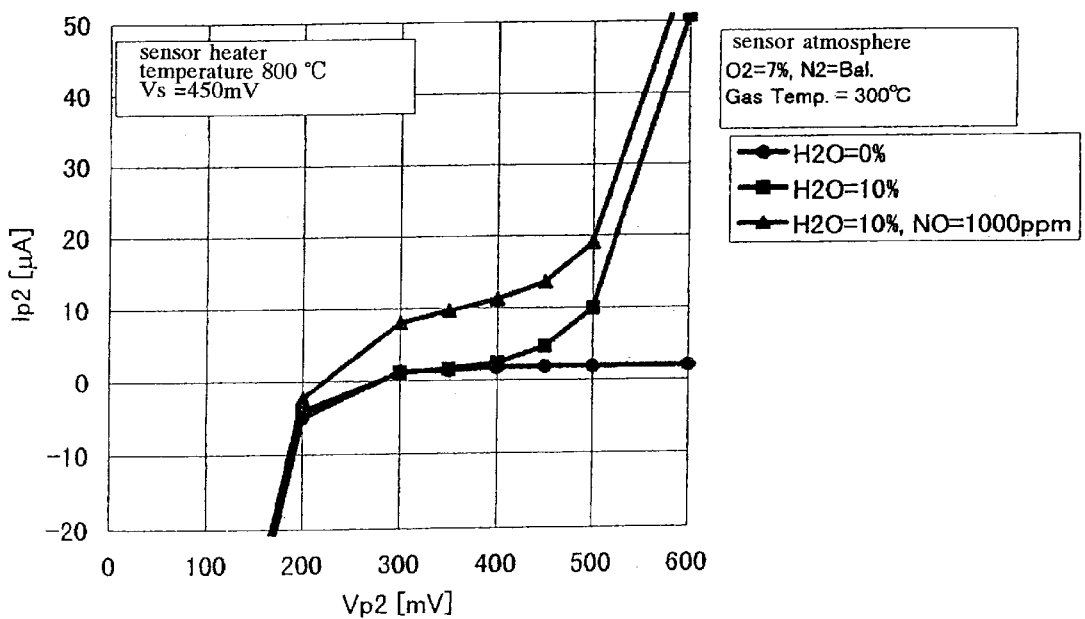
FIG. 25 is a graph showing the influence of $H_2O$ in case of the expose type outer electrode.

Using the type 1 NOx gas concentration sensor, the $H_2O$ concentration dependency of the sensor was checked, as in the results of measurement 10 and 11, but with the exception that Vs=450 mV was set (Vs=350 mV was set for the results of measurement 10 and 11, as shown in FIG. 15). It is seen from FIG. 25 that the $H_2O+CO_2$ dependency of the sensor output IP2 becomes smaller by setting VP2 to not larger than 300 to 400 mV.

Results of Measurement 19, Type 2, $O_2$=7%, Vs=450 mV

Figure 26:
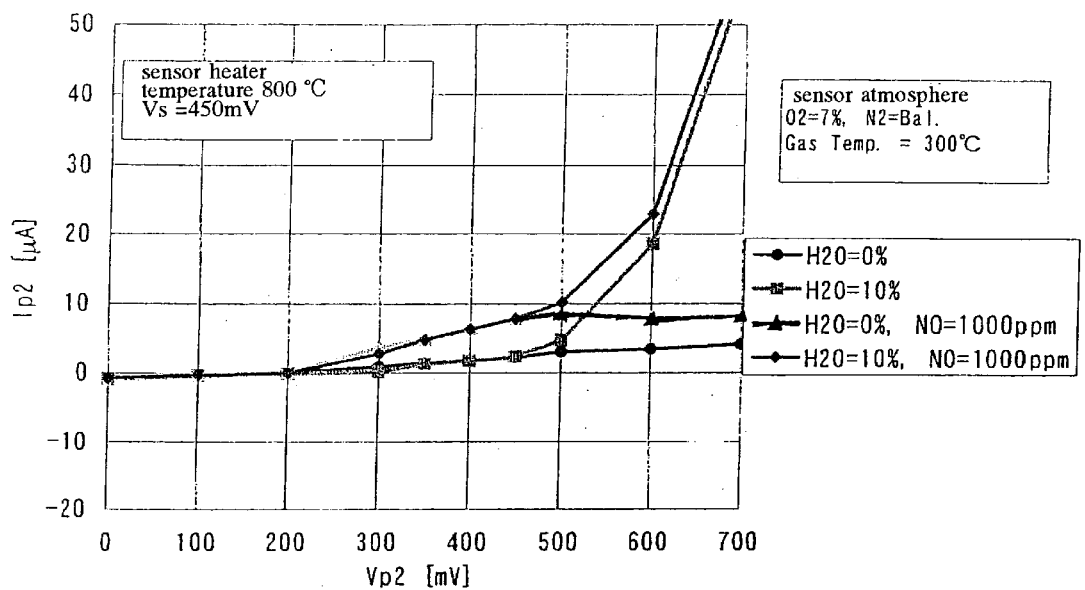
FIGS. 26–34 are graphs showing the influence of $H_2O$ under various test conditions.

Using the type 2 NOx gas concentration sensor, the $H_2O$ concentration dependency of the sensor was checked, as in the results of measurement 15 (FIG. 22), but with the exception that Vs=450 mV was set (Vs=350 mV was set for the results of measurement 15). FIG. 26 shows the results of measurement. It is seen from FIG. 26 that, by setting VP2 to 300 to 500 mV, preferably to not higher than 450 mV, the $H_2O$ dependency of the sensor output IP2 becomes smaller.

Results of Measurement 20, Type 1, $O_2$=7%, $H_2O$=10%, Vs=350 mV

Figure 27:
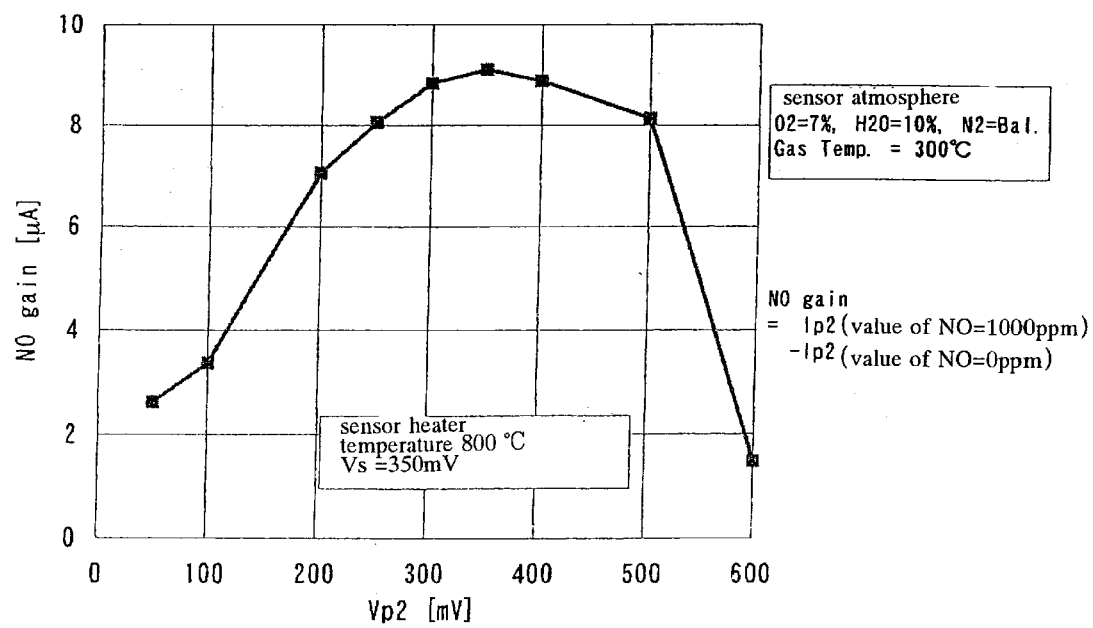

Using the type 1 sensor, the VP2 dependency of the IP2 (NO) gain was checked for $V_s$=350 mV. It is seen from FIG. 27 that the gain desirably becomes locally maximum by setting VP2 to 300 to 400 mV.

[Results of Measurement 21, Type 1, $O_2$=7%, $H_2O$=10%, Vs=450 mV]

Figure 28:
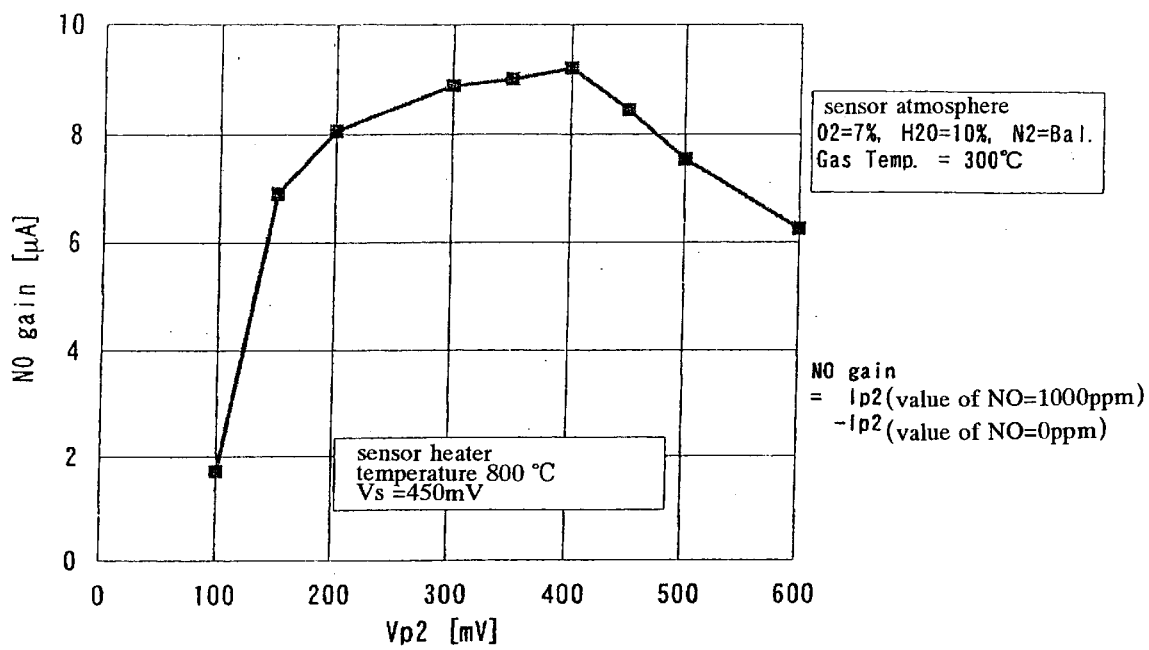

A test was conducted in the same way as in the results of measurement 15, except setting Vs to 450 mV. It is seen from FIG. 28 that the gain desirably becomes locally maximum by setting VP2 to 300 to 450 mV, preferably to not higher than 400 mV.

[Results of Measurement 22, Type 2, $O_2$=7%, $H_2O$=10%, Vs=350 mV]

Figure 29:
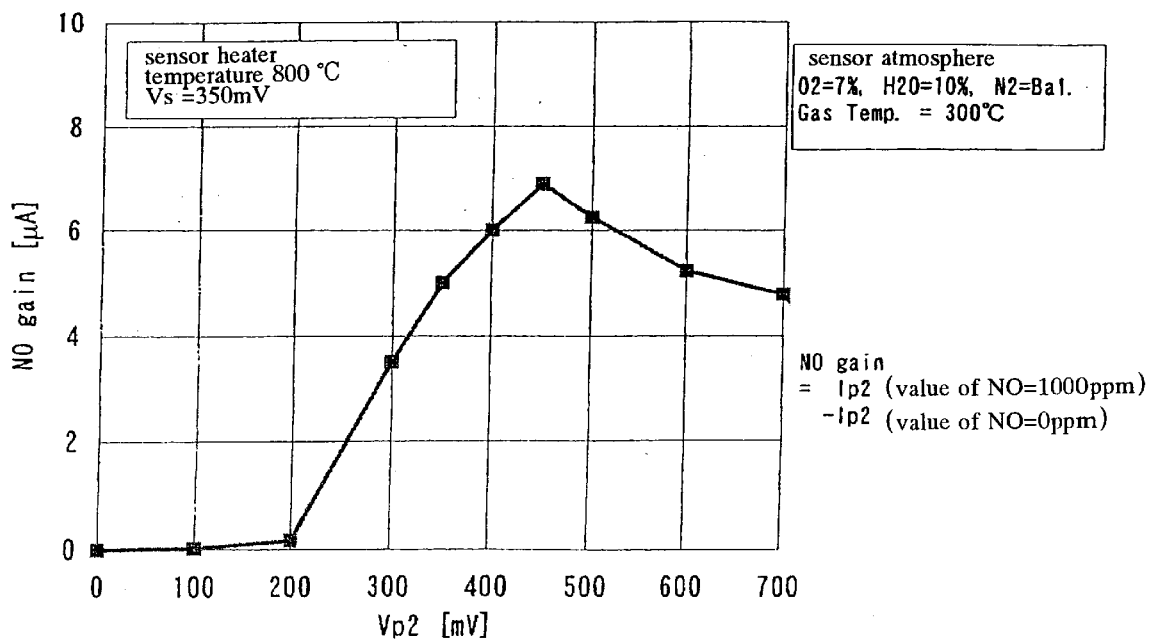

Using the type 1 sensor, the VP2 dependency of the IP2 (NO) gain was checked for Vs=350 mV. It is seen from FIG. 29 that the gain desirably becomes locally maximum by setting VP2 to 400 to 500 mV.

[Results of Measurement 23, Type 2, $O_2$=7%, $H_2O$=10%, Vs=450 mV]

Figure 30:
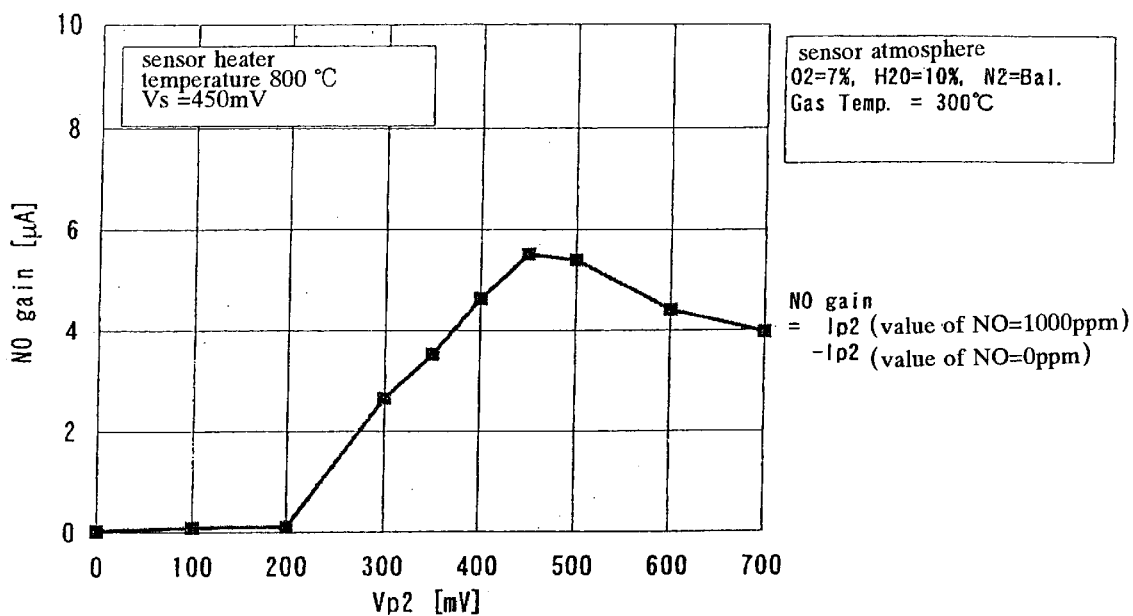

A test was conducted in the same way as in the results of measurement 22, except setting Vs to 450 mV. It is seen from FIG. 30 that the gain desirably becomes locally maximum by setting VP2 to 400 to 500 mV.

[Results of Measurement 24, Type 2, $O_2$=7%, $H_2O$=15%, $CO_2$=15%, Vs=450 mV]

Figure 31:
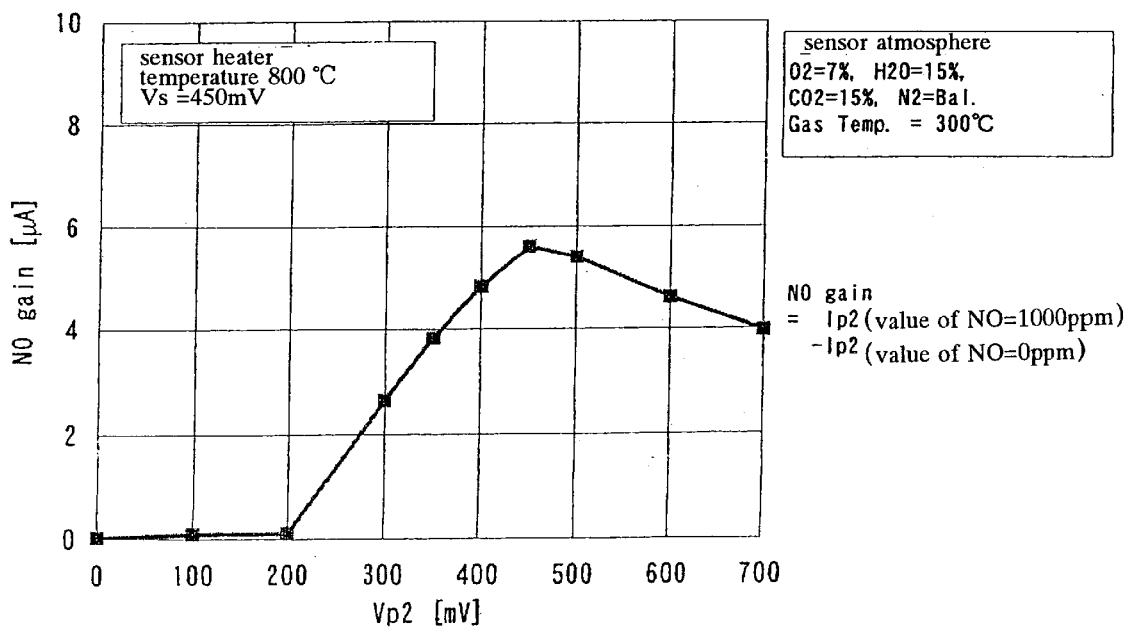

Using the type 2 sensor, the VP2 dependency of the IP2 (NO) gain was checked for Vs=450 mV, as in the results of measurement 22 and 23. It is seen from FIG. 31 that the gain desirably becomes locally maximum by setting VP2 to 400 to 500 mV.

[Results of Measurement 25, Type 2, $O_2$=7%, H O=10%, CO=10%, Vs=450 mV]

Figure 32:
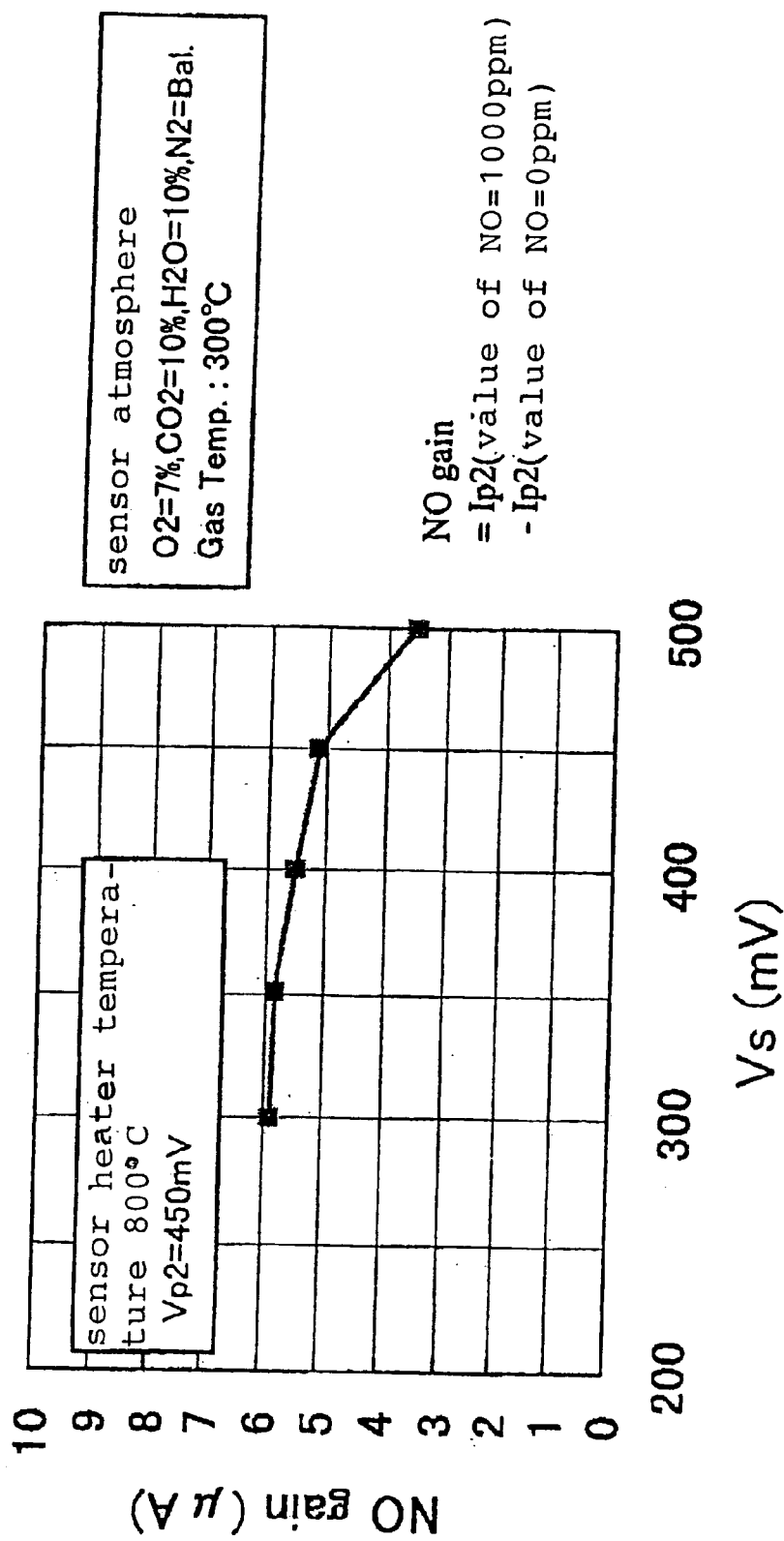

Using the type 2 sensor, the VP2 dependency of the IP2 (NO) gain was checked for Vs=450 mV, as in the results of measurement 24. It is seen from FIG. 32 that the gain desirably becomes locally maximum by setting VP2 to 300 to 400 mV.

[Results of Measurement 26, Type 2, $O_2$=7%, $H_2O$=10%, $CO_2$=10%, Vs=450 mV]

Figure 33:
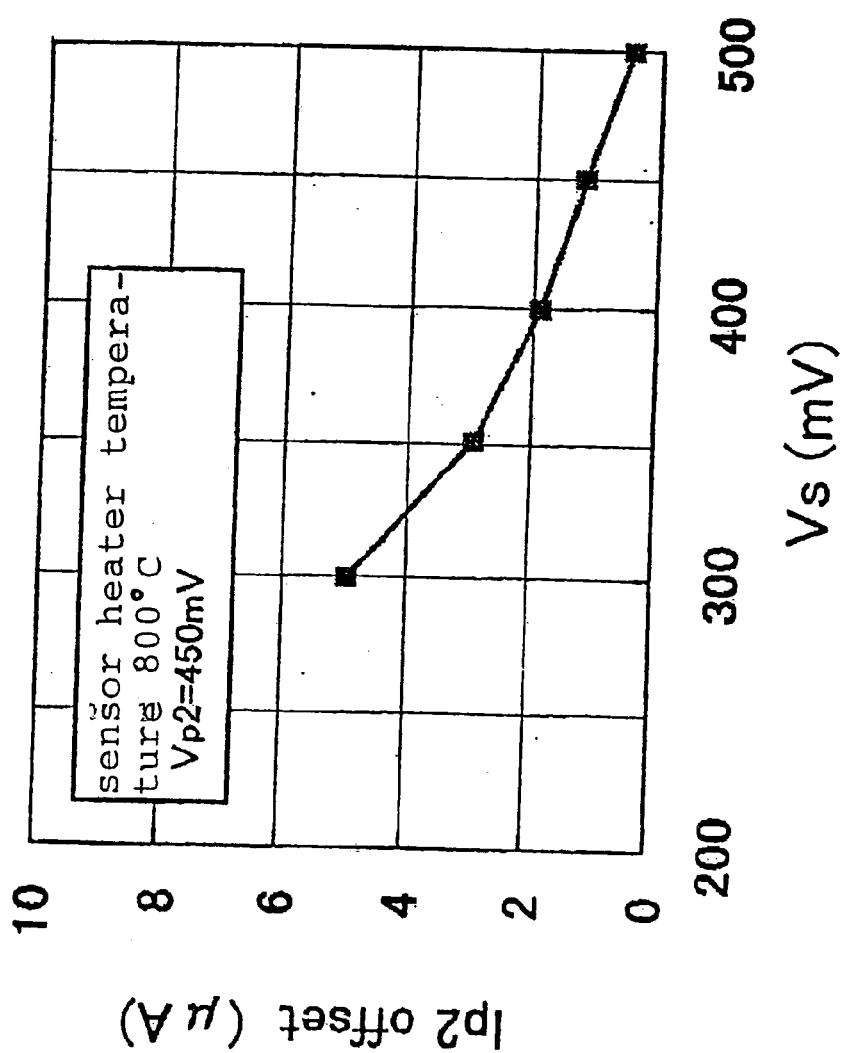

Using the type 2 sensor, the VP2 dependency of the IP2 (NO) offset was checked for VP2=450 mV, as in the results of measurement 25. It is seen from FIG. 33 that the offset desirably becomes smaller by setting VS to a higher value.

[Results of Measurement 27, Type 2, $O_2$, Vs=350 mV]

Figure 34:
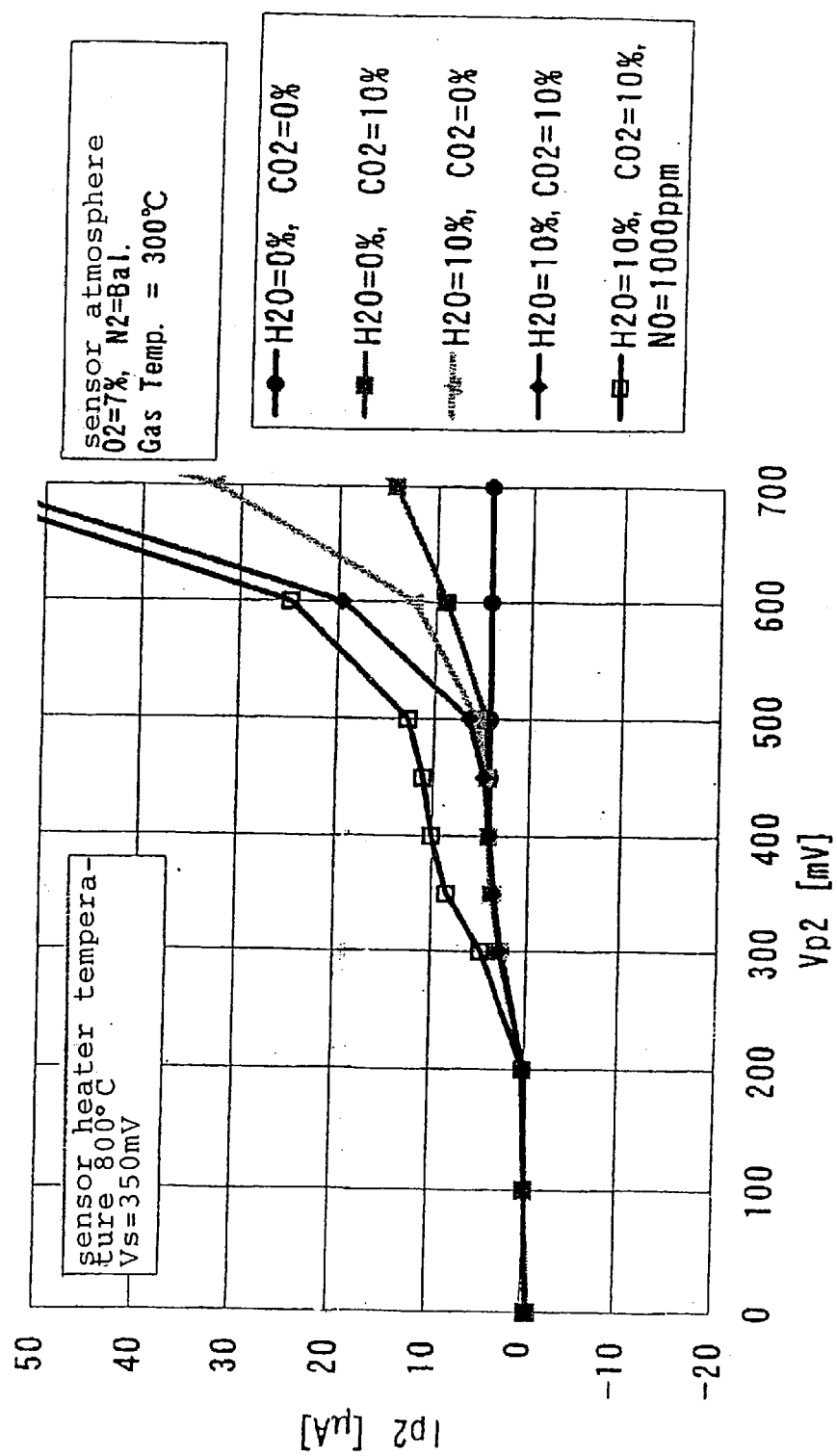

Using the type 2 sensor, Vs was set to Vs=350 mV, and the Vp2 dependency of Ip2 was checked for varying values of the concentration of $H_2O$ and $CO_2$ It is seen from FIG. 34 that, by setting Vp2 to 300 to 500 mV and preferably to 400 to 500 mV, the $H_2O+CO_2$ dependency of Ip2 is reduced to enable correct measurement of the NOx gas concentration without being affected by interfering gases.

Figure 35:
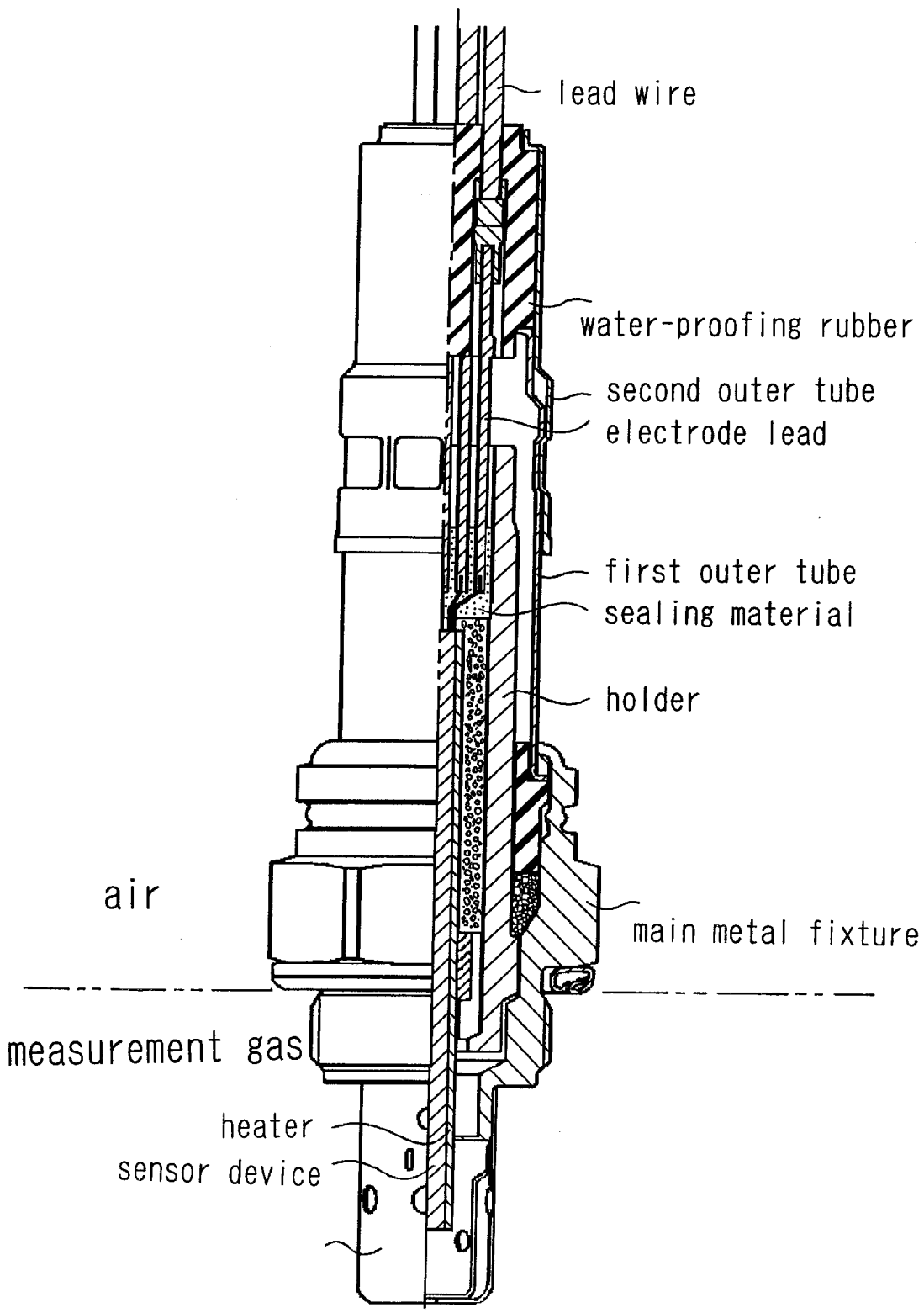
FIG. 35 shows an example in which a NOx gas sensor according to the embodiment of the second and fourth aspect of the present invention is fitted to a metal body.

FIG. 35 shows an embodiment in which a NOx gas sensor according to the present invention is assembled to a main metal body (mounting member). Th sensor device is secured so that its lower portion formed with an inlet for the measurement gas is located in a protector having a hole. A heater is annexed to the sensor device for extending along its length. The upper portion of the heater and the sensor device is coated with a sealing material. The lower sealing material is formed of a porous material to permit passage of a gas, with the upper sealing material being formed of an air-tight material. A holder is provided on an outer peripheral side of a sealing material and a stainless (steel) material and a talc material are enclosed between the holder and the main metal body. Thus, the holder is secured to the main metal body via stainless material and talc material by a caulking force applied across the radius of the main metal body and a caulking force applied in the axial direction for stably holding the sensor device. On an upper part of the mounting metal body, a first outer tube and a second outer tube are assembled coaxially and retained relative to each other. The first outer tube is extended into the inside of and retained by the main metal body. Within an upper portion of the second outer tube, water-proofing rubber is sealed. An electrode, not shown, formed on the sensor device, is electrically connected, via an electrode lead, having a gas diffusion resistance, to an end of a lead wire having a gas diffusion resistance, with the opposite end of the lead wire being connected to atmosphere.

Aspect C

[NOx gas concentration sensor pertaining above all to the aspects 2—2 and 2–3 of the present invention]

Figure 36A:
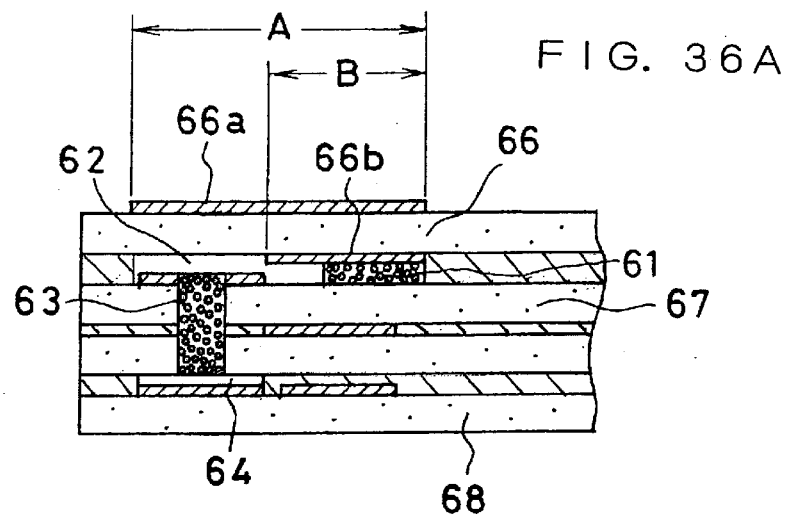
Figure 36B:
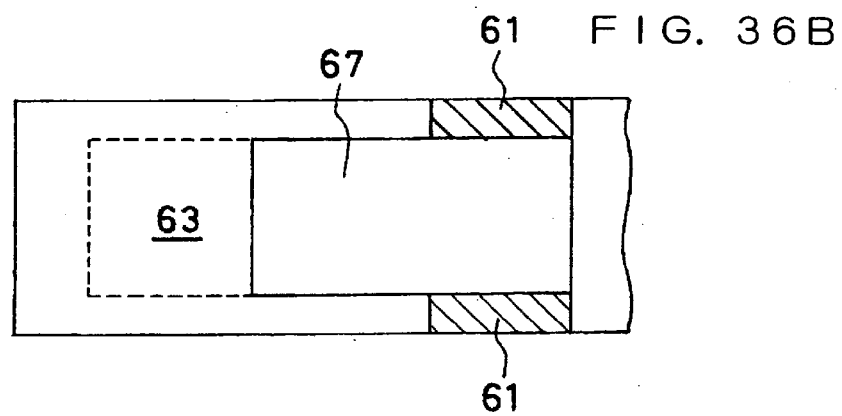
Figure 36C:
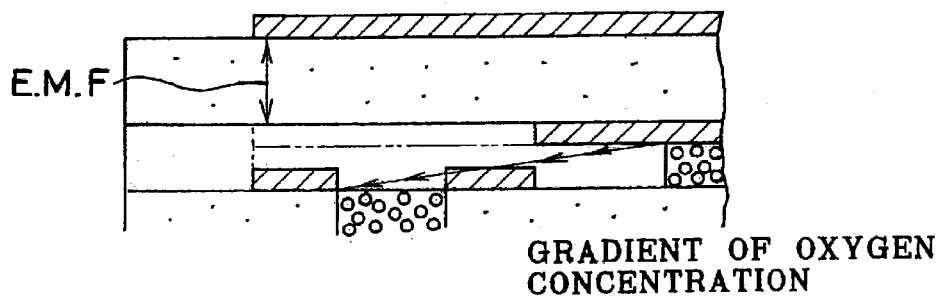
Figure 36D:
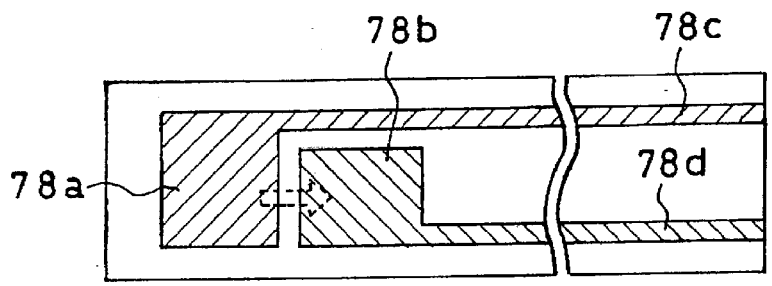

FIGS. 36A to 36D illustrate a NOx gas concentration sensor according to an embodiment of the present invention. FIG. 36A is a cross-sectional view taken along the longitudinal direction, FIG. 36B is a paln view of the first measurement chamber, FIG. 36C is a schematic enlarged cross-sectional view of the first measurement chamber and FIG. 36D is a plan view of the second measurement chamber. The sensor shown in FIGS. 36A to 36D includes a layer of a first oxygen ion pump cell 66, having a solid electrolyte layer and electrodes 66a (positive electrode) and 66b (negative electrode) provided on both sides of the solid electrolyte layer, a layer of an oxygen concentration measurement cell 67 having a solid electrolyte layer and oxygen partial pressure detecting electrodes provided on both sides of the solid electrolyte layer, a solid electrolyte layer, and a layer of the second oxygen ion pump cell 68 having a solid electrolyte layer and oxygen ion pump electrodes 68a, 68b provided within and outside the second measurement chamber 64 on one sides of the solid electrolyte layer, layered in this order. The first measurement chamber 62 is defined by left and right insulating layers and upper and lower solid electrolyte layers, while the second measurement chamber 64 is defined above the layer of the second oxygen ion pump cell 68. A first diffusion hole 1 and a second diffusion hole 63 are opened in separation from each other in the first measurement chamber 62 for introducing the measurement gas via a diffusion resistance. The second diffusion hole 63 is passed through the layers of the oxygen concentration measurement cell 67 and the solid electrolyte layer for establishing communication between the first and second measurement chambers 62,64 for supplying a gas containing at least NOx and $O_2$ from the first measurement chamber 62 via diffusion resistance into the second measurement chamber 64.

Between the layers of the solid electrolyte are formed alumina insulating layers. Although not shown, heating layers for heating the sensor are bonded with a cement layer for sandwiching the entire sensor in the stacking direction. The electrodes are connected via leads formed between the layers to outside of the sensor, such as to a power source. Referring to FIG. 36D, the electrodes 68a, 68b of the second oxygen ion pump cell 68 are electrically connected to leads 78c, 78d, as shown in FIG. 35(D).

One of the features of the present sensor is that the first measurement chamber 62 and the second measurement chamber 64 are arranged in substantially superposed state and that the first diffusion holes 61 are formed on both sides of the sensor, instead of its distal end, with a porous material being charged into the second diffusion hole 63, an insulating film being arranged between the solid electrolyte layers and with the electrodes of the cells being insulated from one another. The second measurement chamber 64, defining a void, may be charged with a porous material.

Figure 37:
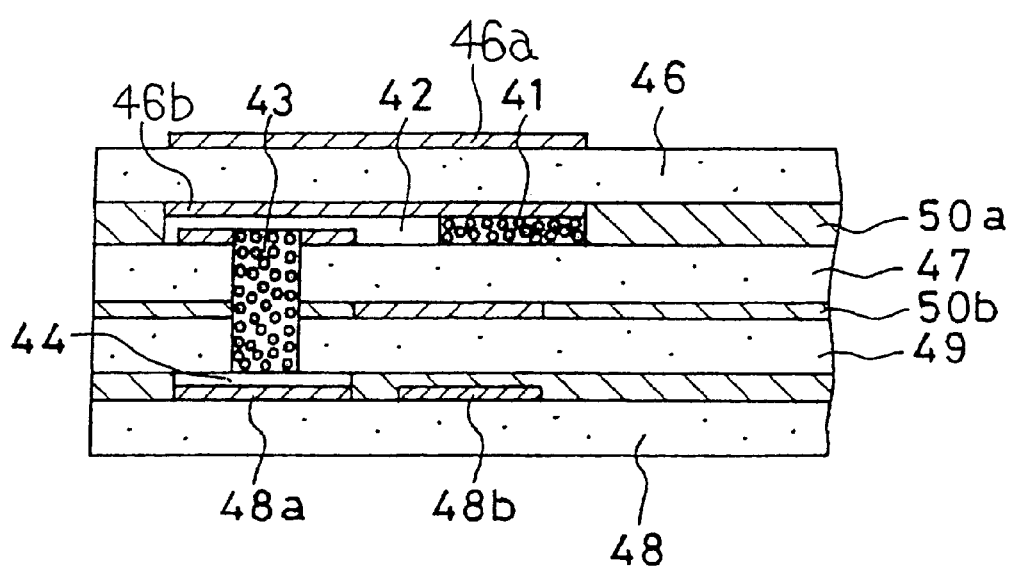
FIG. 37 illustrates a sensor of a reference example for the sensor shown in FIG. 36.

As compared to the sensor of FIG. 37, as a comparative example with respect to the sensor of FIGS. 36A to 36D, the sensor of FIGS. 36A to 36D is characterized by that the lengths of the electrodes 66a (positive electrode) and 66b (negative electrode) provided in the first oxygen ion pump cell 66 as measured in a direction along the flowing direction of the measurement gas flowing from the first diffusion hole 61 towards the second diffusion hole 63 (longitudinal direction) is shorter than the length of the first measurement chamber 62 (A>B), with the inner electrode 66b not being formed to the position directly above the second diffusion hole 63.

Since the operation of the electrodes 66a, 66b will be explained later referring to FIG. 41.

The NOx gas concentration was measured using the embodiment shown in FIGS. 36A to 36D and a sensor of the comparative example shown in FIG. 37. The sensor of the embodiment was of a longitudinal length of 50 mm, a width (short side length of 4 mm and a thickness (in the stacking direction) was 1.3 mm. The first oxygen ion pump cell 66 was 0.3 mm in thickness, while the electrodes 66a, 66b was of a longitudinal length A of 4 mm and B of 4 mm and a short-side length of 2 mm. The first measurement chamber 62 was of a longitudinal length A of 7 mm, a short-side length of 2 mm and a height of 50 $\mu$m. The first diffusion hole 61 was of a longitudinal length of 2 mm, a short-side length of 1 mm and a thickness of 50 $\mu$m, while the second diffusion hole 63 was of a size of $\phi$1 mm and a distance from the end (right-side end) of the first diffusion hole 61 equal to 5.5 mm. The sensor of the comparative example (FIG. 37) is of the same size as the sensor of the embodiment except that the longitudinal size of the electrodes 46a, 46b is 7 mm (A=B).

Figure 38:
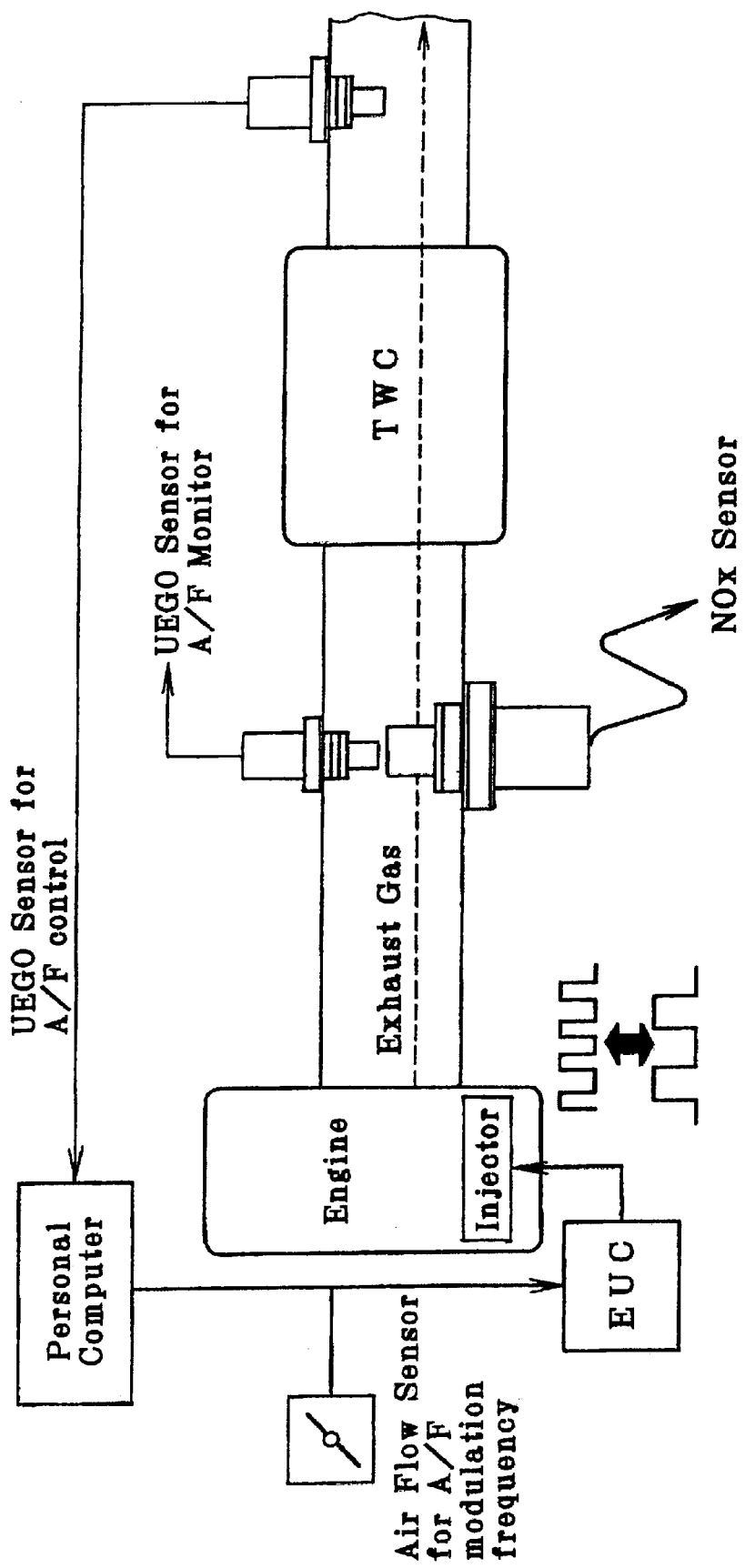
FIG. 38 shows an example of a system for measuring the NOx gas concentration in the exhaust gas.

Referring to the NOx gas concentration measurement system shown in FIG. 38, the measurement method is explained. That is, a dummy signal is entered into an air flow sensor and an injector pulse width was varied for controlling the air/fuel ratio for arriving at the following setting, with the concentration of oxygen in the exhaust gases being changed, for comparing sensor outputs of the sensors of FIGS. 36A to 36D and the sensor of FIG. 37. Since the control was of an open loop, γ-correction was by UEGO. Other conditions are as shown below:

Engine: 2.0 L series 6-cylinder turbo-charger
Engine RPM: 3000 rpm
Suction Duct negative Pressure: −350 mmHg
Frequency: 0.5 Hz
Amplitude (target): λ±3%

Mounting Position: see figure

Figure 39:
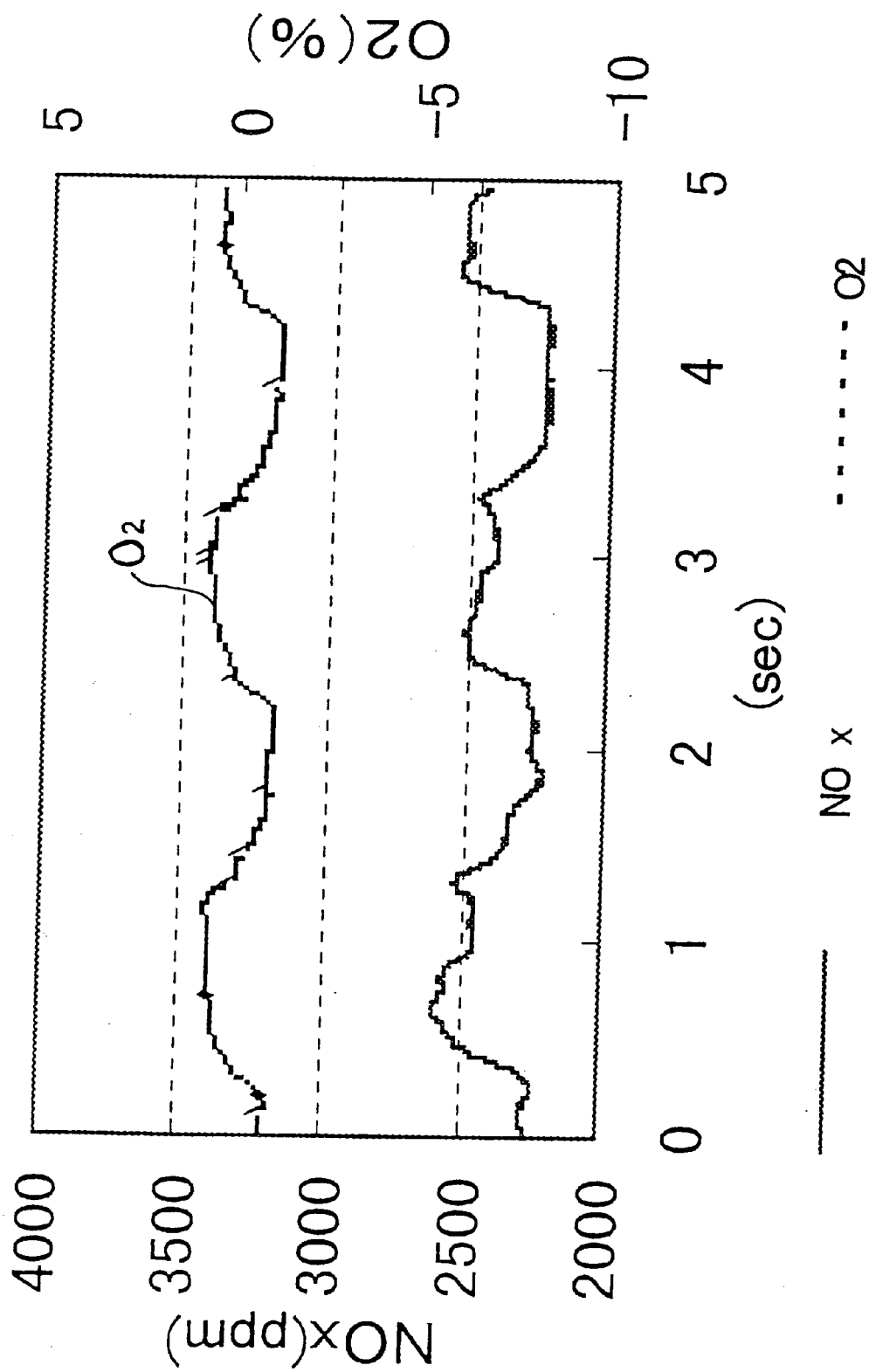
FIG. 39 shows the results of measurement in case the sensor of the example shown in FIGS. 36A to 36D is used for the system shown in FIG. 38.
Figure 40:
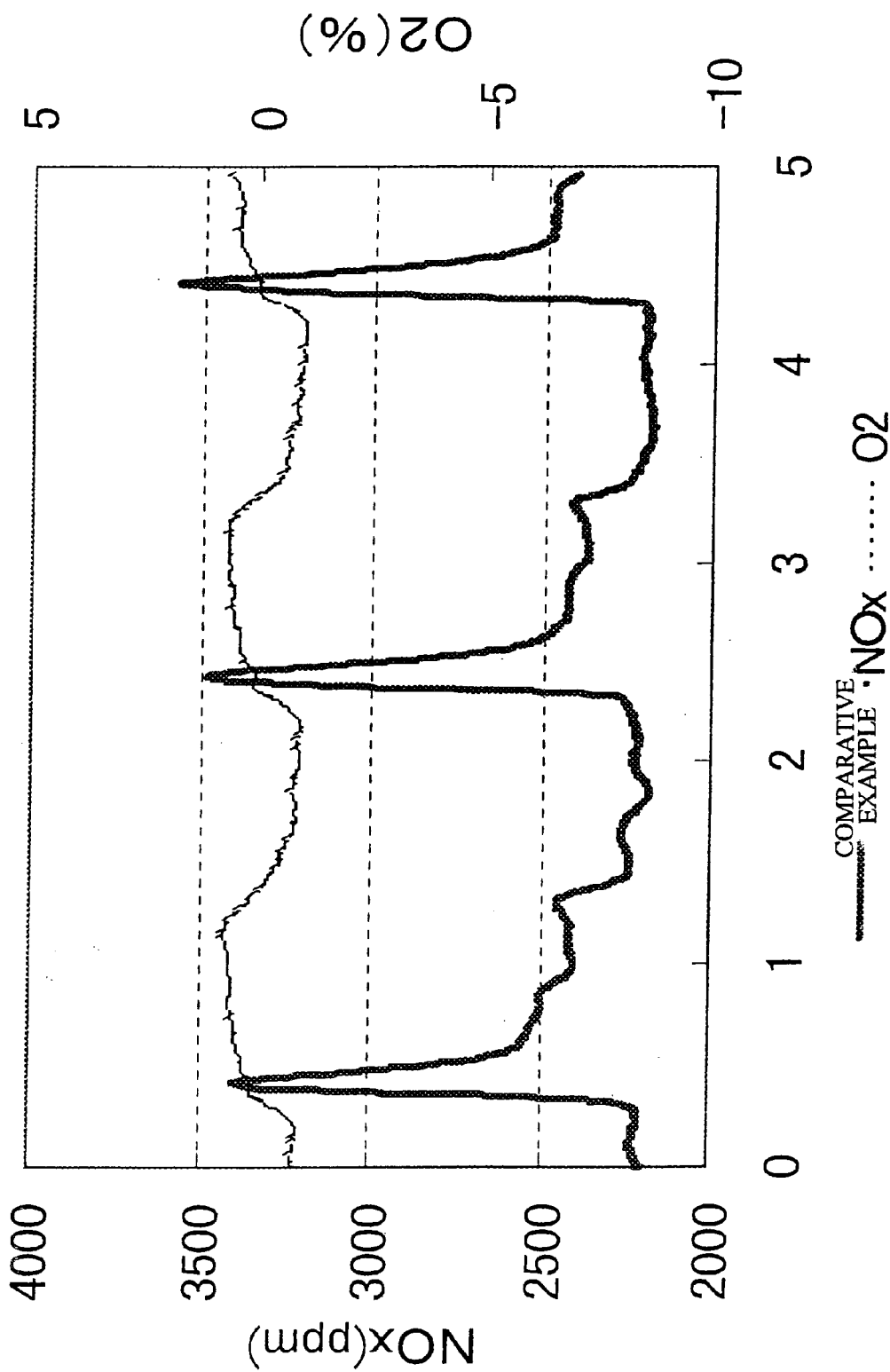
FIG. 40 shows the results of measurement in case the sensor of the comparative example shown in FIG. 29 used for the system shown in FIG. 38.

FIG. 39 shows the results of a sensor of the embodiment shown in FIGS. 36A to 36D, while FIG. 40 shows the results obtained with the sensor of the comparative example shown in FIG. 37. As may be seen from these figures, a large spike noise is produced in the results of the comparative example at the rise time of the oxygen concentration curve (at the time of traversing the stoichiometric point). Conversely, no spike noise is seen in FIG. 39 showing the results of the embodiment. Thus, with the sensor of the embodiment having a structure shown in FIGS. 36A to 36D, the spike noise in the output of the NOx gas concentration sensor at the time of traversing the stoichiometric point is suppressed thus enabling accurate measurement of the NOx gas concentration less susceptible to variations in the oxygen concentration.

The feature of the present aspect C is applied with advantage to a $NO_2$ gas concentration sensor including a first measuring chamber in which a measuring gas is introduced via a first diffusion resistance, an oxygen partial pressure measuring electrode for measuring the oxygen partial pressure in the measuring gas in the first measuring chamber, a first oxygen pumping cell pumping out a sufficient amount of oxygen in the measuring gas out of the first measuring chamber, based on the potential of the oxygen partial pressure measuring electrode, to such an extent as not to substantially cause decomposition of NOx in the measuring gas, a second measuring chamber into which the gas is introduced out of the first measuring chamber via a second diffusion resistance and a second oxygen pumping cell across which the voltage is impressed for decomposing $NO_x$ in the second measuring chamber, with the current flowing therein by the dissociated oxygen in an amount corresponding to the $NO_x$ gas concentration.

In connection with the aspect C, preferably the first diffusion resistance and the second diffusion resistance are arranged towards the first measuring chamber at a spacing from each other. The electrode towards the first measuring chamber and an inlet opening of the second diffusion resistance are formed on one and the other of opposing surfaces of the first measuring chamber, respectively. At least the electrode towards the first measuring chamber of the first oxygen pumping cell is extended from the vicinity of the first diffusion resistance at most towards the first diffusion resistance beyond the top of the inlet opening of the second diffusion resistance. Also preferably, at least the electrode towards the first measuring chamber of the first oxygen pumping cell is not formed directly above or in the vicinity of an opening towards an inlet (first measuring chamber) of the second diffusion resistance.

Referring to FIGS. 41 to 49, an embodiment of the present aspect is explained. The measuring principle in a $NO_x$ gas concentration sensor having two sets of diffusion resistances, an oxygen pumping cell and a measuring chamber is as follows: (1) The exhaust gas flows into the first measuring chamber iva a first diffusion aperture having a diffusion resistance. (2) By the first oxygen pumping cell, oxygen in the first measuring chamber is pumped out to such an extent that oxygen in the first measuring chamber is not decomposed by $NO_x$ (the oxygen partial pressure in the first measuring chamber is controlled by an output signal of an oxygen partial pressure measuring electrode). (3) The gas in the first measuring chamber (concentration-controlled $O_2$ gas plus $NO_x$ gas) flows into the second measuring chamber via a second diffusion aperture having a diffusion resistance. (4) By the second oxygen pumping cell further pumping out oxygen from the gas in the second measuring chamber, the $NO_x$ gas in the second measuring chamber is decomposed into $N_2$ and $O_2$ (5) Since the current $Ip_2$ flowing through the second oxygen pumping cell has a linear relation with respect to the $NO_x$ gas concentration, the $NO_x$ gas concentration can be measured by detecting $Ip_2$.

Figure 41A:
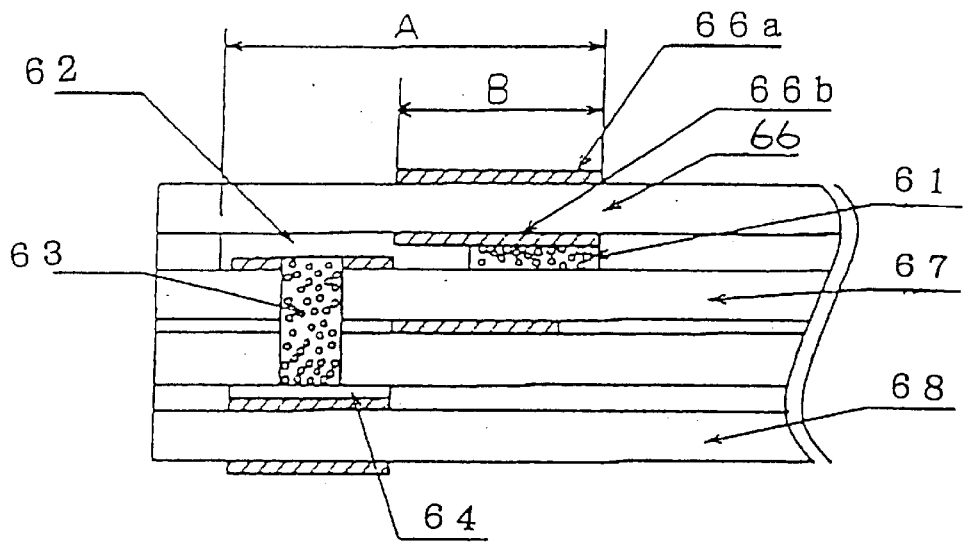
FIG. 41 shows an embodiment having a short length B of an inner electrode in the first oxygen pump cell.
Figure 41B:
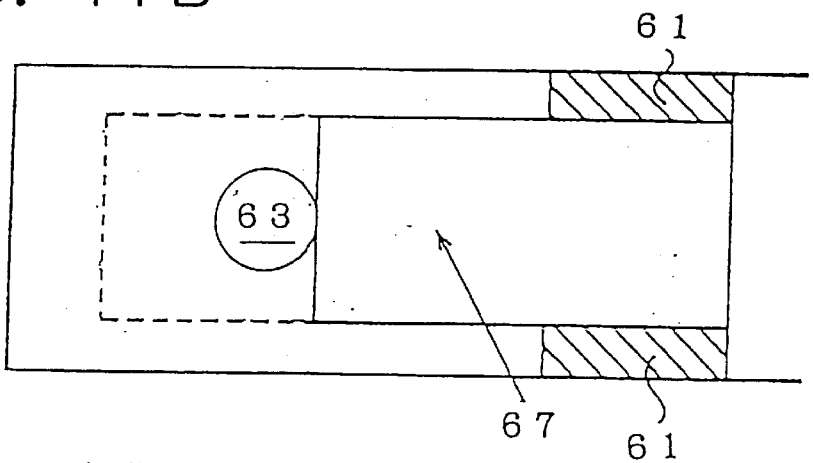
Figure 41C:
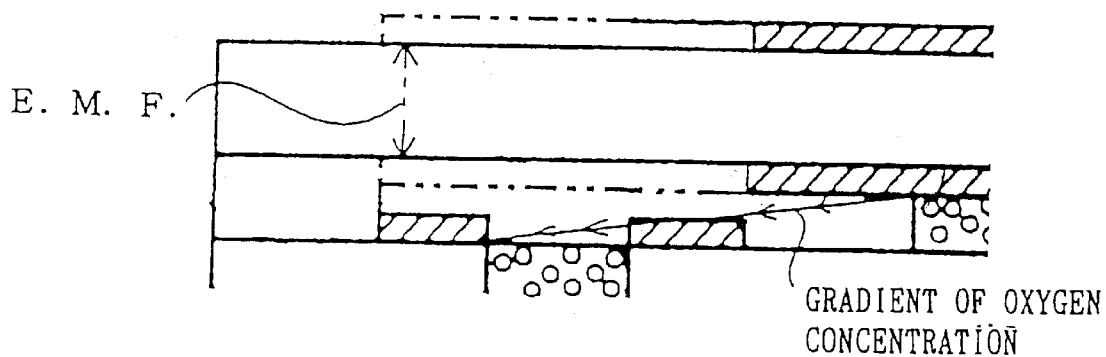
Figure 49:
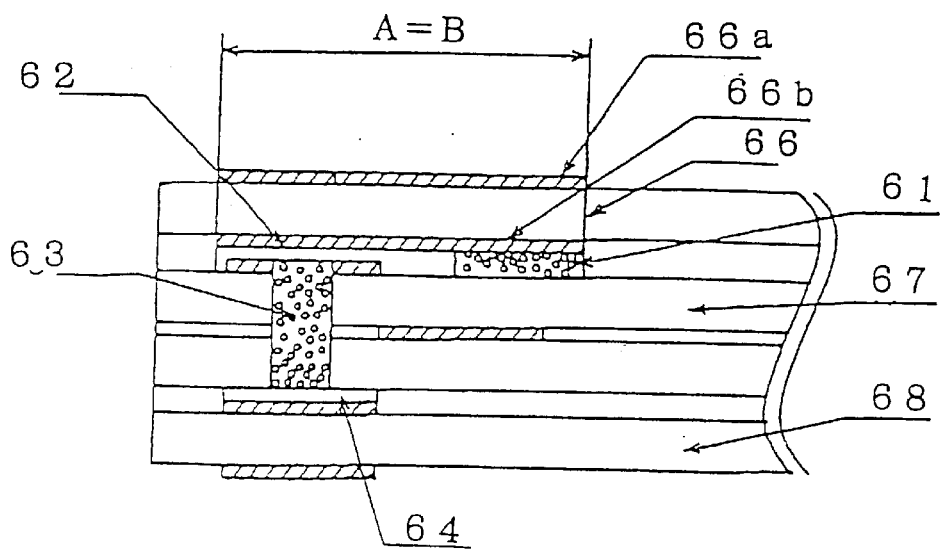
FIG. 49 shows a reference example having a long electrode in the first oxygen pump cell.

The feature of the $NO_x$ gas concentration sensor according to an embodiment of the present aspect (2—2, 2-3) is explained by referring to FIGS. 41 (A)–(C) illustrating a sensor according to an example of the present invention and to FIG. 49 illustrating a sensor according to a reference example concerning the present aspect. The present invention, however, is not limited to the sensor shown in FIG. 41. The sensor shown in FIG. 41 differs from the sensor shown in FIG. 49 in that, in the sensor of FIG. 41, the distal ends towards the second diffusion aperture 63 of the electrodes 66a, 66b of the first oxygen pumping cell 66 have been removed (A>B). Therefore, the length of each of the electrodes 66a, 66b is shorter and hence the electrode area is smaller in the sensor of FIG. 41. By the electrodes of the first oxygen pumping cell 66 being shorter in length, the oxygen concentration gradient in the first measuring chamber 2 in particular in the measuring gas flow direction (direction proceeding from a first diffusion aperture 61 towards a second diffusion aperture 63) is lowered, that is the oxygen concentration difference from one to the opposite end of the electrode 66b is reduced, while the electro-motive force generated at the distal portions of the electrodes 66a, 66b is suppressed, as shown in FIG. 41C. Moreover, with suppression of the electro-motive force generated in the electrodes 66a, 66b, the first oxygen pumping cell voltage Vp1 is reduced for reducing the temperature dependency and oxygen concentration dependency in the $NO_x$ gas concentration measurement.

This effect is brought about by the fact that the first oxygen pumping cell voltage Vp1 required for pumping out excess oxygen is lowered so that there occurs no dissociation or decomposition of the NO gas other than that by oxygen pumping-out in the first measuring chamber. Specifically, the NO gas flowing into the second measuring chamber is not decreased to prevent the $\Delta 1p_2$ (gain) from being lowered.

Moreover, since the oxygen concentration gradient in the first measuring chamber 62 is decreased, the oxygen concentration becomes constant in the vicinity of the second diffusion aperture 63, so that the concentration of oxygen introduced into the second measuring chamber 64 for measuring the $NO_x$ concentration becomes constant. That is, the concentration of oxygen pumped out in the second measuring chamber 4 becomes constant ($Ip_2$ is stabilized) such that the $Ip_2$ value depends solely on the amount of NO dissociation or decomposition.

In the sensor of the reference example shown in FIG. 49, the electrodes 66a, 66b are extended over the entire length of the first measurement chamber 62, so that, at the distal end of the first measuring chamber 62 (between the ends of the electrodes 66a and 66b), an electro-motive force opposite in direction to the first pumping cell voltage Vp1 is generated, depending on the oxygen concentration difference inside and outside the first measuring chamber 62, such that, while oxygen is pumped out at the inlet side (towards the first diffusion aperture 61) of the first measuring chamber 62, oxygen is pumped into the first measuring chamber 62 at the outlet side (towards the second diffusion aperture 63). Conversely, with the sensor shown in FIG. 41, the distal end of the electrode 66a is removed, so that, as shown in FIG. 41(C), the electro-motive force is prevented from being produced at the distal end of the first measuring chamber 62 (towards the second diffusion aperture 63 or at the outlet side of the first measuring chamber).

If at least the electrode of the first oxygen pumping cell provided on the wall surface of the first measuring chamber is too long, the first oxygen pumping cell voltage VP1 is increased to cause $NO_x$ dissociation in the first measuring chamber. If, conversely, the electrode of the first oxygen pumping cell provided on the wall surface of the first measuring chamber is too short, oxygen pumping from the first measuring chamber becomes insufficient, thus decreasing the gain of the second oxygen pumping cell current. Therefore, the length ratio of at least the electrode provided on the wall surface of the first measuring chamber to the overall length of the first measuring chamber along the flowing direction of the measuring gas in the first measuring chamber is set so that (electrode/overall length)=¼ to ¾ and preferably 2/7 to 4/7, or more preferably 5/7. In the present specification, the numerical range includes not only upper and lower limit values but also any optional intermediate values.

The $NO_x$ gas concentration sensor according to the present aspect is characterized in that the first oxygen pumping cell 66, oxygen concentration measuring cell 67 and the second oxygen pumping cell 68 are provided in respective solid electrolyte layers, as shown in FIG. 41. This reduces the leak current flowing between the cell electrodes to permit accurate control of the oxygen concentration in the first measuring chamber 62. Preferably, insulating films or layers of alumina are provided between the cells.

Preferably, heating layers for heating the sensor is layered between solid electrolyte layers. By providing the heating layer, the oxygen partial pressure measuring electrode can be maintained at a suitable temperature.

As the solid electrolyte of each cell, a solid solution of zirconia-yttria or a solid solution of zirconia-calcia is employed. The porous electrodes formed by screen printing or firing on both surfaces of the thin plate-shaped solid electrolyte layers are preferably formed of platinum or rhodium or alloys thereof exhibiting a catalytic operation. Preferably, the heat generating part of the heater is formed of a complex material of ceramics and platinum or platinum alloys, while the lead portion is formed of platinum or a platinum alloy.

The measuring method of the present invention may be applied to a CO gas sensor or a HC gas sensor, in which case the effect of $H_2O$ is reduced to permit accurate measurement of the concentration of the measuring gas, as in the case of the $NO_x$ gas sensor.

EXAMPLE C1

Referring to the drawings, a C1 example of the present aspect C is explained.

FIGS. 41A to 41C illustrate a $NO_x$ gas concentration sensor according to an embodiment of the present aspect, where FIG. 41A is a cross-sectional view taken along the long-side direction, FIG. 41B is a plan view showing a first measuring chamber and FIG. 41C is an enlarged cross-sectional view showing essential portions of the first measuring chamber. The sensor of FIG. 41 includes a layer of the first oxygen pumping cell 66 having a solid electrolyte layer and an electrode 66a (positive electrode) and a negative electrode 66b on both sides of the solid electrolyte layer, an oxygen concentration measuring cell 67 having another solid electrolyte layer and an oxygen concentration measuring cell 67 having oxygen partial pressure measuring electrodes formed on both sides of the solid electrolyte layer and a second oxygen pumping cell 68 having a third electrolyte layer and oxygen pumping electrodes on both side of the third electrolyte layer. Between the layer of the first oxygen pumping cell 68 and the layer of the oxygen concentration measuring cell 67 is defined a first measuring chamber 62 by an insulating layer on left and right sides and a solid electrolyte layer on upper and lower sides in the drawing. Similarly, a second measuring chamber 64 is defined above the second oxygen pumping cell 68. The first measuring chamber 62 is formed with the first diffusion aperture 61 and the second diffusion aperture 63 for introducing the measuring gas via a diffusion resistance. The second diffusion aperture 63 is passed through layers of the oxygen concentration measuring cell 67 and the solid electrolyte layer for establishing communication between the first and second measuring chambers 62, 64 for sending a gas containing at least $NO_x$ and $O_2$ from the first measuring chamber 62 via diffusion resistance into the second measuring chamber 64.

Between the solid electrolyte layers are formed insulating layers formed of alumina. Although not shown, heater layers for heating the sensor are bonded by cement layers for sandwiching the sensor in its entirety. The electrodes are connected to a device outside the sensor, such as a power source, vis a lead wire formed between the layers.

One of the features of the sensor is that the first measuring chamber 62 and the second measuring chamber 64 are substantially in register with each other. Another feature is that the first diffusion aperture 61 is formed on each side of the sensor, instead of on the distal end thereof, there is charged a porous material in the second measuring chamber 64, insulating films are formed between all neighboring solid electrolyte layers, and the cell electrodes are insulated from each other. The second measuring chamber 4, delimiting an open spacing, may also be charged with a porous material.

The feature of the sensor of FIG. 41 as compared to the sensor of FIG. 49 as a reference example, is that the lengths along the flowing direction of the measuring gas from the first diffusion aperture to the second aperture (in the long-side direction) of the positive electrode 66a and the negative electrode 66b of the first oxygen pumping cell 66 are shorter than the length of the first measuring chamber (A>B) and that the electrodes 66a, 66b are not formed up to the position directly above the second diffusion aperture 63.

The operation of the electrodes 66a, 66b is the same as that explained in the description of the preferred embodiment and hence is not explained here.

Using the sensor of the Example of FIG. 41 and the sensor of reference example shown in FIG. 49, the $NO_x$ gas concentration was measured. The length along the long side, width (along the short side) and thickness (in the layering direction) of the sensor are 50 mm, 4 mm and 1.3 mm, respectively. The thickness of the first oxygen pumping cell is 0.3 mm, the length B along the length and that along the short side of the fist measuring chamber of the electrodes 66a, 66b are 4 mm and 2 mm, respectively. The length A along the long side, that along the short side and height of the first measuring chamber are 7 mm, 2 mm and 50 $\mu$m, respectively. The length along the long side, that along the short side and height of the first diffusion aperture are 2 mm, 1 mm and 50 $\mu$m, respectively. The second diffusion aperture has a diameter of 1 mm and a distance thereto from the end (right end) of the first diffusion aperture is 5.5 mm. The sensor of the reference example (FIG. 49) is of the same size as the sensor of the embodiment of FIG. 41 except that the length along the long side of the electrodes 66a, 66b is 7 mm (A=B).

The method for producing the sensor used for measurement and the layout thereof are hereinafter explained. The method for producing the sensor and the layout thereof are shown in FIG. 3. The layout of the example and that of the reference example are generally the same except the different length of the electrode of the first oxygen pumping cell, as shown in FIGS. 41 and 49.

Referring to FIG. 3 (note the details of the layout of the example are different from FIG. 3), $ZrO_2$ sheets, pastes for electrodes and so forth are stacked to form a unitary sensor. Paste material such as insulating coat, electrodes, protective coating paste (printed on the fourth $ZrO_2$ green sheet) are screen printed on the respective $ZrO_2$ green sheet and laminated. The resulting shaped mass is subjected to removal of organic ingredients at 400° C. for 2 hours followed by sintering at 1500° C. for one hour.

Using the $NO_x$ gas concentration sensor, thus produced, tests were conducted for measuring the NO gas concentration in the measuring gas. The measured results are shown in Tables C1 and C2 and are summarized in FIGS. 42 to 47. The measurement conditions common to the test examples as later explained include measuring gas components NO, $O_2$ and $CO_2$ of 0 to 1500 ppm, 1 to 16% and 10%, respectively, with the balance being $N_2$, exhaust gas (measuring gas) temperature of 300° C., heater power of 18 to 25 W (20 W corresponds to the sensor temperature of 800° C.).

Refer to TABLE C1.
Refer to TABLE C2.

TEST EXAMPLE C1

Figure 42:
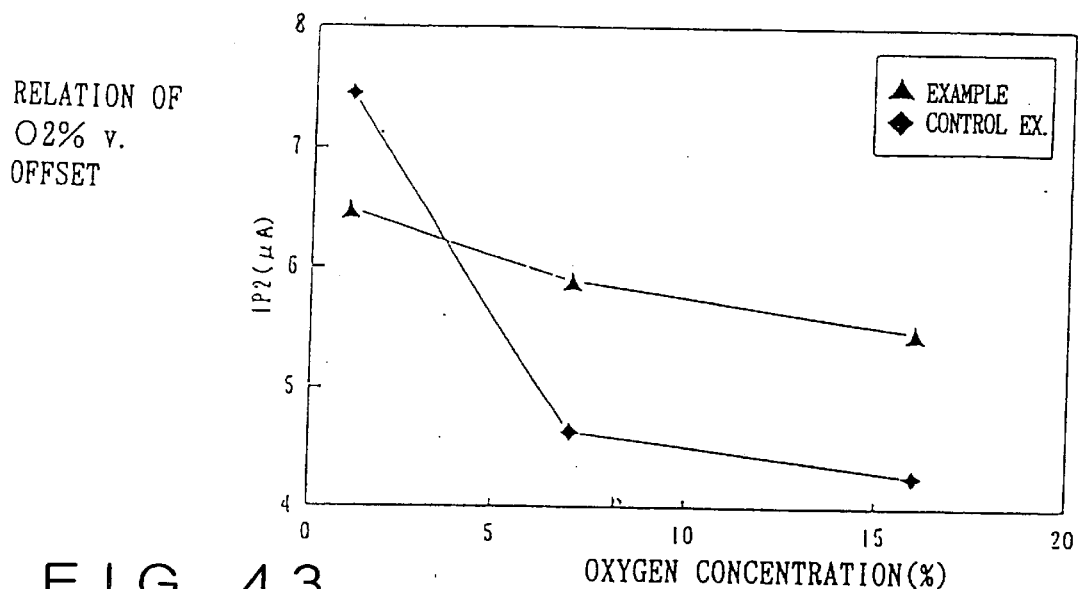

For various values of the oxygen concentration and for NO: 0%, fluctuations in the offset value of the second oxygen pumping current were measured. The offset is the amount of change $Ip_2$ ($\Delta Ip_2$) when NO is not charged into the measuring gas. A smaller value of the offset is preferred. It is desirable for the offset to be less sensitive to various extraneous conditions, such as oxygen concentration in the measuring gas or temperature in the measuring gas atmosphere and hence less susceptible to fluctuations. The offset corresponds to the concentration of the residual oxygen left unpumped in the first measuring chamber 62 (see FIG. 41). FIG. 42 shows the results of the test example C1. In FIG. 42, which is a graph showing oxygen concentration dependency of the offset of the second oxygen pumping current $Ip_2$, triangular and diamond marks denote measured data by the sensor of the example and the sensor of the reference (control) example, respectively. Referring to FIG. 42, the sensor of the embodiment undergoes $Ip_2$ changes of the order of 1 $\mu$A versus amplitude of change of 1 to 16% of the oxygen concentration, thus indicating that the oxygen concentration dependency of the gain is lower than in reference example.

TEST EXAMPLE C2

Figure 43:
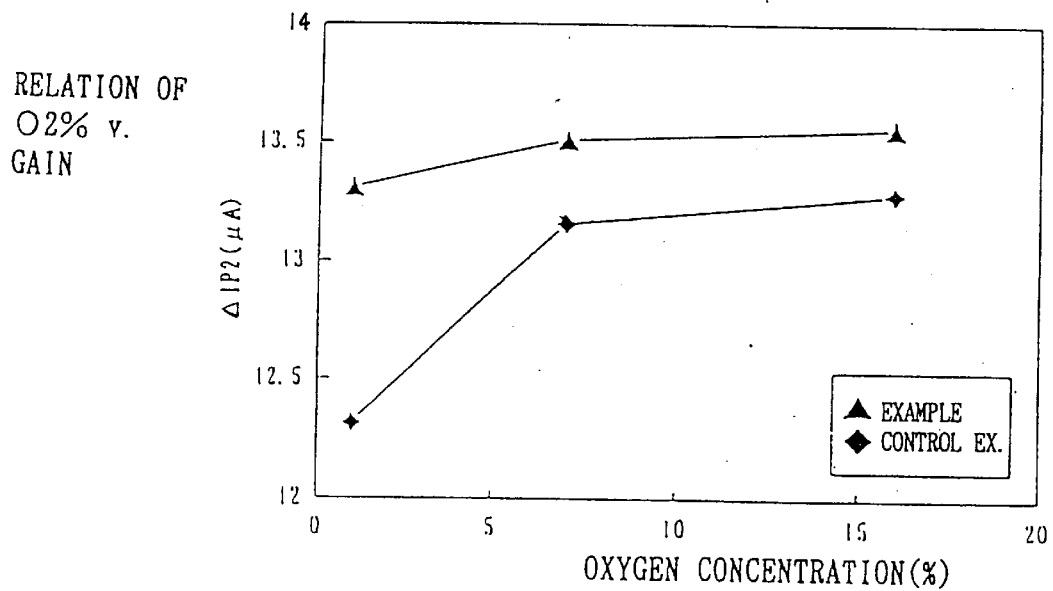

NO: 1500 ppm was charged into the measuring gas, and measurements were done of the gain of the second oxygen pumping current versus oxygen concentration values of 1 to 16%. FIG. 43 shows the results of the test example C2. In FIG. 43, which is a graph showing the oxygen concentration dependency of the second oxygen pump current $\Delta Ip_2$ triangular and diamond marks represent measured data by the sensor of the example and that of the reference (control) example, respectively. It is seen in FIG. 43 that, with the sensor of the embodiment, $Ip_2$ gain is scarcely changed versus changes of 1 to 16% of the oxygen concentrations, thus indicating that the temperature dependency is improved over the reference example.

TEST EXAMPLE C3

Figure 44:
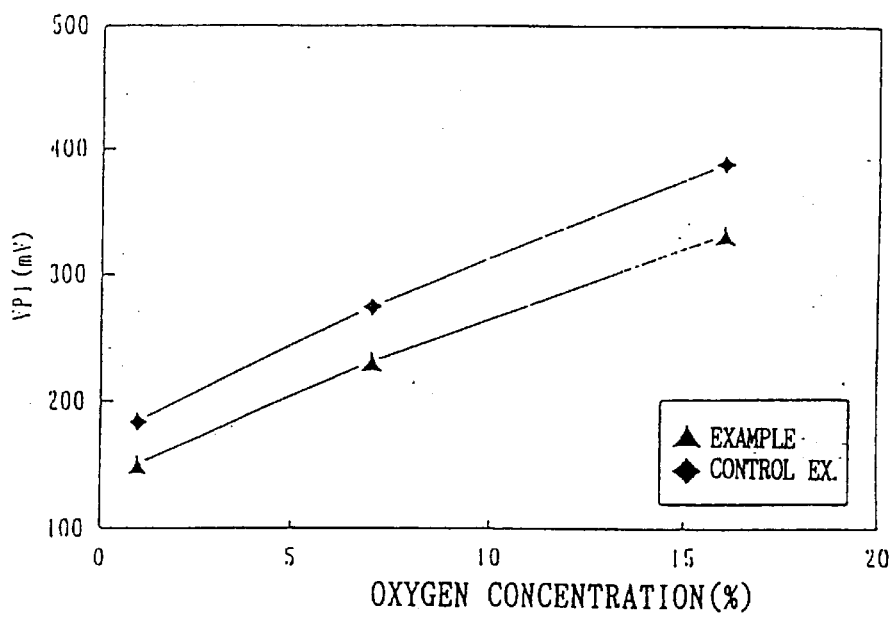

The first oxygen pumping cell voltage Vp1 across the first oxygen pumping electrodes versus changes in the oxygen concentration was measured for NO: 0%. The oxygen pumping cell voltage Vp1 is a voltage required for pumping out excess oxygen in the first measuring chamber. FIG. 44 shows the results of the test example C3. In FIG. 44, which is a graph showing the oxygen concentration dependency of the first oxygen pumping cell voltage Vp1, triangular and diamond marks denote measured data by the sensor of the example and the sensor of the reference example, respectively. It is seen from FIG. 44 that the sensor of the embodiment scarcely undergoes changes in the $Ip_2$ gain versus the change of 1 to 16% of the oxygen concentration, thus indicating that the oxygen concentration dependency of the gain is smaller than in the reference example.

TEST EXAMPLE C4

Figure 45:
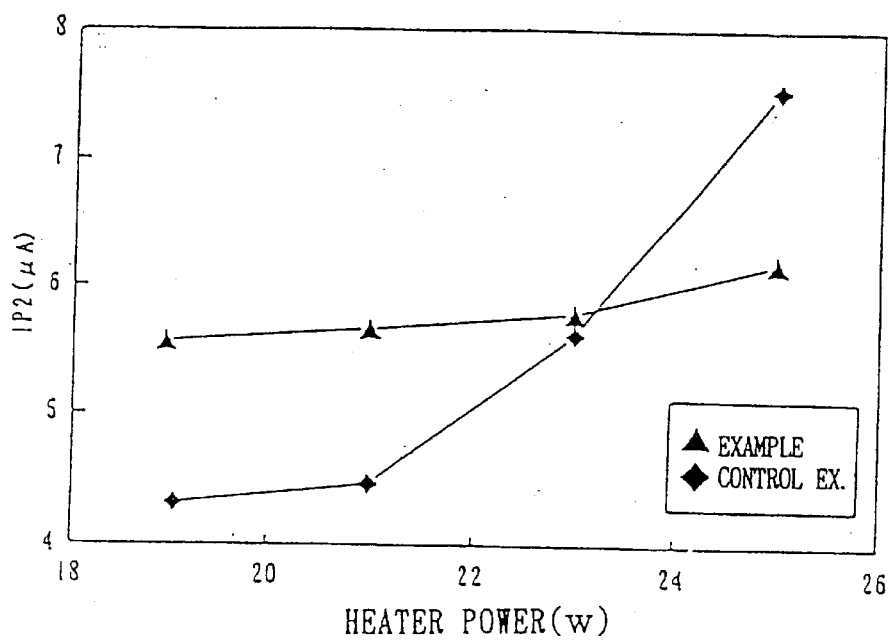

For NO: 0%, the first oxygen pumping cell voltage Vp1 between the first oxygen pumping electrodes versus changes in the oxygen concentration was measured. The oxygen pumping cell voltage is the voltage required for pumping out excess oxygen in the first measuring chamber. FIG. 45 shows the results of the test example C4. In FIG. 45, which is a graph showing the oxygen concentration dependency of the first oxygen pumping cell voltage Vp1, triangular and diamond marks denote measured data by the sensor of the example and the sensor of the reference example, respectively. It is seen from FIG. 45 that, with the sensor of the Example, the oxygen pumping cell voltage Vp1 is scarcely changed versus changes of 18 to 25 W of the heater power, thus indicating improved temperature dependency.

TEST EXAMPLE C5

For NO: 1500 ppm, NO and 7% of $O_2$ were charged into the measuring gas, and measurements were done of fluctuations in the gain value of the second oxygen pumping current $Ip_2$ for varying values of the heater power. FIG. 46 shows the results of the test example C5. In FIG. 46, which is a graph showing the temperature or heater power dependency of the second oxygen pump current $\Delta Ip_2$ triangular and diamond marks represent measured data by the sensor of the example and that of the reference example, respectively. It is seen in FIG. 7 that, with the sensor of the embodiment, $Ip_2$ gain changes become substantially constant versus changes of 18 to 25 W of the heater power, thus indicating that the temperature dependency is improved over the reference example.

TEST EXAMPLE C6

For NO: 0%, 7% of $O_2$ was charged into the measuring gas, and measurements were made of the gain of the second oxygen pump current versus varying values of the heater power. FIG. 8 shows the results of test example C6. In FIG. 47, which is a graph showing the temperature or heater power dependency of the second oxygen pump voltage Vp1, triangular and diamond marks represent measured data by the sensor of the example and that of the reference example, respectively. It is seen that, in the heater of the example, Vp1 has been significantly reduced versus changes in heater power of 18 to 25 W.

Figure 48:
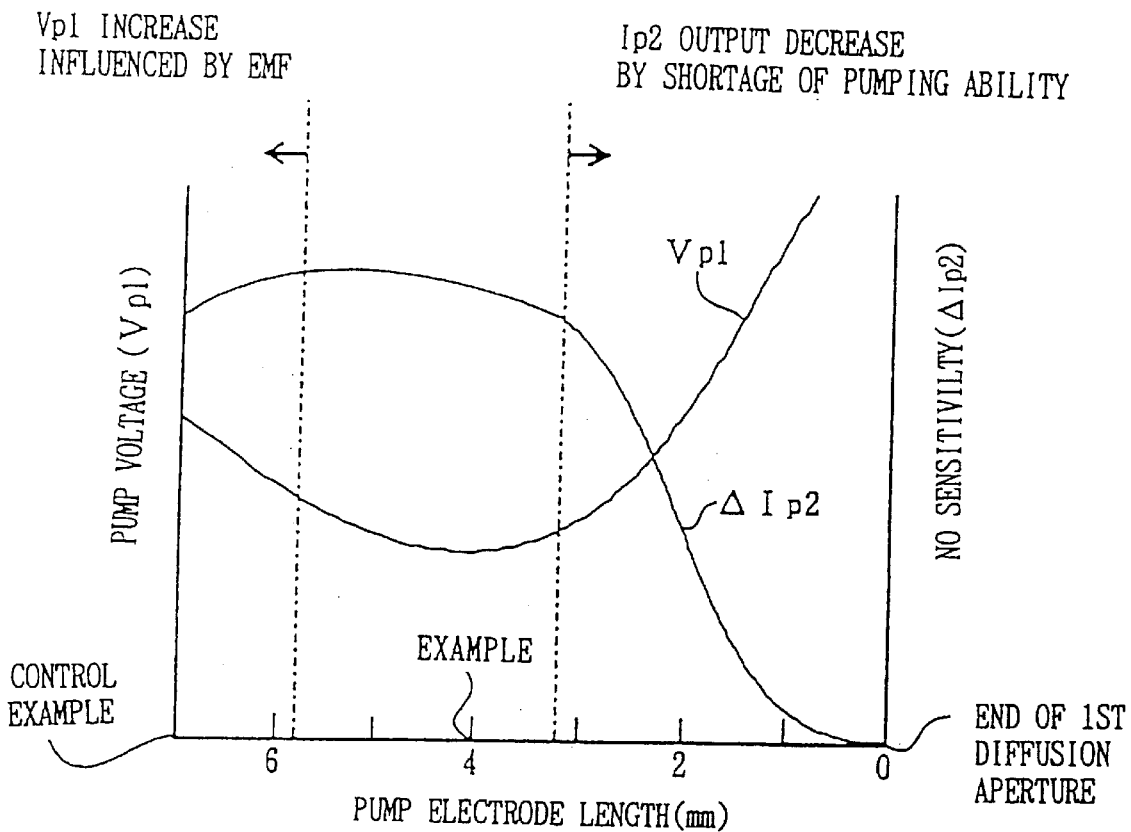

From the results of the above reference examples C1 to C6 (FIGS. 42 to 48), it is seen that, if the electrodes of the first oxygen pumping cell (at least the electrode towards the first measuring chamber) is longer than the length of the first measuring chamber, the first oxygen pumping cell voltage Vp1 tends to be increased under the effect of the electromotive force generated on the distal end of the first oxygen pumping cell (the distal end of the electrode opposite to the first diffusion aperture), with the effective voltage being then decreased, because the pumped-in oxygen in the first measuring chamber is pumped out for compensating for the decreased effective voltage for maintaining the oxygen concentration in the first measuring chamber at a pre-set concentration. It is also seen that, if the electrodes of the first oxygen pumping cell is shorter than the length of the first measuring chamber, the gain of the second oxygen pumping cell voltage Vp1 tends to be decreased due to insufficient pump capability (more oxygen is diffused towards the second measuring chamber so that measurement of a trace amount of the $NO_x$ gas concentration becomes inaccurate). FIG. 48 shows that the length of the first oxygen pumping electrode equal to 4 mm for the length of the first measuring chamber of 7 mm, that is the ratio of the electrode length to the first measuring chamber length of 4/7, is particularly preferred. The length of the first oxygen pump current of 2 to 5.4 mm is preferred, while the length of 3.5 to 5 mm is particularly preferred.

In the state where the electrode of the first oxygen pumping cell is so long as to cover the second diffusion aperture, it is seen that the generated electro-motive force EMF gives rise to increase the first oxygen pumping cell voltage Vp1 and decrease $\Delta Ip2$. On the other hand, if the electrodes of the first oxygen pumping cell are too short, it is seen that the Ip2 output will decrease because of shortage in the pumping capability.

It is seen from above that, with the $NO_x$ gas concentration sensor of the present aspect C, the electro-motive force produced in the first measuring chamber is suppressed, while the first oxygen pumping cell voltage Vp1 is decreased and the dissociation and decomposition of the NO gas in the first measuring chamber are suppressed, thus improving oxygen dependency and temperature dependency of $NO_x$ gas concentration measurement for enabling more accurate measurement of the $NO_x$ gas concentration.

Figure 50:
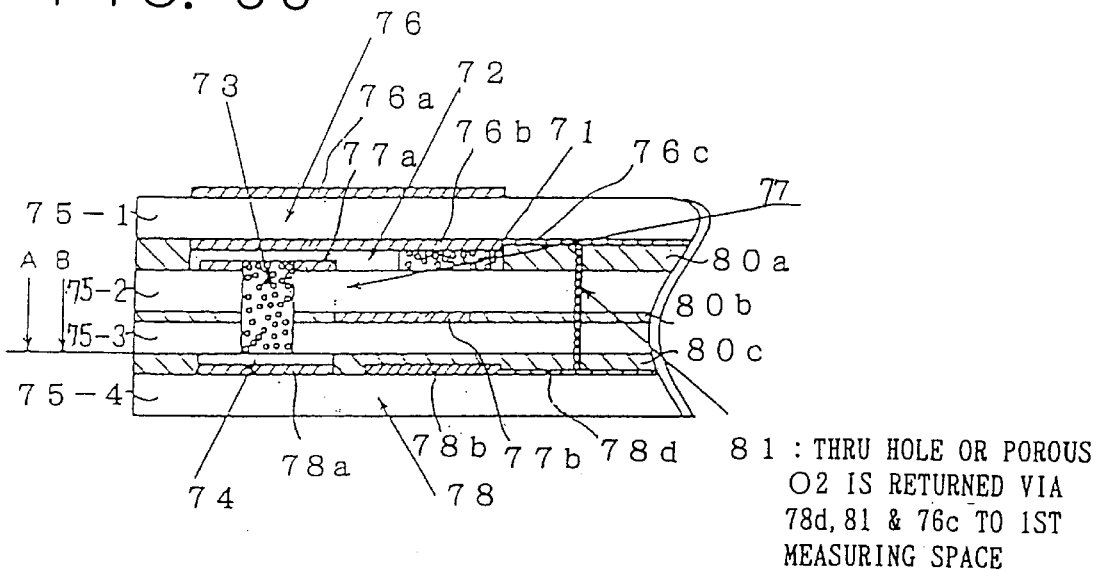
FIGS. 50–52 show another embodiment of the present invention.

The sensor shown in FIG. 50 includes a first oxygen concentration measuring cell 76, a second oxygen concentration measuring cell 77 and a second oxygen pumping cell 78, layered in this order. The first oxygen pumping cell 76 has a pair of electrodes 76a, 76b formed on both sides of a solid electrolyte layer 75-1. The second oxygen concentration measuring cell 77 has a pair of oxygen partial pressure measuring electrodes 77a, 77b formed on both sides of a solid electrolyte layer 75-2, while the second oxygen pumping cell 78 has a pair of electrodes on the surfaces of the solid electrolyte layers 75-3 and 75-4, that is an electrode 78a inside of the second measuring chamber of the second oxygen pumping cell 78 and an electrode 78b outside of the second measuring chamber of the second oxygen pumping cell 78. Between the solid electrolyte layers 75-1, 75-2, 75-3 and 75-4 are formed insulating layers 80a, 80b and 80c. In an interlayer spacing between the first oxygen pumping cell 6 and the oxygen concentration measuring cell 77 is delimited a first measuring chamber 72 by left and right insulating layers 80a and upper and lower solid electrolyte layers 75-1 and 75-2. Similarly, above the second oxygen pumping cell 78, a second measuring chamber 74 is delimited by the insulating layer 80c and the solid electrolyte layers 75-3 and 75-4. On one side of the first measuring chamber 72 on both sides along the short-side direction of the sensor (on the front side and back sides in FIG. 50) is formed a first diffusion aperture 71 having diffusion resistance. On the opposite side of the first measuring chamber 72 is formed an opening of the second diffusion aperture 73 at a spacing from the first diffusion aperture 71. The second diffusion aperture 73 is passed thorough the oxygen concentration measuring cell 77 and the solid electrolyte layer 75-3 for establishing communication between the first and second measuring chambers 72, 74 with diffusion resistance.

Figure 51:
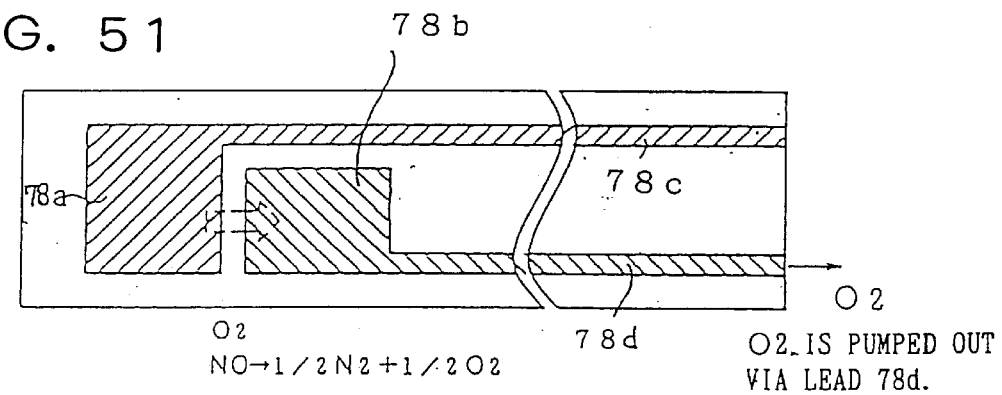

In the present sensor, the electrodes 78a and 78b of a porous material, such as platinum or rhodium alloy, are formed on the same surface of the solid electrolyte layer 75-4 of the second oxygen pumping cell 78. Although the electrodes 78a and 78b are isolated from each other by the insulating layer 80c, oxygen ion conduction occurs via the solid electrolyte layer 75-4 to produce the current $Ip_2$. The electrode 8b is prevented by the solid electrolyte layer 75-4, an insulating layer 80c and the lead portion 78d from having direct contact with air outside the sensor, and can discharge oxygen pumped out by the second oxygen pumping cell 78 via the porous lead portion 78d having the diffusion resistance. To the electrodes 78a, 78b are electrically connected a lead 78c, not shown, and a lead 78d, respectively. The lead portion 78d electrically connected to the electrode 78b outside the second measuring chamber 74 is porous to permit oxygen ions to be diffused. Thus, oxygen decomposed from the $NO_x$ gas and pumped out from electrode 78a to electrode 78b by the second oxygen pumping cell 78 as indicated by arrow in FIG. 51 is discharged via lead portion 78d.

This oxygen, discharged via the lead portion 78d, is discharged via the porous lead portion 76c of the first oxygen pumping cell 76 into the first measuring chamber 72 via a through-hole or pores 81 as a gas channel communicating the lead portions 78d with the porous lead portion 76c of the first oxygen pumping cell 76 shown in FIG. 50 and thence into air outside the sensor.

With the present sensor, in which the electrode 78b as a counter-electrode of the electrode 78a of the second oxygen pumping cell 78 is mounted in the inside of the device (between the layered solid electrolytes), the solid electrolyte layer 75-4 and the insulating layer 80c become protection means for the electrode 78b, while the lead portion 78d becomes the diffusion resistance means. Thus the electrode 78b is isolated from the atmosphere of the measuring gas (exhaust gas) so as to be out of direct contact with outside air, while pumped-out oxygen is pooled in the vicinity of the electrode 78b, thus stabilizing the oxygen concentration around or in the vicinity of the electrode 78b and the electro-motive force generated across the electrodes 78a, 78b of the second oxygen pumping cell 78. Moreover, since the generated electro-motive force is stabilized, the effective pump voltage of the pump voltage Vp2 impressed across the second oxygen pumping cell 8 (Vp2—electro-motive force) is stabilized for decreasing oxygen concentration dependency of measurement of the $NO_x$ gas concentration.

The sensor shown in FIG. 50 also has a merit that the electrodes 78a, 78b of the second oxygen pumping cell 78 can be printed at a time.

In addition, the paired electrodes of the first oxygen pumping cell 76, oxygen pumping cell 77 and the second oxygen pumping cell 78 can be connected to outside via inter-layer lead portions. In the measurement examples, as later explained, the electrodes 76a, 76b of the first oxygen pumping cell 76 and the electrodes 78a, 78b of the second oxygen pumping cell 78 are connected to a power source and to an ammeter, respectively, while the electrodes 77a, 77b of the oxygen concentration measuring cell 77 is connected to a voltmeter. This configuration is shown in FIG. 7 of our senior JP Patent Application No. 8-160812.

Figure 52:
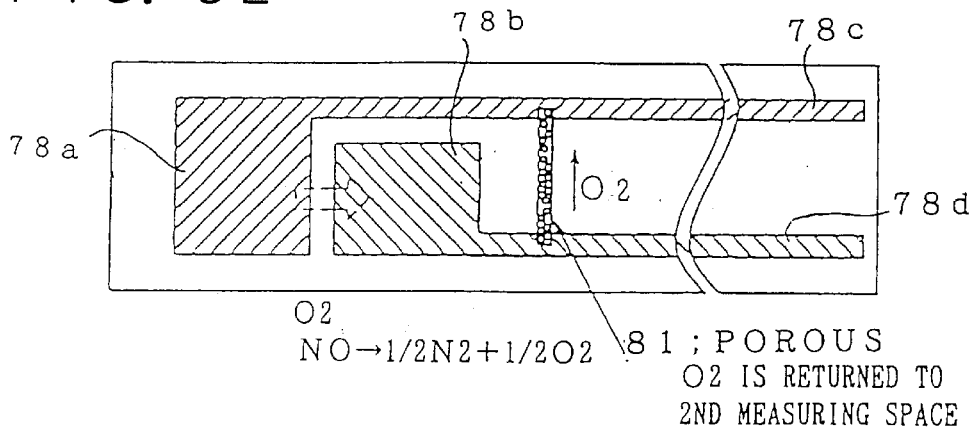

FIGS. 51 and 52 are a plan view and a cross-sectional view showing a preferred embodiment of the above-described $NO_x$ gas concentration sensor. That is, FIGS. 51 and 52 correspond to the plan view and the cross-sectional views shown by arrows A and B in FIG. 50. The sensor of FIG. 51 differs from the sensor of FIG. 50 in that the lead portion 78d is contacted with the air outside of the sensor (atmosphere or atmosphere of the measuring gas) so that the outside communicates with the electrode 78d via diffusion resistance. The sensor of FIG. 52 differs from the sensor of FIG. 50 in that the porous layer (film) 81 formed between solid electrolyte layers establishes communication between the leads 78c and 78d and in that oxygen pumped out by the second oxygen pumping cell is recycled to the second measuring chamber 74 via the porous layer (film) 81 and the porous lead portion 78c and electrode 78a.

[Method for preparing a pintng paste for an inner electrode 76b in a first oxygen ion pump cell]

The following desirable producing method may be used in place of the above-mentioned method for producing a printing paste for the inner electrode 76b of the first oxygen ion pump cell. (2') For an inner electrode 76b of a first oxygen ion pump cell: Of the paired electrodes 76a, 76b provided on the first oxygen ion pump cell 76, the electrode 76b provided in the inside of the first measurement chamber 72 is explained as to the material. As a powdered material of the solid electrolyte having oxygen ion conductivity, carrying Au as the first constituent of the electrode, $ZrO_2$ powders partially stabilized by yttria (referred to as partially stabilized $ZrO_2$ powders) were used. The partially stabilized $ZrO_2$ powders, with a particle size of 0.1 to 50 μm, were impregnated in 1.8 gs. of gold chloride acid solution with an Au content of 30.520 wt % and dried at 120° C. for seven hours. The resulting mass was fired at 800° for three hours to produce 3.36 gs of powders comprised of fine Au particles (with a particle size of less than 1 μm) carried on the partially stabilized $ZrO_2$ powders. A paste containing these powders were prepared as follows: 3.36 gs of powders, obtained on having fine Au protein carried on the partially stabilized $ZrO_2$ powders, were crushed by a crusher for 12 hours and mixed with 20 gs of porous Pt powders (with a particle size of 1 to 50 μm) and a suitable amount of an organic solvent. After crushing the resulting mass for four hours in a crusher or a pot mill, 2 gs of a binder dissolved in 20 gs of an organic solvent were added to the crushed product. The resulting mass was added to with 5 gs of a viscosity controller and milled for four hours to a paste having a viscosity of 140 Pa.s.

In the electrode structure, thus obtained, Au components are carried by particles relatively coarser than the Au particles (that is zirconia particles as main electrode components) so that the Au components are dispersed finely. By adding a component carried by a catalyst adjustment method on the powders of a oxygen ion conductive solid electrolyte, in addition to the porous powders, such as Pt powders, the interface resistance generated across particles is lowered to improve the oxygen expelling capability. For example, one or more of Au, Ag, Ni, Mn, Co, Cu, Ba, Mg, Ca, Na, K and Li may be selected and used as NOx dissociation suppressing capability, other than fine Au particles, as film, if so desired.

Figure 53:
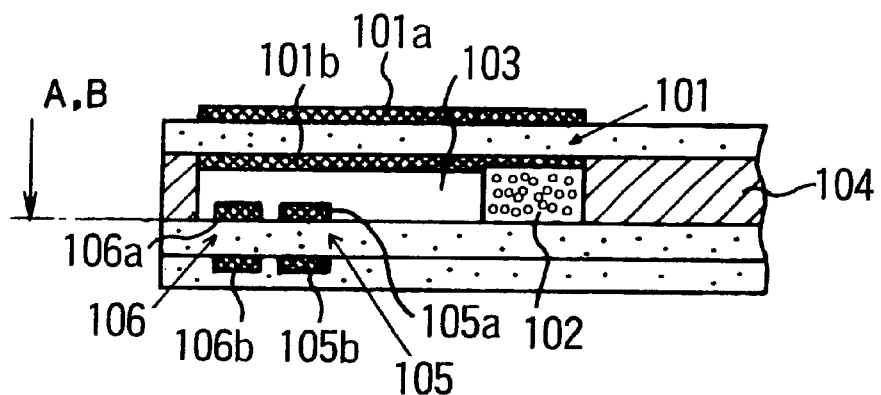
FIG. 53 is a cross-sectional view along the length of a NOx gas sensor according to another embodiment of the second and fourth aspects of the invention.
Figure 54:
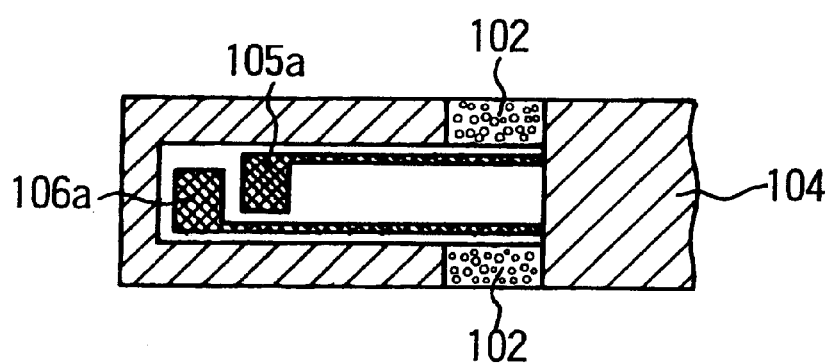
Figure 54:
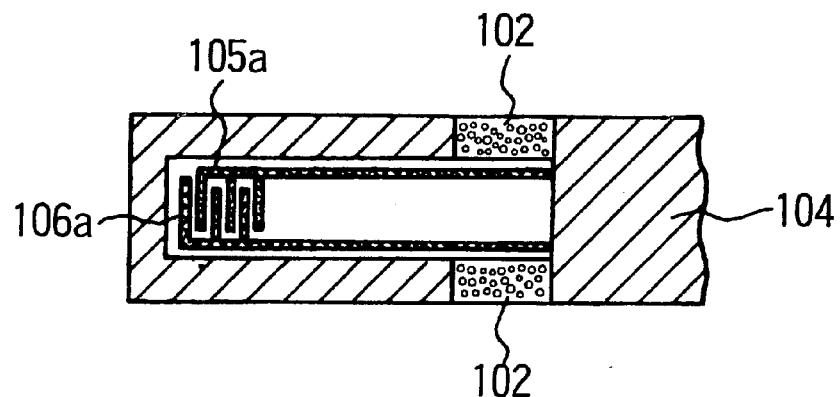

An embodiment of a NOx concentration sensor according to the first aspect of the present invention is explained. A sensor according to the first aspect of the present invention shows in FIGS. 53 and 54(A) is comprised by three oxygen ion conductive solid electrolyte layers making up a ceramic body, and includes a first oxygen ion pump cell 101, a second oxygen ion pump cell 106, an oxygen concentration sensor cell 105 and a flow channel 103 defined in the ceramic body. Between the first and second solid electrolyte layers defined a flow channel 103 having its end face having a normal line in the longitudinal direction surrounded by an insulating layer and also having its lateral surface having a normal line in the short-side direction surrounded by the insulating layer and a diffusion resistance 102. On the outer side of the first solid electrolyte layer is formed an outer electrode 101a of the first oxygen ion pump cell 101. On the inner side of the first solid electrolyte layer is formed an inner electrode (second electrode or an electrode for concentrating NOx) to the substantially same length as the entire longitudinal length of the flow channel 103 for facing the flow channel 103. On the second solid electrolyte layer are formed an oxygen concentration sensor electrode (first electrode) 105a and an inner electrode (third electrode, that is an electrode for decomposing and dissociating NOx) of the second oxygen ion pump cell 106a, for facing the flow channel 103. Also, an oxygen reference electrode 105b and an outer electrode 106b of the second oxygen ion pump cell 106, sealed between the second and third solid electrolyte layers, are formed on the second solid electrolyte layer for not facing the flow channel 103. The electrodes 105b and 106b communicate with the atmosphere via a lead having a pre-set diffusion resistance. The oxygen concentration sensor electrode 105a and the inner electrode 106a of the second oxygen ion pump cell 106 are arranged in proximity to each other at the remotest position from the diffusion resistance (such as a porous alumina layer) 102 arranged at an entrance in the flow channel so that electrodes 105a, 105b are substantially the same atmosphere and so that there is no diffusion resistance between the electrodes 105a, 106a (see FIG. 54A). The electrodes 101a, 101b, 105a, 105b, 106a and 106b are electrically connected to a lead shown in FIG. 54 to permit outputs of these electrodes to be taken out or controlled. Between the solid electrode layers are formed insulating layers, not shown, for preventing leak currents from flowing between the leads. Preferably, an extremely small current is supplied via a lead to the oxygen concentration reference electrode 105b which then serves as an auto-generating reference electrode. In this case, an electrical voltages preferably impressed in a direction of transporting oxygen from the electrode 105 towards the electrode 105b for increasing the oxygen concentration in the vicinity of the porous oxygen concentration reference electrode 106b. The arrangement may be so made that the current is not supplied to the oxygen concentration reference electrode, with the atmosphere in the vicinity of the oxygen concentration reference electrode 106b (atmosphere of the reference gas introducing space) then being air.

In the above embodiment, the oxygen concentration in the measurement gas can be measured from the current flowing between the electrodes 101a, 101b of the first oxygen ion pump cell 101. The path between the electrodes 101a, 101b may also be controlled by current instead of by voltage. Although the flow channel 103 is formed as a void, it may be charged entirely or partially with a diffusion resistance material. The flow channel 103, extending between the two solid electrolyte layers, may also be extended between the insulating layer and the solid electrolyte layer. The lengths of the electrodes 101a, 101b, substantially equal to the entire length of the flow channel 103, may also be not equal thereto, that is, the ratio of the lengths of the electrodes 101a, 101b and the length of the flow channel 103 may be of a pre-set value.

Figure 55:
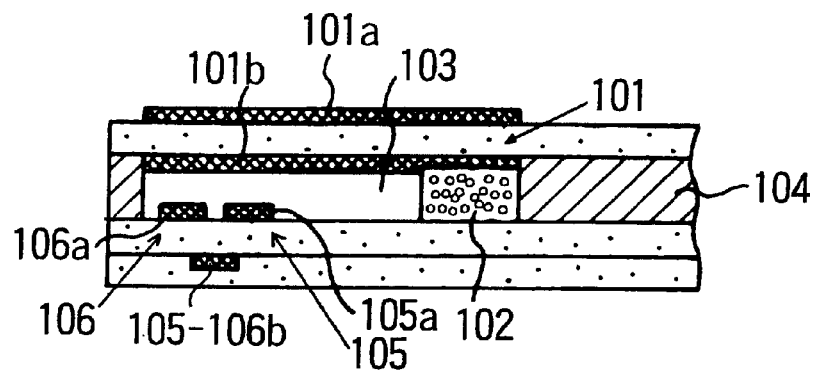
FIG. 55 shows a modification of the sensor shown in FIG. 54.
Figure 56:
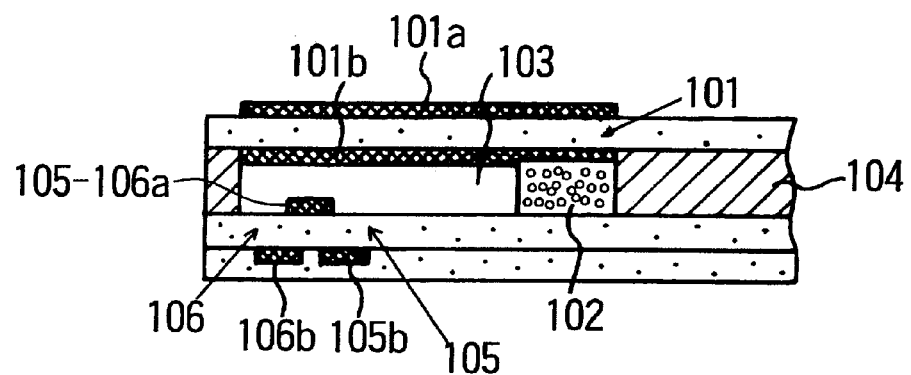
FIG. 56 shows another modification of the sensor shown in FIG. 54.

As a modification of the above embodiment, the oxygen concentration reference electrode and the outer electrode of the second oxygen ion pump cell may be used in common (as an outer common electrode 105–106b), as shown in FIG. 55. The NOx gas concentration sensor may also be designed so that the oxygen concentration reference electrode and the inner electrode of the second oxygen ion pump cell may be used in common (as an inner common electrode 105–106a), as shown in FIG. 56.

Test Examples

Using a NOx gas concentration sensor, generally shown in FIG. 55, in which the oxygen concentration sensor electrode 105a and the inner electrode 106a of the second oxygen ion pump cell in the flow channel 103 are comb-shaped as shown in FIG. 54B, a variety of tests were conducted.

Test Example A

Figure 58:
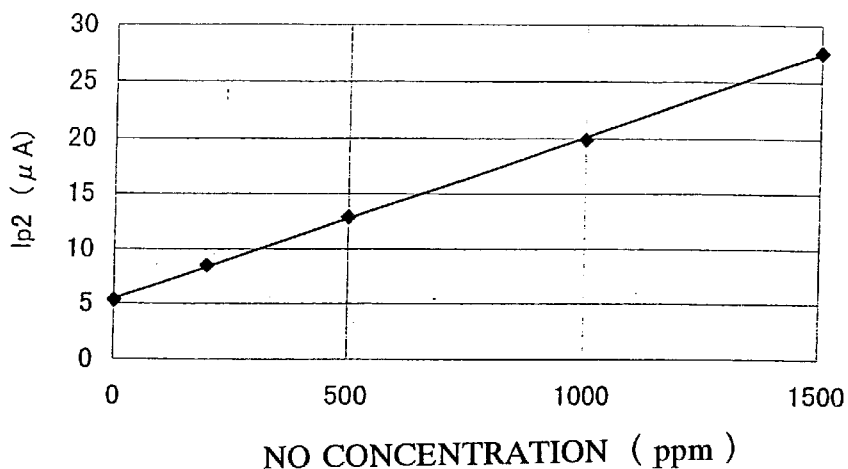
FIG. 58 shows the relation between the sensor output Ip2 of the NOx gas sensor shown in FIGS. 55 and 54B and the NO gas concentration.

To this NOx concentration gas sensor, an external circuit was attached so that the voltage can be applied across the electrodes 101a, 101b based on the detected oxygen concentration in the flow channel 103 and so that measurement can be made of the current flowing across the electrodes 106a, 106b, and the measurement gas containing the NO gas of a pre-set concentration gas charged into this sensor. The test conditions included the composition of the measurement gas of NO: 0 to 1500 ppm; $O_2$: 1%, and $N_2$ balance; the measurement gas temperature of 300° C.; and the temperature of the sensor portion: 800° C. The sensor portion was heated to this temperature by the heater layer mounted on the outer sensor layer. FIG. 58 shows the relation between the concentration of the injected NO and the current Ip2 (sensor output) proportionate to the concentration of the NO gas flowing between the inner electrode and the outer electrode of the second oxygen ion pump cell. In FIG. 58, Ip2 is changed linearly versus the changes in the NO concentration. Therefore, the No gas concentrations can be measured by measuring Ip2.

Figure 57:
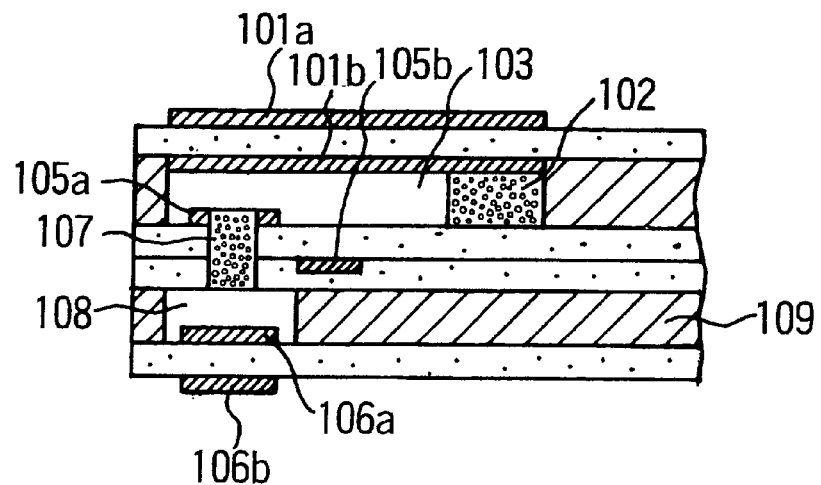
FIG. 57 is a longitudinal cross-sectional view of a NOx gas concentration sensor as a reference example for the sensors shown in FIGS. 53 to 56.

Also, using the sensor of the above embodiment and a NOx gas concentration sensor proposed by the present inventors as a reference example, measurements were made of the responsiveness and the oxygen concentration dependency of the detector output. The sensor the comparative example shown in FIG. 57 is comprised of four solid electrolyte layers, layered together, and includes two diffusion resistance units 102, 107 and two flow channels 103, 108, with the lateral side of the second flow channel 108 being partially surrounded by an insulating layer 109. The oxygen concentration sensor electrode 105a and the second electrode 106a are provided in different areas (at a separation from each other) and the oxygen concentration sensor electrode 105a detects the oxygen concentration in the first flow channel 103 instead of detecting the oxygen concentration in the second flow channel 108. In the sensor of the comparative example, the oxygen in the measurement gas diffused via first diffusion resistance unit 102 into the first flow channel 103 is sent out by the outer electrode 101a and the inner electrode 101b of the first oxygen ion pump cell 101 based on the potential of the oxygen concentration sensor electrode 105a, such that the gas controlled to an oxygen concentration to less than a pre-set value is diffused via second diffusion resistance unit 107 into the second flow channel 108. A pre-set voltage is impressed across the inner electrode 106a and the outer electrode 106b of the second oxygen ion pump cell 106 so that a current proportionate in the NOx concentration flows through the electrodes 106a, 106b.

Test Example B

Figure 59:
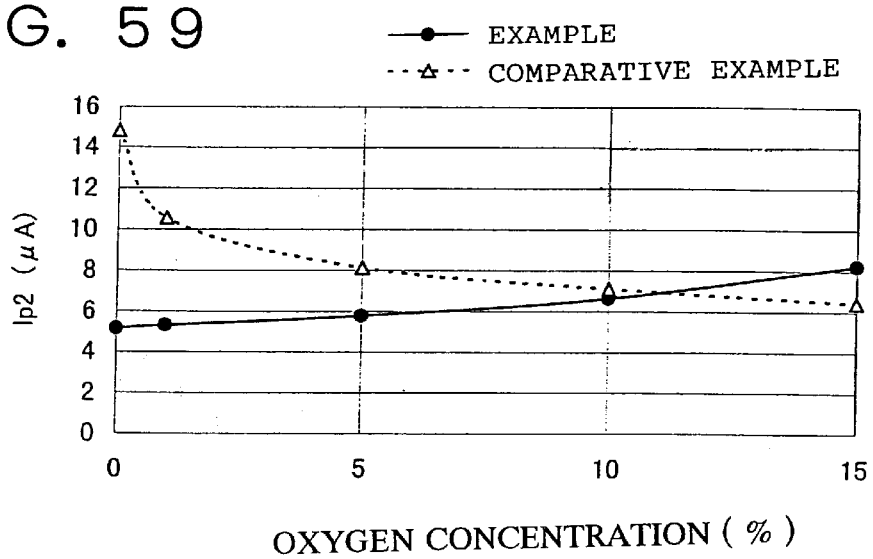
FIG. 59 shows the oxygen concentration dependency of the sensor output in the sensor shown in FIGS. 55 and 54b and the oxygen concentration dependency of the sensor output in the sensor shown in FIG. 57.

The NOx concentration gas sensor of the present example and the NOx concentration gas sensor of the reference example were each fitted with an external circuit as described above and measurement gases free of the NO gas were injected with variable oxygen concentrations. The text conditions included the test gas composition of NO: 0 ppm; $O_2$: 0 to 15%; $CO_2$: 10%; and $N_2$: balance; test gas temperature, 300° C.; and the sensor temperature, 800° C. FIG. 59 shows the relation between the oxygen concentration in the measurement gas and Ip2. The solid line and the broken line denote test data of the example and the reference example, respectively. It is seen from FIG. 59 that the variation of Ip2 of the example is on the order of 3 $\mu$A versus the variation of 0 to 15% of the oxygen concentration giving a reduced value as compared to the reference example. Thus it is seen that the oxygen partial pressure on the inner electrode in the second oxygen ion pump cell is detected and controlled more accurately.

The operation and measurement conditions are as follows. The first pump cell (Vp1 cell) is applied with a controlled voltage (basically –2 to 2 V) so as to keep the Vs cell at a preset value. The second pump cell (Vp2 cell) is applied with a voltage of 400 to 500 mV, preferably 430 to 480 mV, with a set voltage being 450 mV. The Vs cell is applied with a set potential between the oxygen detecting electrode and the oxygen detecting reference electrode, at a value 300 to 450 mV, preferably 340 to 370 mV, with a set value being 350 mV.

Test Example C

The rising characteristics of the sensor outputs of the above example and the reference example were checked with the NO gas concentration of 1500 ppm instead of 0. The measurement gas composition was NO: 0–1500 ppm; $O_2$ 10%; $N_2$: balance; detection gas temperature, 300° C.; and the sensor temperature, 800° C.

Figure 60:
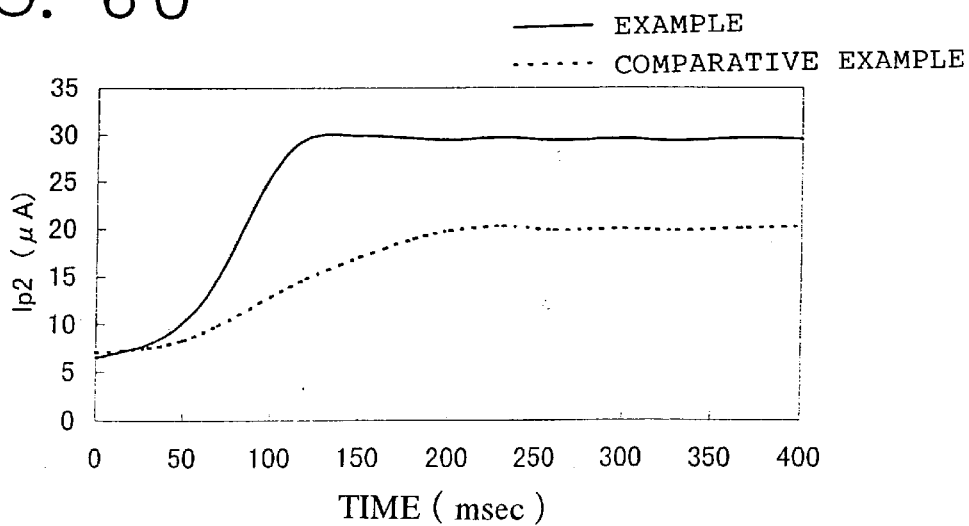
FIG. 60 show the responsiveness of the sensor shown in FIGS. 55 and 54B and that of the sensor shown in FIG. 57.

FIG. 60 shows the responsiveness of the example and that of the reference example when the NO gas concentration was changed from 0 ppm to 1500 ppm. The solid line and the broken line denote test data of the example and the reference example, respectively. It is seen from FIG. 60 that the response time of the example is about half of that of the reference example, so that the sensor of the example permits the NO concentration to be measured with good responsiveness.

Figure 62B:
Figure 62A:
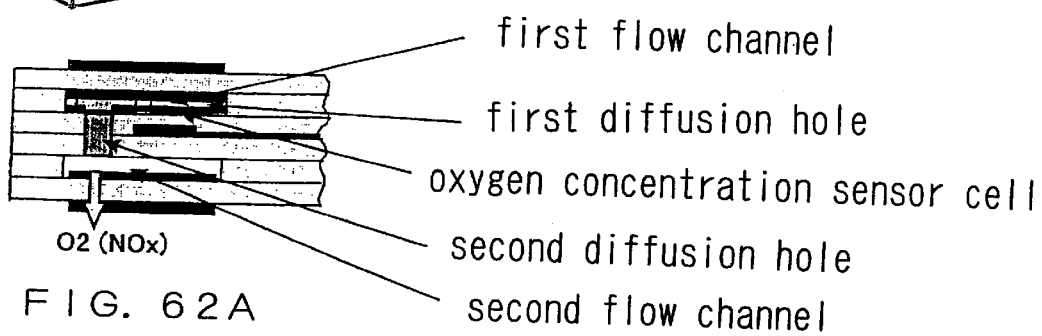

Meanwhile, the effective pump voltage effectively operating on a second oxygen ion pump cell (Vp2 effec.) is given by VP2effec.=VP2 (applied voltage)–EMF (electromotive force due to differential oxygen concentration across the inner and outer sides of the second flow passage). Thus, referring to FIGS. 61A or 61B, the value of the EMF is varied in case of an exposed electrode type for VP2 (type 1; an example of which is shown in FIGS. 62A to 62C) while being constant for Vp2 (type 2; an example of which is shown in FIGS. 63A to 63D). On the other hand, the value of VP2effc. is varied or constant for an exposed electrode type for Vp2 (type 1) or an enclosed electrode type for Vp2 (type 2), respectively. That is, if, with the exposed electrode type for Vp2 (type 1), the oxygen concentration in the measurement gas is varied, the EMF due to the differential oxygen concentration inside and outside the flow passage is varied. Since the voltage applied across the second oxygen ion pump cell is constant, the effective pump voltage Vp2effec. is ultimately varied as a result of variations in the EMF. Thus, concentration measurement employing the exposed electrode type for Vp2 is susceptible to variations in the oxygen concentration in the measurement gas, that is, the sensor output exhibits high oxygen concentration dependency.

Figure 63B:
Figure 63A:
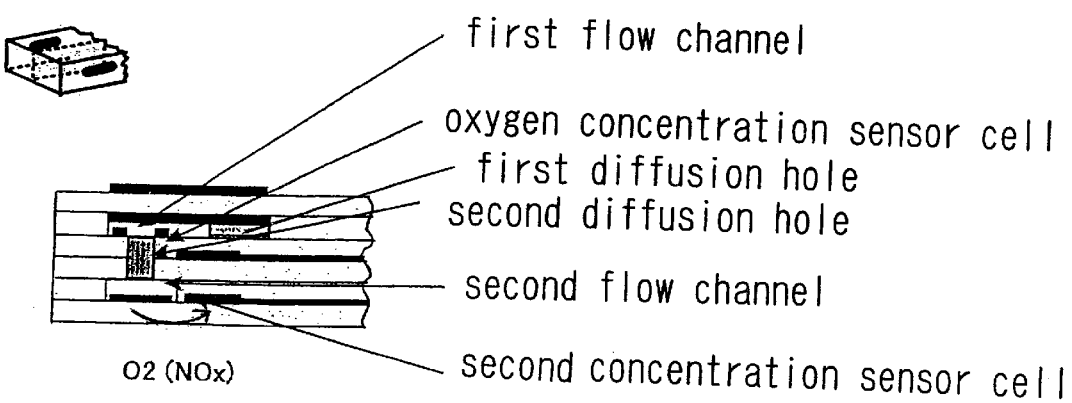

FIGS. 62A and 62B are partial layout views for illustrating an example of a NOx gas concentration for the exposed electrode type for Vp2 (type 1). FIGS. 63A and 63B are partial layout views for illustrating an example of a NOx gas concentration for the enclosed electrode type for Vp2 (type 2). The type 1 sensor has four first diffusion holes (two diffusion holes are formed for extending along the length of the sensor on both lateral sides thereof) as shown in FIG. 62B. However, only two diffusion holes also suffice, as shown in FIG. 3.

Figure 64:
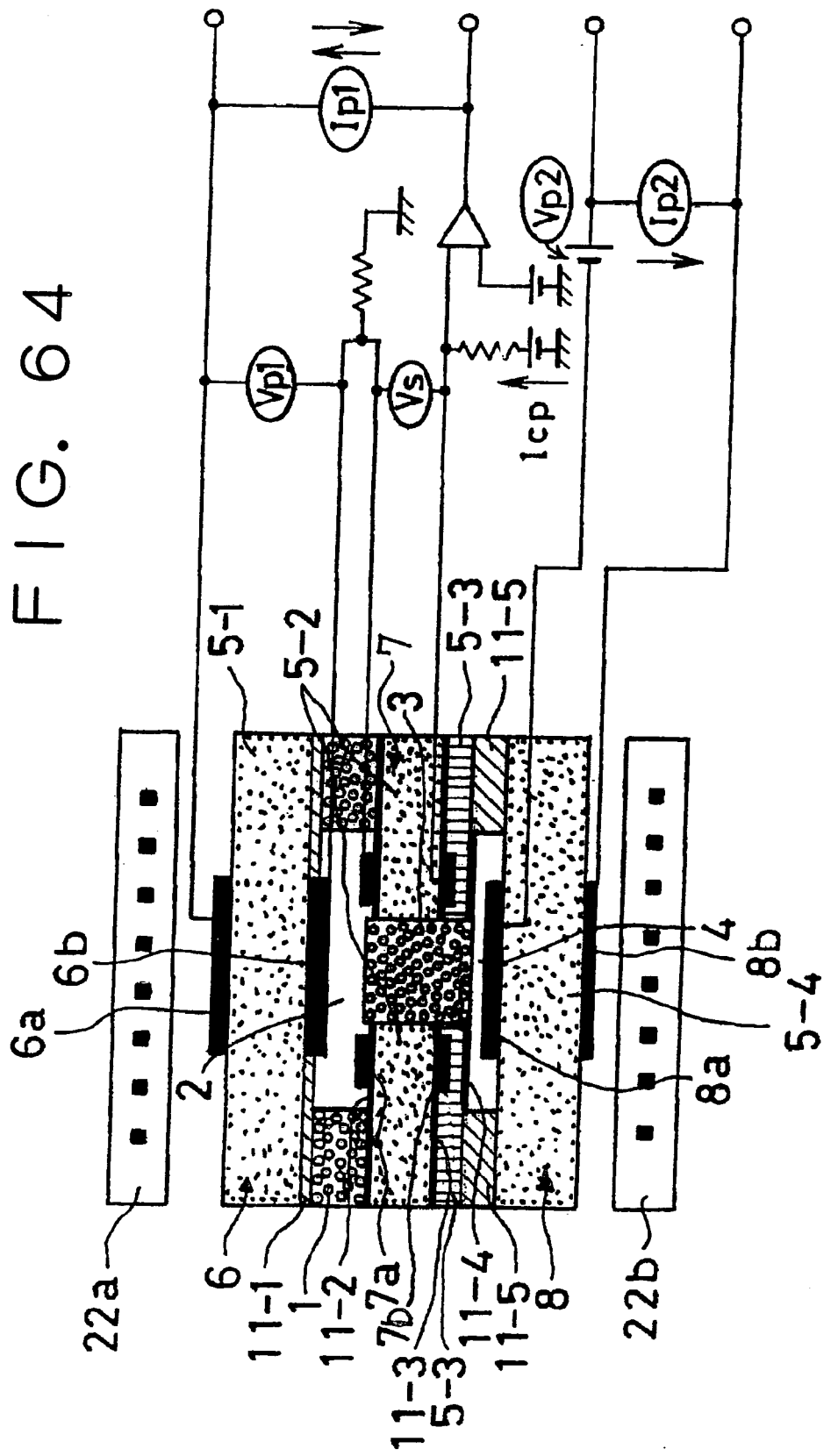
Figure 65:
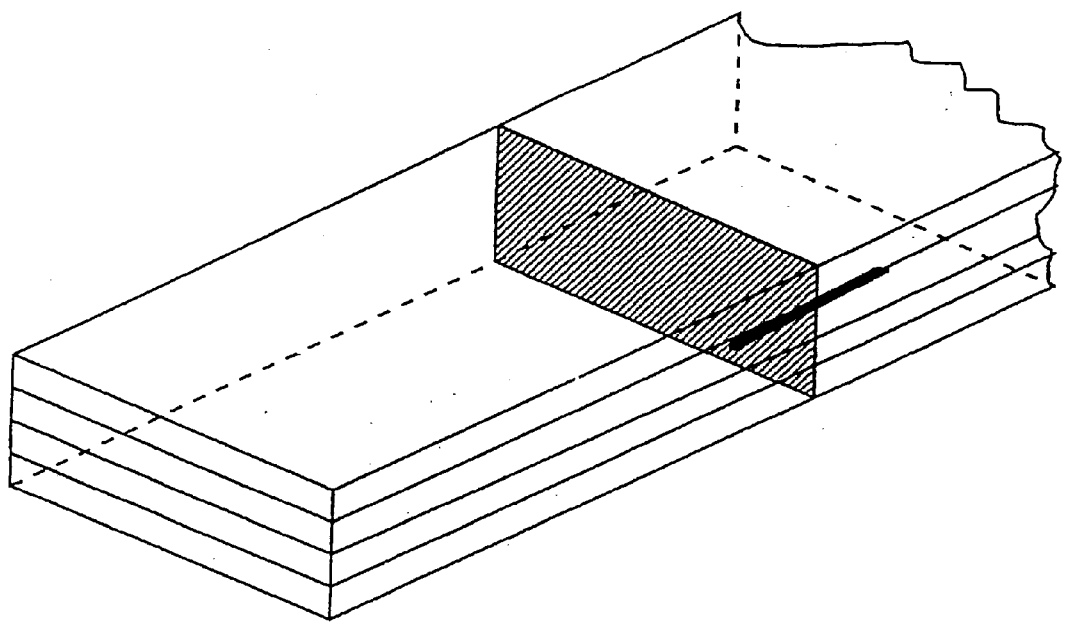

FIG. 64 shows the outer profile of the type 1 (exposed type) NOx gas concentration sensor embodying the present invention and an external circuit connected thereto. The plane of FIG. 64 corresponds to the cross-sectional plane shown shaded in FIG. 65. Referring to FIG. 64, heater devices are bonded, such as by a cement layer, to the main body portion of the sensor, for heating the inside of the first and second flow passages on the upper and lower surfaces in the layering direction of the NOx gas concentration sensor. Between adjacent ones of the solid electrolyte layers 5-1, 5-2, 5-3 and 5-4 are formed insulating layers for preventing the leak current from flowing across the electrodes formed on the different solid electrolyte layers. Although the solid electrolyte layer 5-3 is preferably the same solid electrolyte layer as the layers 5-1, 5-2 and 5-4, it may also be an insulating layer of, for example, alumina. The external circuit connected to the sensor device has already been explained by referring to FIG. 2, so that it is explained here only briefly. That is, electrodes 6b, 7a are electrically connected to each other via a junction which is grounded via a resistor. A first cell voltage Vp1 is applied across the electrode 6a and 6b. The electrode 7b is electrically connected to an inverted input terminal (–) on one side of a differential amplifier, to an opposing (non-inverted) input terminal (+) is entered a reference voltage which is formed as an auto-generating reference electrode due to a small current Icp applied across the pair electrodes 7a—7a. This differential amplifier variably controls current Ip1 applied across the electrodes 6a, 6b so that oxygen concentration in the first measuring chamber 2 will be controlled to a predetermined value by extracting and introducing oxygen by the current Ip1 (orderly and reverse flows).

This enable the current Ip1 to flow across the electrodes 6a, 6b in response to the oxygen concentration in the measurement gas to extract and introduce oxygen across the electrodes 6a, 6b. On the other hand, a constant voltage Vp2 is applied across the electrodes 8a, 8b. The NOx gas concentration in the measurement gas is measured on the basis of the current Ip2 flowing across the electrodes 8a, 8b.

Figure 66:
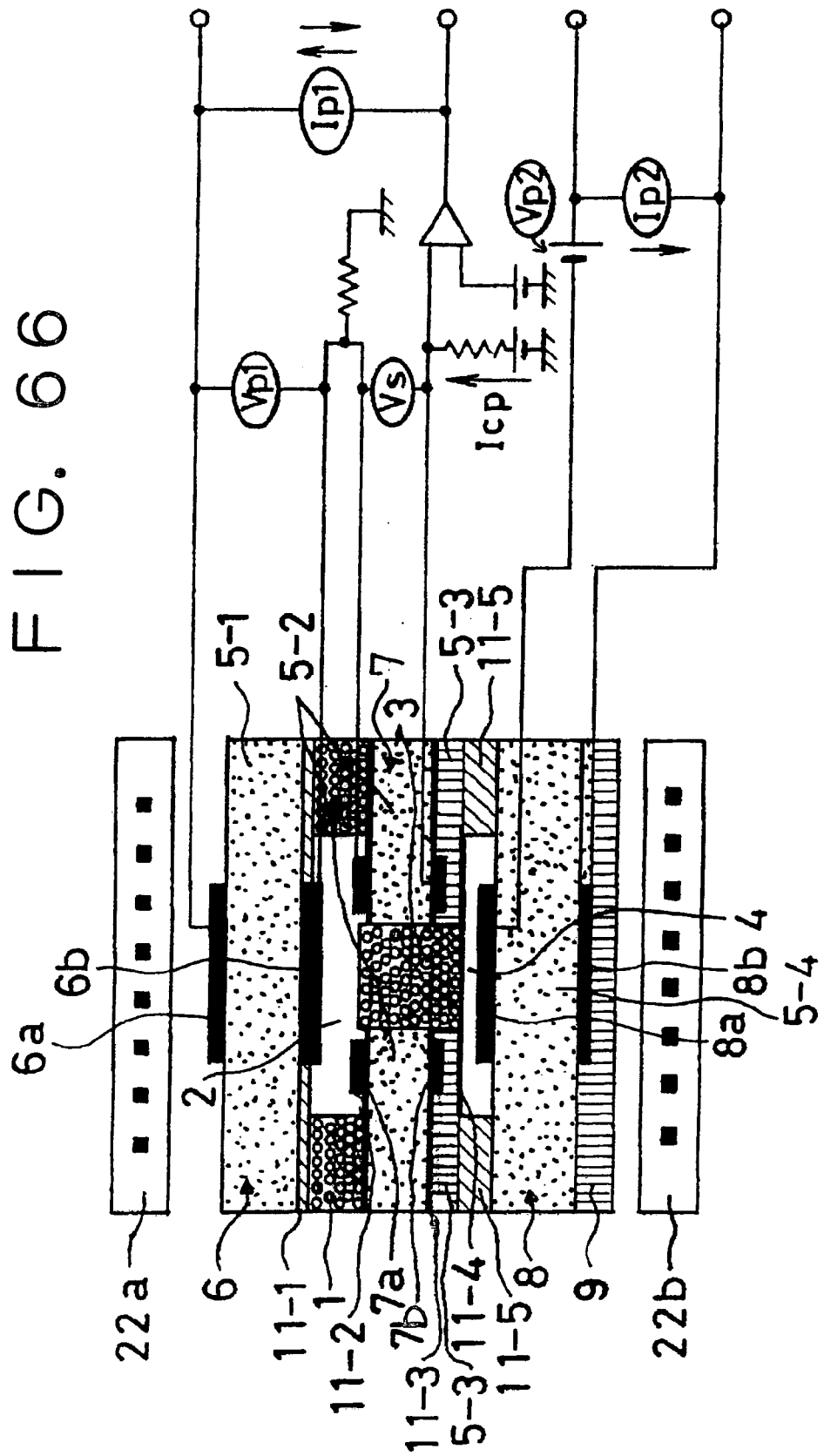

FIG. 66 shows a modification of a type 2 (enclosed type) NOx gas concentration sensor embodying the present invention and an external circuit connected thereto. The plane shown in FIG. 66 is equivalent to the cross-sectional plane shown shaded in FIG. 65. The sensor shown in FIG. 66 differs from the type 1 (exposed type) shown in FIG. 64 in that the outer electrode 8b of the second oxygen ion pump cell is covered by a protective cover 9.

Next, a variety of structural variants of the NOx gas concentration sensor, particularly according to the third aspects group, are illustrated.

[Three-Passage Parallel type]

The sensor shown in FIG. 67 is made up of plural solid electrolyte layers, laminated together. Between adjacent ones of the solid electrolyte layers are formed insulating layers, not shown, for defining three mutually separated flow passages (or channels), of which the second and third flow passages 204a, 204b are arrayed parallel to the first flow passage 202. Specifically, the measurement gas is diffused from the first diffusion hole 201 formed in the lateral side of the sensor device towards the first flow passage 202 extending in the planar direction of the solid electrolyte layers. In the measurement gas, diffused into the first flow passage, oxygen is led out from the gas by the first cell 206 for concentrating the NO gas component. The gas with the concentrated NO is diffused from the first flow passage into the third flow passage 204b via the third diffusion hole 203b extending from the first flow passage 202 in the stacking direction. A relatively low voltage which selectively dissociates NOx is applied across the electrodes 208a, 208b of the NOx gas concentration sensor 208 facing the second flow passage 204a. The NOx gas concentration is detected based on the current flowing between these electrodes 208a, 208b. On the other hand, a higher voltage which will dissociate $H_2O$ and $CO_2$ is applied across the electrodes 209a, 209b of the $H_2O+CO_2$ gas concentration sensor facing the third flow passage 204b for detecting a cumulative concentration of ($H_2O+CO_2+NOx$) gas based on the current flowing between these electrodes 209a, 209b.

There are occasions wherein $H_2O$ and $CO_2$ are dissociated in the vicinity of the inner electrodes of the NOx gas concentration sensor to affect detection of the NOx gas concentration. With this sensor, the NOx gas concentration detected by the NOx as concentration sensor cell can be corrected based on the current flowing through the electrodes of the $H_2O$-$CO_2$ gas concentration sensor cell. This renders it possible to eliminate the effect of interfering gases, such as $H_2O$ or $CO_2$ to realize more accurate measurement of the NOx gas concentration.

[4-Flow Passage Parallel Type]

FIG. 68 shows a modification of the sensor shown in FIG. 67. A fourth flow passage is provided for communicating with the first flow passage 202 via fourth diffusion hole 203C, whilst a $H_2O$ gas concentration sensor cell and a $CO_2$ gas concentration sensor cell 211 are provided facing the third and fourth flow passages 204b, 204c, respectively. An electrical voltage higher than the voltage applied across the $H_2O$ gas concentration sensor cell and which also dissociates $CO_2$ is impressed across the electrodes 211a, 211b of the $CO_2$ gas concentration sensor cell 211. This sensor enables correction of the NOx gas concentration detected by the NOx gas concentration sensor cell based on the current flowing across the electrodes provided on the $H_2O$ gas concentration sensor cell 210 or the $CO_2$ gas concentration sensor cell 211. With the present sensor, the NOx gas concentration can be measured more accurately without being influenced by interfering gases, while the concentration of the $H_2O$ or $CO_2$ gases can also be measured.

[3-Flow Passage Serial Type]

Figure 69:
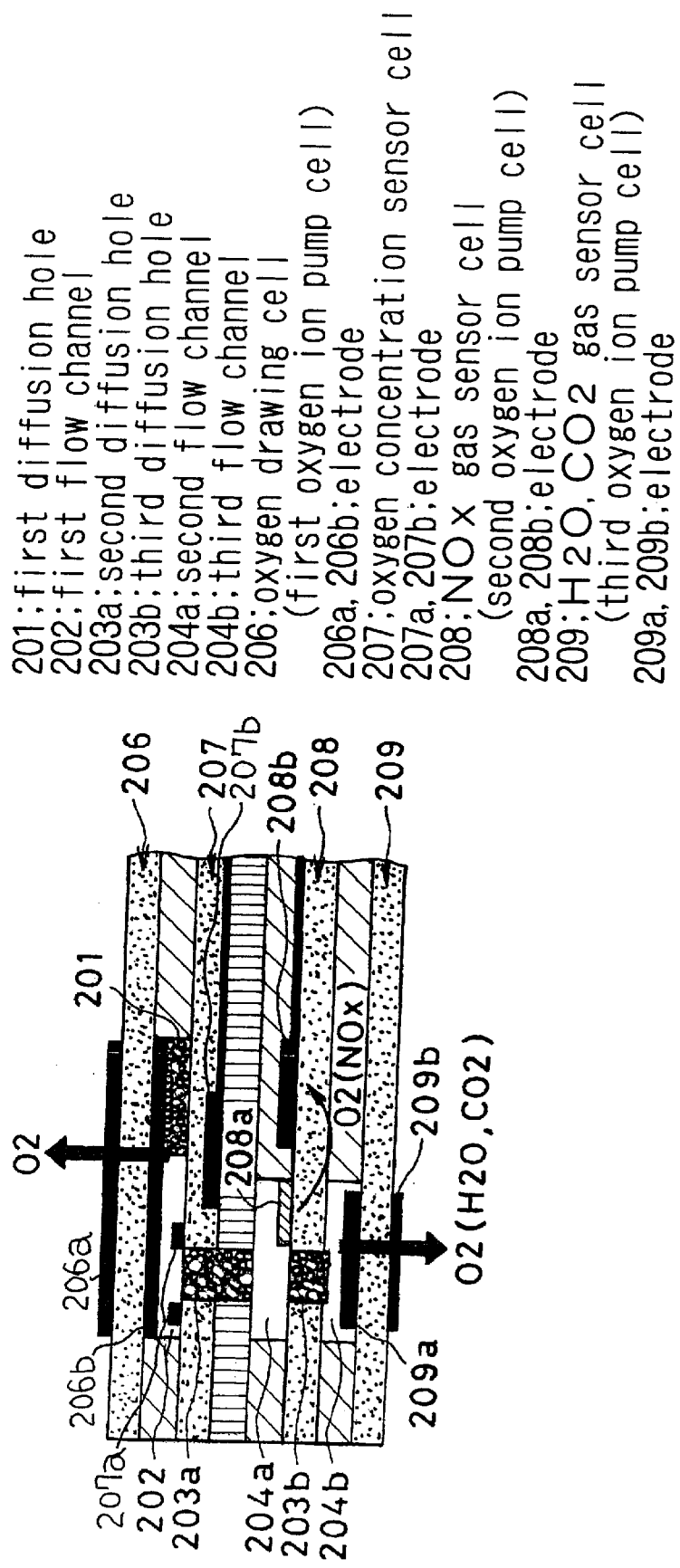

With a NOx gas concentration sensor, shown in FIG. 69, solid electrolyte layers are layered together. Between adjacent ones of the solid electrolyte layers are formed insulating layers, not shown for defining three mutually spaced flow passages, namely first to third flow passages 202, 203a, 203b, which are serially arranged in order along the stacking direction of the solid electrolyte layers. Specifically, the measurement gas is diffused from the first diffusion hole 201 formed in the lateral side of the sensor device into the first flow passage 202 extending along the plane of the solid electrolyte layers. The measurement gas, diffused into the first flow passage 202, has the NO gas component concentrated by removing oxygen from the gas by the first cell 206. The gas with concentrated NO is diffused via the second diffusion hole 203a extending in the stacking direction of the solid electrolyte layers into the second flow passage 204a, while being diffused from the second flow passage via third diffusion hole 203b extending in the layering direction into the third flow passage 204b. That is, the main gas flow direction is the stacking direction. A smaller voltage which selectively dissociates NOx is impressed across the electrodes 208a, 208b of the NOx gas concentration sensor 208 facing the second flow passage 204a for detecting the NOx gas concentration based on the current flowing across these electrodes 208a, 208b. A higher voltage which dissociates $H_2O$ and $CO_2$ is applied across the electrodes of the $H_2O$—$CO_2$ gas concentration sensor cell 209 facing the third flow passage 204b into which the gas with dissociated NOx is diffused for enabling detection of the $H_2O$—$CO_2$ gas concentration (superposed gas concentration) based on the current flowing across these electrodes. It is possible with this sensor to correct the NOx gas concentration detected by the NOx gas concentration sensor cell 208 based on the current flowing across the electrodes of the $H_2O$—$CO_2$ gas concentration sensor cell. This assures more accurate measurement of the NOx gas concentration in a manner free from the effect of the interfering gases, such as $H_2O$ or $CO_2$.

[4-Flow Path Serial Type]

A NOx gas concentration sensor shown in FIG. 70 is a modification of the sensor shown in FIG. 69. A fourth flow passage 204c communicating with the third flow passage 204b is provided between the solid electrolyte layers via a third diffusion hole 203b extending in the stacking direction of the solid electrolyte layers. In the present sensor, a $H_2O$ gas concentration sensor 210 and a $CO_2$ gas concentration sensor 211 are provided facing the third flow passage 204b and the fourth flow passage 204c, respectively. An electrical voltage higher than the voltage impressed across the electrodes of the $H_2O$ gas concentration sensor and which dissociates $CO_2$ is impressed across the electrodes of the $CO_2$ gas concentration sensor cell. It is possible with this sensor to correct the NOx gas concentration as detected by the NOx gas concentration sensor cell based on the current flowing across the electrodes of the $H_2O$ gas concentration sensor or the $CO_2$ gas concentration sensor. This enables more accurate measurement of the NOx gas concentration in a manner free from adverse effects of the interfering gases, such as $H_2O$ or $CO_2$. It is moreover possible with the present sensor to measure the $H_2O$ or $CO_2$ gas concentration.

Figure 71:
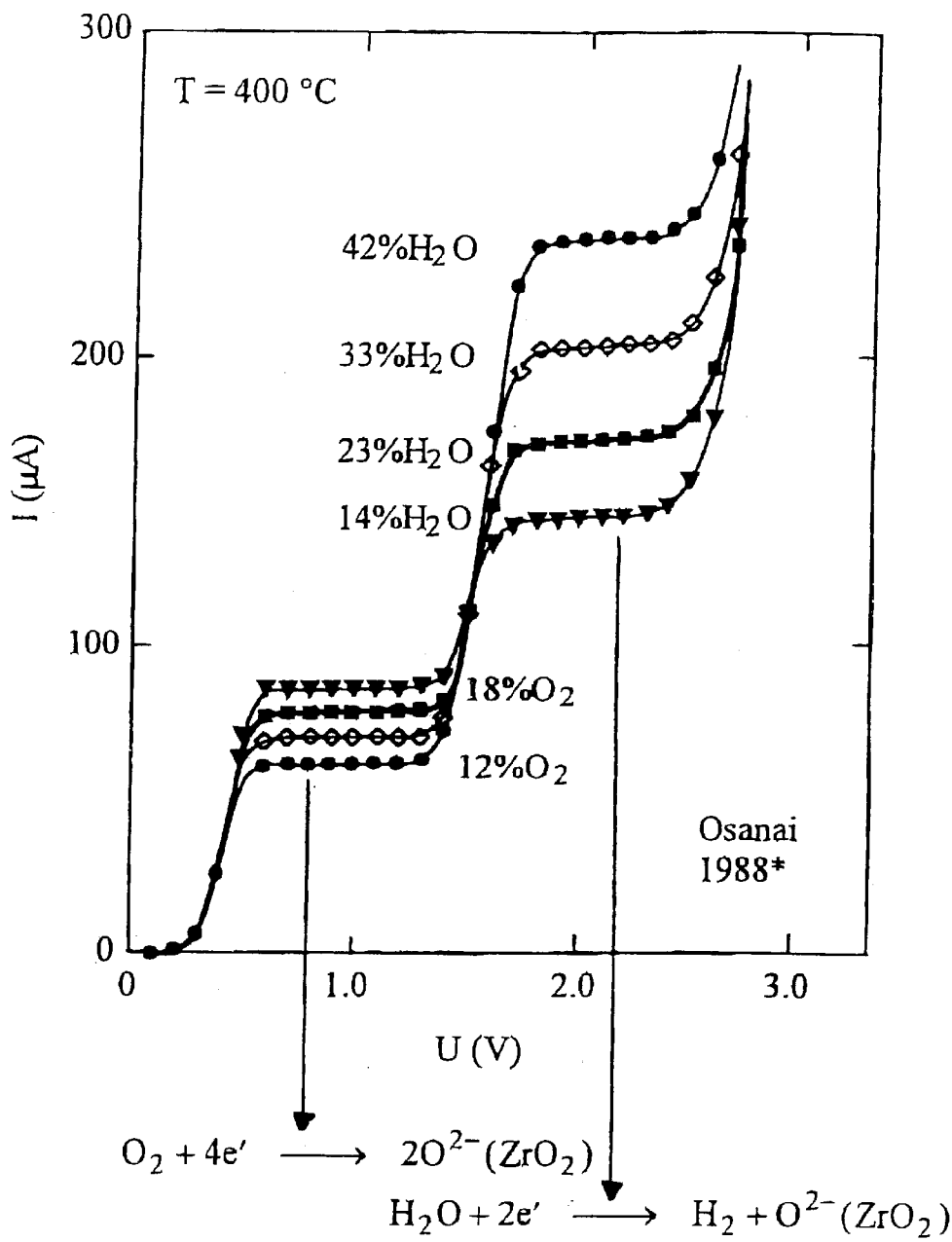
FIG. 71 is a diagram showing the dissociation voltage of oxygen and water.

FIG. 71 shows the dissociation voltage of $O_2$ and $H_2O$ reported by H. Osanai et al, Fujikura Technical Review 17(1988), 34–42. Basically, the NO dissociation voltage is higher than that between those of $O_2$ and $H_2O$, while the $CO_2$ dissociation voltage is higher than that for $H_2O$. However, the atmosphere in the flow passage provided on the sensor of the present invention differs in e.g., oxygen concentration or temperature from that under which data shown in FIG. 71 were obtained, such that the dissociation voltage between different components are thought to approach to one another. Therefore, if desired to detect the NOx gas concentration correctly, the voltage impressed across the NOx dissociating electrodes needs to be carefully determined so as not to dissociate interfering gas components, such as $H_2O$.

Generally, the present invention has demonstrated the conditions and requirements for achieving the same, as well as provides measuring apparatus and method which can effectively remove the adverse influence of the interfering gas components for precisely measuring the NOx concentration.

With the present invention, as described above, the $H_2O$ concentration dependency or oxygen concentration dependency of the NOx gas measurement is reduced by measuring the voltage impressed across the second oxygen ion pump cell to a pre-set range such as not to dissociate $H_2O$, thus enabling accurate measurement of the NOx gas concentration. By controlling the oxygen concentration in the second measurement chamber to a value of not dissociating $H_2O$, it becomes possible to improve in particular the $H_2O$ concentration dependency of the offset of the second oxygen ion pump cell current Ip2. On the other hand, since it has turned out that the optimum setting voltage Vp2 differs with the atmosphere in which is placed the one of the paired electrodes of the second oxygen ion pump cell that is disposed on the outer side of the second measurement chamber, there is now obtained the guideline for setting optimum Vp2 in a variety of sensor configurations.

(2) nNO of step (1) is dissociated into $n/2 N_2 + n/2 O_2$

This $n/2 O_2$ is transmitted as oxygen ion through the oxygen ion conductor to measure a current caused by the oxygen ion transmission, through which a value proportionate to the current is obtained. Namely by determining n of NO, the amount of nNOx can be determined.

Ideally, the sensor should forward the NO generated at step (1) without subjecting to decomposition. However, certain amount of dissociation of the generated NO at step (1) may occur even under the best suited conditions (e.g., in FIG. 21C or 21D). The dissociation rate between NO and (N+O) is governed by influences of various parameters such as the applied voltage at step (1), and materials and design/configuration of the electrodes. Therefore, it is most preferred to compensate for substantial decomposition of NO in the step (1). Typically, the compensation can be performed by the inverse of the dissociation rate of NO into (N+O) (e.g., 60 to 95%).

It should be noted that modifications may be made within the gist and scope of the present invention as herein disclosed and claimed.

TABLE 1

OXYGEN DETECTING ELECTRODE Vs = 360 mV
※ BALANCE IS $N_2$

| MIXED GAS | $H_2O$ = 0% Ip2 [µA] | | | $H_2O$ = 10% Ip2 [µA] | | | $H_2O$ 10%, NO = 1000 ppm Ip2 [µA] | | |
|---|---|---|---|---|---|---|---|---|---|
| Vp2 [mV] | TEST EX.1 O2 1% | TEST EX.2 7% | TEST EX.3 16% | TEST EX.4 1% | TEST EX.5 7% | TEST EX.6 16% | TEST EX.7 1% | TEST EX.8 7% | TEST EX.9 16% |
| 50 | −56.64 | −178.49 | −249.56 | −56.74 | −175.44 | −238.98 | −55.74 | −171.86 | −238.71 |
| 100 | −12.05 | −69.41 | −114.38 | −12.98 | −67.89 | −108.94 | −11.45 | −65.98 | −108.33 |
| 150 | 1.31 | −15.67 | −33.04 | −0.26 | −15.11 | −31.21 | 2.95 | −13.48 | −30.36 |
| 200 | 3.78 | −1.38 | −5.03 | 1.98 | −1.42 | −5.07 | 7.24 | 1.96 | −2.56 |
| 300 | 4.36 | 1.58 | 1.38 | 2.99 | 1.49 | 0.89 | 10.73 | 8.53 | 7.79 |
| 350 | 4.47 | 1.68 | 1.56 | 4.03 | 1.91 | 1.32 | 12.25 | 9.97 | 9.48 |
| 400 | 4.63 | 1.69 | 1.59 | 6.69 | 3.02 | 2.14 | 15.21 | 13.85 | 11.03 |
| 450 | 4.76 | 1.76 | 1.65 | 14.58 | 5.87 | 4.35 | 21.98 | 14.63 | 13.46 |
| 500 | 4.85 | 1.86 | 1.68 | 29.08 | 12.88 | 9.63 | 36.95 | 21.75 | 18.84 |
| 600 | 5.11 | 2.07 | 1.89 | 111.39 | 62.85 | 49.72 | 117.16 | 70.98 | 57.96 |
| 700 | 7.16 | 3.05 | 3.08 | 288.55 | 213.56 | 180.17 | 293.81 | 215.34 | 190.35 |
| 800 | 11.75 | 7.35 | 7.97 | 572.63 | 482.78 | 435.21 | 575.35 | 482.65 | 442.31 |

If the potential of the oxygen partial pressure detection electrode is set to 150 to 450 mV and preferably the one of the paired electrodes of the second oxygen ion pump cell that is positioned towards outside of the second measurement chamber is exposed to or not exposed to the atmosphere under measurement, the potential of the electrode of the second oxygen ion pump cell can be set to 300 to 400 mV or to 400 to 500 mV, respectively, for enabling more accurate measurement of the NOx gas concentration.

Generally, the Nox concentration in the gas is determined based on the following phenomenon: Namely, almost $NO_2$ will be deemed to be dissociated into NO and $\frac{1}{2}O_2$ in a gas atmosphere of high temperature, e.g., at 800° C. under normal pressure in which a very small amount of $NO_2$ in an amount of e.g., 0.1% (1000 ppm) is present together with other gases, thus which is deemed to be equivalent to the presence of 0.1% of NO.

The measurement is carried out basically under the following principle.

(1) At a high temperature (700° C. or above), the amount of $NO_2$ contained as nNOx ($NO_2$) is dissociated into nNO+ $n/2 O_{1-n}$, and subjected to removal of the generated $n/2 O_{1-x}$;

TABLE 2

•OXYGEN DETECTING ELECTRODE = 450 mV
※ BALANCE IS $N_2$

| MIXED GAS | H2O 10%. | | H2O 10%, NO = 1000 ppm | |
|---|---|---|---|---|
| | Ip2 [µA] | | Ip2 [µA] | |
| Vp2 [mV] | TEST EX. 10 O2 1% | TEST EX. 11 16% | TEST EX. 12 1% | TEST EX. 13 7% |
| 200 | 0.35 | −5.10 | 4.25 | −2.65 |
| 250 | 0.98 | 0.45 | 6.57 | 4.63 |
| 300 | 1.66 | 1.51 | 8.45 | 7.63 |
| 350 | 2.84 | 2.17 | 10.22 | 9.43 |
| 400 | 6.52 | 3.16 | 13.84 | 11.11 |
| 450 | 14.84 | 5.89 | 21.65 | 14.07 |

TABLE 3

※ BALANCE IS N₂

MIXED GAS
$O_2 = 7\%$, $CO_2 = 10\%$

|  | TEST EX. 14 | TEST EX. 15 | TEST EX. 16 | TEST EX. 17 |
|---|---|---|---|---|
| Vs [mV] | 350 | 350 | 450 | 450 |
| Vp2 [mV] | 450 | 350 | 350 | 350 |
| Ip2 [µA] | | | | |
| H2O = 0% | 4.73 | 4.32 | 2.33 | 1.41 |
| H2O = 10% | 8.26 | 4.32 | 1.97 | 1.46 |

TABLE 4

※ BALANCE IS N₂

MIXED GAS
$CO_2 = 10\%$, $H_2O = 10\%$

|  | TEST EX. 18 | TEST EX. 19 | TEST EX. 20 | TEST EX. 21 |
|---|---|---|---|---|
| Vs [mV] | 350 | 350 | 450 | 450 |
| Vp2 [mV] | 450 | 350 | 350 | 300 |
| Ip2 [µA] | | | | |
| O2 | | | | |
| 1% | 14.18 | 4.38 | 3.84 | 2.41 |
| 7% | 8.26 | 4.32 | 1.97 | 1.46 |
| 16% | 8.23 | 5.11 | 2.01 | 1.40 |

TABLE 5

※ BALANCE IS N₂

MIXED GAS
$O_2 = 7\%$, $CO_2 = 10\%$

|  | TEST EX. 22 | TEST EX. 23 | TEST EX. 24 | TEST EX. 25 |
|---|---|---|---|---|
| Vs [mV] | 350 | 350 | 450 | 450 |
| Vp2 [mV] | 450 | 350 | 350 | 300 |
| Gain [µA] | | | | |
| H2O = 0% | 9.26 | 8.85 | 7.58 | 7.19 |
| H2O = 10% | 9.52 | 8.70 | 7.69 | 6.90 |

TABLE A1

| Type | A (mm) |
|---|---|
| Type 1 | 3 |
| Type 2 | 1.5 |
| Type 3 | 0 |
| Type 4 | Conventional type |

TABLE A2

Relation between Vs set and Ip2

|  | Ip2 (µA) | | | |
|---|---|---|---|---|
| Vs (mV) | Type 1 | Type 2 | Type 3 | Type 4 |
| 200 | 14.75 | 14.2 | 13.7 | 13.68 |
| 250 | 13.38 | 14 | 14.57 | 12.19 |

TABLE A2-continued

Relation between Vs set and Ip2

|  | Ip2 (µA) | | | |
|---|---|---|---|---|
| Vs (mV) | Type 1 | Type 2 | Type 3 | Type 4 |
| 300 | 12.41 | 12.65 | 12.92 | 8.13 |
| 350 | 10.89 | 11 | 3.76 | 3.1 |
| 400 | 9.89 | 8.75 | 2.81 | 1.2 |
| 450 | 9.08 | 3.25 | | |

TABLE A3

| Oxygen Concentration | Ip2 (µA) | | | |
|---|---|---|---|---|
| (%) | Type 1 | Type 2 | Type 3 | Type 4 |
| 1 | 19.35 | 35 | 55 | 87.28 |
| 4 | 9.95 | 23 | 41 | 66.89 |
| 7 | 6.1 | 19 | 35 | 54.22 |
| 20 | 4.12 | 14 | 29 | 61.56 |

TABLE A4

Relation between Heater Power and Ip2

| Heater Power | Ip2 (µA) | |
|---|---|---|
| (W) | Type 1 | Type 4 |
| 20.475 | | 54.22 |
| 17.575 | | 23.94 |
| 14.79 | | 40.92 |
| 21.52 | 36.36 | |
| 18.76 | 14.05 | |
| 17.23 | 8.2 | |
| 16.02 | 6.15 | |
| 14.87 | 5.2 | |
| 13.62 | 5.3 | |

TABLE B1

Relation between Oxygen Concentration and Ip2 Offset

| Oxygen Concentration | I p2, offset (µA) | | |
|---|---|---|---|
| (%) | Example 1 | Example 2 | Example 3 |
| 16 | 5.18 | 3.18 | 9.87 |
| 7 | 7.83 | 4.87 | 11.1 |
| 0.5 | 17.25 | 8.32 | 28.77 |
| 0 | 25.57 | 10.44 | 68.03 |

TABLE B2

Relation between Oxygen Concentration and Gain (Δ Ip2)

| Oxygen Concentration | Δ I p2 offset (µA) | | |
|---|---|---|---|
| (%) | Example 1 | Example 2 | Example 3 |
| 16 | 14.85 | 14.69 | 12.31 |
| 7 | 14.41 | 14.07 | 11.66 |
| 0.5 | 12.79 | 12.83 | 9.68 |
| 0 | 9.68 | 11.72 | 4.59 |

TABLE C1

Relation between Oxygen Concentration and Offset, Gain, Vp1 Oxygen Pump Electrode (of 4 mm)

| Oxygen Concentration 0.2% | IP2 Offset ($\mu$A) | | $\Delta$ IP2 Gain ($\mu$A) | | VP1 (mV) | |
|---|---|---|---|---|---|---|
| | Improved | Control | Improved | Control | Improved | Control |
| 1 | 6.475 | 7.45 | 13.31 | 12.31 | 151.2 | 184.05 |
| 7 | 5.89 | 4.63 | 13.51 | 13.155 | 231.3 | 274.9 |
| 16 | 5.475 | 4.265 | 13.56 | 13.28 | 331.9 | 388.7 |

TABLE C2

Relation between Temperature and Offset, Gain, Vp1 Oxygen Pump Electrode (of 4 mm)

| Heater Power (W) | Offset ($\mu$A) | Gain ($\mu$A) | VP1 (mV) |
|---|---|---|---|
| 24.985 | 5.385 | 12.535 | 225.4 |
| 22.99 | 4.78 | 12.255 | 229.65 |
| 20.969 | 4.16 | 11.955 | 254.35 |
| 18.945 | 5.115 | 11.36 | 354.4 |
| 24.989 | 5.535 | 13.67 | 268.45 |
| 22.995 | 3.61 | 13.67 | 290.8 |
| 20.976 | 2.465 | 13.1 | 358.45 |
| 19.05 | 2.32 | 10.47 | 501.8 |

TABLE C3

Relation between Oxygen Concentration and Offset, Gain, VP1 Oxygen Pump Electrode (of 4 mm)

| Heater Power (W) | Offset ($\mu$A) | Gain ($\mu$A) | VP1 (mV) |
|---|---|---|---|
| 21.47 | −30.01 | 1.4 | 994.8 |

TABLE D1

Relation between Oxygen Concentration and Ip2 Offset

| Oxygen Concentration (%) | Ip2 Offset ($\mu$A) | | | |
|---|---|---|---|---|
| | Example 1 | Example 2 | Example 3 | Comparative Example |
| 16 | 3.65 | 2.43 | 2.75 | 5.33 |
| 7 | 3.95 | 2.54 | 2.63 | 8.31 |
| 1 | 4.14 | 2.99 | 2.69 | 14.53 |
| 0.5 | 4.15 | 3.11 | 2.83 | 20.02 |
| 0 | 4.03 | 3.24 | 2.65 | 50.51 |

TABLE D2

Relation between Oxygen Concentration and Gain ($\Delta$ Ip2)

| Oxygen Concentration (%) | $\Delta$ I p 2 Offset ($\mu$A) | | | |
|---|---|---|---|---|
| | Example 1 | Example 2 | Example 3 | Comparative Example |
| 16 | 12.74 | 12.5 | 13.75 | 12.65 |
| 7 | 11.93 | 11.84 | 12.8 | 11.66 |
| 1 | 11.39 | 11.45 | 12.19 | 10.51 |
| 0.5 | 11.32 | 11.41 | 12.09 | 9.68 |
| 0 | 11.15 | 11.33 | 11.98 | 4.59 |

What is claimed is:

1. A method for determining NOx concentration in a measurement gas comprising NOx, $O_2$, $CO_2$ and $H_2O$, under a varying condition of the NOx concentration in the measurement gas in the course that the measurement gas is allowed to travel through a flow channel facing a ceramic body having an electrically controllable conducting rate of oxygen ion, wherein the method comprises:
(1) introducing the measurement gas into the flow channel;
(2) forming an NO-concentrated residual gas in said flow channel under a condition that allows substantial decomposition of NOx, said NO-concentrated residual gas having a NOx concentration different from the measurement gas and extracting said $O_2$ from the measurement gas introduced into the flow channel;
(3) dissociating NO of said NO-concentrated residual gas into nitrogen and oxygen by applying across electrodes formed on the ceramic body a voltage to an extent that does not substantially dissociate said $H_2O$ or said $CO_2$ in the NO-concentrated residual gas;
(4) measuring an electric current flowing through the ceramic body between the electrodes, said electric current being generated by an electrochemical action of the oxygen dissociated from the NO in step (3); and
(5) determining the NOx concentration of the measurement gas based on the electric current measured in step (4).

2. The method as defined in claim 1 wherein, in step (1), the flow of the measurement gas into said flow channel is restricted.

3. The method as defined in claim 1 wherein, between steps (2) and (3), the flow of the residual gas to the electrodes of the step (3) is restricted.

4. The method as defined in any one of claims 1 to 3 wherein said flow channel comprises a first flow channel and a second flow channel communicating with the first flow channel, said formation of the NOx residual gas of said step (2) is performed in the first flow channel, and wherein NOx in step (3) is dissociated in the second flow channel.

5. The method as defined in claim 1 wherein in step (2) the NO-concentrated residual gas is formed under a condition that allows and compensates for substantial decomposition of NOx in the flow channel.

6. The method as defined in claim 4 wherein in the first flow channel the NO-concentrated residual gas is formed under a condition that allows and compensates for substantial decomposition of NOx in the first chamber.

7. The method as defined in claim 1 wherein in step (3) the voltage is applied to an extent that does not substantially dissociate $H_2O$ in the NO concentrated residual gas.

8. The method as defined in claim 1 wherein in step (3) the voltage is applied to an extent that does not substantially dissociate $CO_2$ in the residual gas.

9. A method for determining NOx concentration in a measurement gas comprising NOx, $O_2$, $H_2O$ and $CO_2$, said method employing an electrically controlled electrochemical cell comprising at least one oxygen ion conductive solid electrolyte body and a catalytic electrode formed on the electrolyte body, comprising:

wherein the method comprises:

(1) introducing the measurement gas through a flow channel formed in the oxygen ion conductive solid electrolyte body that electrically controls an amount of $O_2$ in the flow channel;

(2) forming an NO-concentrated residual gas at a temperature of at least 700 C. by decomposition of NOx in the flow of the measurement gas;

(3) contacting said NO-concentrated residual gas with the catalytic electrode to which a negative polarity of a dc voltage that does no substantially dissociate said H2O or said $CO_2$ but dissociates NO contained in the NO-concentrated residual gas is applied;

(4) dissociating said NO contained in the NO-concentrated residual gas into N-ions and O-ions at the catalytic electrode and flowing an electric current through the electrolyte body in proportion to an amount of the O-ions dissociated from said NO at the catalytic electrode; and (5) measuring the current flowing through the electrolyte body and determining the NOx concentration in the measurement gas based on the electric current measured.

10. The method as defined in claim 9 further comprising:

flowing the NO-concentrated residual gas into a reservoir formed adjacent to said flow channel, said catalytic electrode being formed on a wall of the reservoir.

11. The method as defined in claim 10, further comprising:

applying a negative polarity of a voltage to a second electrode formed on a wall of said flow channel and extracting said $O_2$ out of the flow channel to lower an oxygen concentration of the measurement gas flowed in the flow channel.

12. The method as defined in claim 10, further comprising:

applying a negative voltage to a third electrode formed around an inlet of the reservoir and detecting said $O_2$ concentration in the flow channel to control an oxygen concentration of the NO-concentrated residual gas flowed in the reservoir.

13. The method as defined in claim 11, wherein said second electrode formed on the wall of the flow channel faces its surface in parallel to a surface of the catalytic electrode formed on the reservoir wall.

14. The method as defined in claim 10, wherein said reservoir is formed in between two oxygen ion conductive solid electrolyte bodies that are electrically insulated from each other.

15. The method as defined in claim 9, further comprising heating said electrolyte body to a temperature of at least 700° C.

16. The method as defined in claim 14, further comprising heating said oxygen ion conductive solid electrolyte body to a temperature of 700–900° C.

17. The method as defined in claim 9, wherein the dc voltage is applied across the catalytic electrode and an electrode that is formed outside of the electrolyte body, and said dc voltage is in the range of from dc 300 mV to dc 500 mV where $H_2O$ in the NO-concentrated residual gas does not substantially dissociate on the surface of the catalytic electrode and a maximum gain of NOx detection is obtained.

18. The method as defined in claim 17, wherein the dc voltage is about 450 mV.

19. A method for determining NOx concentration in a measurement gas comprising NOx, $O_2$, $H_2O$ and $CO_2$, said method employing an electrically controlled electrochemical cell comprising at least one oxygen ion conductive solid electrolyte body and at least one catalytic electrode formed on the electrolyte body, comprising:

(1) introducing the measurement gas through a flow channel formed in the oxygen ion conductive solid electrolyte body that electrically controls an amount of $O_2$ in a first part of the flow channel, (2) forming a NO-concentrated residual gas at a temperature under a condition that allows and compensates for substantial decomposition of NO in the first part of the flow channel, said NO-concentrated residual gas having a different NO-concentration than that of the measurement gas, (3) contacting said NO-concentrated residual gas with the catalytic electrode to which a dc voltage is applied that does not substantially dissociate said $H_2O$ or said $CO_2$ but dissociates NO contained in the NO-concentrated residual gas, (4) dissociating said NO contained in the NO-concentrated residual gas in a second part of the flow channel into N-ions and O-ions to cause an electric current to flow through the electrolyte body, said current being being in proportion to an amount of the O-ions dissociated from said NO gas at the electrode, and (5) determining the NOx concentration in the measurement gas based on the current with a compensation for the decomposed NO in the first part of the flow channel.

20. The method as defined in claim 19, wherein said dc voltage is controlled so that $H_2O$ or $CO_2$ in the NO-concentrated residual gas do not substantially dissociate on the surface of the electrode and a maximum gain of NOx detection is obtained.

21. The method as defined in claim 19 or 20, wherein the temperature of the electrolyte is controlled so that $H_2O$ or $CO_2$ in the NO-concentrated residual gas do not substantially dissociate on the surface of the electrode and a maximum gain of NOx detection is obtained.

22. The method as defined in claim 19, wherein said dc voltage is in the range of from dc 300 mV to dc 500 mV.

23. The method as defined in claim 19, wherein said dc voltage is in the range of from dc 300 mV to about dc 450 mV.

24. The method as defined in claim 19, wherein said high temperature is at least 700° C.

25. The method as defined in claim 19, wherein said high temperature is 700–900° C.

* * * * *